(12) United States Patent
Hartwig et al.

(10) Patent No.: US 9,938,204 B2
(45) Date of Patent: Apr. 10, 2018

(54) INTERMOLECULAR C-H SILYLATION OF UNACTIVATED ARENES

(71) Applicant: THE REGENTS OF THE UNIVERSITY OF CALIFORNIA, Oakland, CA (US)

(72) Inventors: John F. Hartwig, Berkeley, CA (US); Chen Cheng, Berkeley, CA (US); Tyler Wilson, Redwood City, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/916,787

(22) PCT Filed: Sep. 8, 2014

(86) PCT No.: PCT/US2014/054602
§ 371 (c)(1),
(2) Date: Mar. 4, 2016

(87) PCT Pub. No.: WO2015/035325
PCT Pub. Date: Mar. 12, 2015

(65) Prior Publication Data
US 2016/0200639 A1   Jul. 14, 2016

Related U.S. Application Data

(60) Provisional application No. 61/874,729, filed on Sep. 6, 2013.

(51) Int. Cl.
*C07F 7/00* (2006.01)
*C07B 47/00* (2006.01)
*C07F 7/08* (2006.01)
*C07F 7/18* (2006.01)

(52) U.S. Cl.
CPC .............. *C07B 47/00* (2013.01); *C07F 7/085* (2013.01); *C07F 7/0807* (2013.01); *C07F 7/0829* (2013.01); *C07F 7/0849* (2013.01); *C07F 7/0852* (2013.01); *C07F 7/0854* (2013.01); *C07F 7/0856* (2013.01); *C07F 7/0881* (2013.01); *C07F 7/188* (2013.01); *C07F 7/1844* (2013.01); *C07F 7/1876* (2013.01)

(58) Field of Classification Search
CPC ..... C07F 7/0854; C07F 7/0856; C07F 7/1844
USPC ............................................... 556/479, 487
See application file for complete search history.

(56) References Cited

FOREIGN PATENT DOCUMENTS
WO   WO 2015/035325   3/2015

OTHER PUBLICATIONS

Simmons (Journal of the American Chemical Society, 132 (48), 2010, 17092-17095).*
Blankenstein, J.; Pflatz, A. Angew Chem. Int. Ed., 40, 4445-47 (2001).
Braunstein, P. et al., Organometallics, 19, 2676-2683 (2000).
Buswell, et al., Org. Biomol. Chem. 2:3006-3017 (2004).
Cheng, et al., Tetrahedron Lett. 44:7095-7098 (2003).
Cheng et al., Chem. Commun. 48, 2906-2908 (2012).
Choi, et al., J. Am. Chem. Soc., (2013).
Cramer, R., Inorg. Synth. 15:14-18 (1974).
Dieguez, M.; Pamies, O. Acc. Chem. Res., 43, 312-22 (2010).
Ent, et al., Inorg. Synth. 27:90-92 (1990).
Ezbiansky, et al., Organometallics 17:1455-1457 (1998).
Fier, et al., J. Am. Chem. Soc. 135:2552-2559 (2013).
Godula, et al., Science 312:67-72 (2006).
Hartwig, Acc. Chem. Res. 45:864-873 (2012).
Ihara, et al., J. Am. Chem. Soc. 131:7502-7503 (2009).
Ishikawa, et al., Organometallics 11:4135-4139 (1992).
Ishikawa et al., Synthesis, 13, 2176-2182 (2005).
Ishiyama, et al., Angew. Chem. Int. Ed. 42:5346-5348 (2003).
Jagt, R. et al., J. Org. Lett., 7, 2433-35 (2005).
Kakiuchi, et al., Chem. Lett. 30:422-423 (2001).
Krapcho et al, S., J. Heterocyclic Chem. 45, 1167-1170 (2008).
Kayaki, Y. et al. J. Org. Chem., 69, 2595-97 (2004).
Kuninobu, et al., Org. Lett. 15:426-428 (2013).
Liskey, et al., J. Am. Chem. Soc. 132:11389-11391 (2010).
Liu, S., Sandoval, C. A.; Molecular. Catalysis. A, 325, 65-72 (2010).
Lu, et al., Angew. Chem. Int. Ed. 47:7508-7510 (2008).
Lyons, et al., Chem. Rev. 110:1147-1169 (2010).
Malda, H. et al., Org. Lett., 3, 1169-1171 (2001).
Martorell, A. et al., Tetrahedron Asymmetry,12, 2497-2499 (2001).
Mkhalid, et al., Chem. Rev. 110:890-931 (2010).
Minnaard, A. J. et al., Acc. Chem. Res. 40, 1267-77 (2007).
Monnereau, L. et al., Adv. Synth. Catal. 351, 1629-36 (2009).
Moon, J.; Lee, S. J. Organometal. Chem., 694, 473-77 (2009).
Murata, et al., Chem. Lett. 36:910-911 (2007).
Murphy, et al., J. Am. Chem. Soc. 129:15434-15435 (2007).
Oyamada, et al., Angew. Chem. Int. Ed. 50, 10720-10723 (2011).
Park, H.; Kumareswaran, R.; Rajanbabu, T. V. R. Tetrahedron, 61, 6352-67 (2005).
Peng, X. et al., Tetrahedron Lett., 49, 4862-4864 (2008).
Poole, et al., Org. Biomol. Chem. 3:1013-1024 (2005).
Punji, B. et al., Dalton Trans, 1322-1330 (2006).
Saiki, et al., Organometallics 25:6068-6073 (2006).
Sakakura, et al., Chem. Lett. 16:2375-2378 (1987).
Shashack, et al., ACS Chem. Neurosci. 2:640-644 (2011).
Simmons, et al., J. Am. Chem. Soc. 132:17092-17095 (2010).
Simmons, et al., Nature 483:70-73 (2012).
Tajuddin, et al., Chem. Sci. 3:3505-3515 (2012).

(Continued)

*Primary Examiner* — Pancham Bakshi
(74) *Attorney, Agent, or Firm* — Morgan, Lewis & Bockius LLP; Jeffry S. Mann

(57) ABSTRACT

Reaction mixtures for silvlating arene substrates and methods of using such reaction mixtures to silyiate the arene substrates are provided. Exemplary reaction mixtures include the arene substrate, a liganded metal catalyst, a hydrogen acceptor and an organic solvent. The reaction conditions allow for diverse substituents on the arene substrate.

30 Claims, No Drawings

(56) References Cited

OTHER PUBLICATIONS

Ureshino, et al., J. Am. Chem. Soc. 132:14324-14326 (2010).
Vanchura, et al., Chem. Commun. 46:7724-7726 (2010).
Watahiki, et al., Green Chem. 5:82-84 (2003).
Werner, et al., J. Chem. Soc., Dalton Trans., 3549-3558 (1998).
Williams, et al., J. Chem. Soc., Chem. Commun., 1129-1130 (1995).

* cited by examiner

INTERMOLECULAR C-H SILYLATION OF UNACTIVATED ARENES

CROSS REFERENCE TO RELATED APPLICATIONS

This application claims, under 35 USC 119(e), the benefit of U.S. Provisional Application No. 61/874,729 filed Sep. 6, 2013, which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under Grant No. CHE1213409 awarded by the National Science Foundation. The Government has certain rights in the invention.

BACKGROUND OF THE INVENTION

Methods for the selective functionalization of aromatic C—H bonds under mild, neutral conditions have been shown to be useful for a wide range of applications, ranging from material science to medicinal chemistry (Godula, et al., *Science* 312:67-72 (2006); Lyons, et al., *Chem. Rev.* 110: 1147-1169 (2010); Mkhalid, et al., *Chem. Rev.* 110:890-931 (2010); and J. F. Hartwig, *Acc. Chem. Res.* 45:864-873 (2013). Palladium-catalyzed oxidative functionalization of arenes and iridium-catalyzed borylations of arenes are the two classes of arene functionalization reactions most widely used. The palladium-catalyzed oxidative functionalization allows the introduction of a new functional group, usually, at a position ortho to a directing group that can bind to the catalyst (Lyons. et al., *Chem. Rev.* 110:1147-1169 (2010)). The iridium-catalyzed borylation of arenes generates organoboronate esters in which the most sterically accessible C—H bond of an arene is converted to a carbon-boron bond (Mkhalid, et al., *Chem. Rev* 110:890-931 (2010)).

A method to form the carbon-silicon bonds in aryl silanes by C—H silylation would be an important class of arene functionalization. This reaction is important to develop because aryl silane derivatives are monomers for copolymerizations that generate silicone materials, and aryl silanes are synthetic intermediates that undergo oxidation, halogenation, and cross coupling as part of the synthesis of complex organic molecules (Fleming, et al., *Organic Reactions*, A. S. Kende, Ed. (John Wiley & Sons, 1989), Vol. 2, pp. 57-193; Luh, et al., *The Chemistry of Organic Silicon Compounds*, Y. A. Z. Rappoport. Ed. (John Wiley & Sons, Chichester, 2003), vol. 2). Moreover, this reaction is important to develop because it draws parallels to the borylation of arenes but uses simpler, more accessible, and safer reagents and could lead to regioselectivities that complement those of the borylation of arenes.

Much effort has been spent to develop the silylation of arenes, but this reaction has not been used as a synthetic method. Most intermolecular arene silylations were conducted at high temperatures with a large excess of arenes relative to the silane (Ezbiansky, et al., *Organometallics* 17:1455-1457 (1998); Ishiyama, et al., *Angew. Chem. Int. Ed.* 42:5346-5348 (2003); Saiki, et al., *Organometallics* 25:6068-6073 (2006); Murata, et al., *Chem. Lett.* 36:910-911 (2007); Sakakura, et al., *Chem. Lett.* 16:2375-2378 (1987); and Ishikawa, et al., *Organometallics* 11:4135-4139 (1992)), and most arenes that would be used as reagents for synthetic purposes are the more valuable of the two reactants. Some examples were also conducted with disilanes that require a multi-step synthesis (Ishiyama, et al., *Angew. Chem. Int. Ed.* 42:5346-5348 (2003); Saiki, et al., *Organometallics* 25:6068-6073 (2006)). In other cases, triethylsilane has been used as the silicon reagent for the functionalization of arenes and heteroarenes (Ezbiansky, et al., *Organometallics* 17:1455-1457 (1998); Sakakura, et al., *Chem. Lett.* 16:2375-2378 (1987); and Lu, et al., *Angew. Chem. Int. Ed.* 47:7508-7510 (2008)). Although triethylsilane is an inexpensive reagent, the coupling of an arene with a trialkylsilane has limited potentials in addressing synthetic problems because the aryl trialkylsilanes do not undergo oxidation or cross-coupling. For such applications, at least one group that is bound to silicon through a heteroatom or bound to silicon by carbon, but cleavage by fluoride or other additive is needed.

Several groups have reported intramolecular or directed silylation of aryl and alkyl C—H bonds (Ihara. et al., *J. Am. Chem. Soc.* 131:7502-7503 (2009); Kakiuchi, et al., *Chem. Lett.* 30:422-423 (2001); Oyamada, et al., *Angew. Chem. Int. Ed.* 50, 10720-10723 (2011); Williams, et al., *J. Chem. Soc., Chem. Commun.*, 1129-1130 (1995); Ureshino, et al., *J. Am. Chem. Soc.* 132:14324-14326 (2010); Kuninobu, et al., *Org. Lett.* 15:426-428 (2013); Simmons, et al., *J. Am. Chem. Soc.* 132:17092-17095 (2010); Simmons, et al., *Nature* 483:70-73 (2012); and Choi, et al., *J. Am. Chem. Soc.* ASAP, (2013)), a subset of which is beginning to be used in synthetic applications. For example, imines (Williams, et al., *J. Chem. Soc., Chem. Commun.*, 1129-1130 (1995)), pyrazoles (Ihara, et al., *J. Am. Chem. Soc.* 131:7502-7503 (2009)), methoxy (Oyamada, et al. *Angew. Chem. Int. Ed.* 50, 10720-10723 (2011)), and pyridine (Choi, et al., J. Am. Chem. Soc. ASAP (2013)) groups have been shown to bind to platinum, ruthenium, scandium, and iridium catalysts, respectively, to promote silylation ortho to the directing groups. Though the intramolecular silylation of $sp^2$ and $sp^3$ C—H bonds with (hydrido)silyl ether has been demonstrated in the presence of a iridium catalyst (Simmons, et al., *J. Am. Chem. Soc.* 132:17092-17095 (2010); Simmons, et al., *Nature* 483:70-73 (2012)), these catalysts have not led to the intermolecular silylation of arene C—H bonds with the arene as limiting reagent.

A synthetic reaction mixture with components of use to silylate an arene moiety and methods of using such a reaction mixture to form silyl arenes would represent a significant advance in synthesizing silyl arenes. The present invention provides such reaction mixtures and methods.

BRIEF SUMMARY OF THE INVENTION

The present invention provides compositions and methods for silylating functionally diverse arene substrates with a simple liganded metal reagent and a silicon source. In various embodiments, the metal is complexed with a ligand, e.g., a phosphorus-containing ligand. The reaction occurs at low to modest temperatures, allowing the presence of diverse substituents on the arene substrate. In various embodiments, the presence of a directing group on the arene substrate is not required for the reaction to proceed.

In general terms, the invention provides a method for silylation of an arene substrate and compositions of use therein. The invention provides an operationally simple silylation of arene substrates with readily available reagents. This reaction tolerates a range of functional groups, e.g., ether, amine, halogen, alkoxy, and amide, on the arene substrate. The invention also provides reactions utilizing the silylated arene compounds as precursors. In an exemplary embodiment, the invention provides methods of replacing silicon with a halogen. Thus, in an exemplary embodiment, the invention provides compositions and methods for the synthesis of $^{18}$F labeled compounds, which, in an exemplary embodiment, are of use in PET imaging.

Thus, in an exemplary embodiment, there is provided a reaction mixture for silylating an arene substrate. The reaction mixture includes: (i) the arene substrate, which is optionally mono-, di- or tri-substituted; (ii) a silicon source: and (ii) a metal catalyst, wherein the metal catalyst mediates silylating the arene substrate. In an exemplary embodiment, the reaction mixture further includes a hydrogen acceptor. In various embodiments, the reaction mixture includes an organic solvent.

Any useful silicon source can be utilized in the invention. In an exemplary embodiment, the hydrosilane reagent contains one, two or three siloxy groups. Thus, the products are useful intermediates for cross-coupling, oxidation, and halogenation.

Also provided is a method of silylating an arene substrate. The method includes forming a reaction mixture according to the invention and incubating the reaction mixture under conditions appropriate to form a silylated arene compound.

Other embodiments, objects and advantages of the present invention are apparent for the detailed description that follows

BRIEF DESCRIPTION OF THE DRAWINGS

N/A

DETAILED DESCRIPTION OF THE INVENTION

I. Introduction

The ability to selectively silylate an arene substrate has broad application, especially in the agricultural, pharmaceutical, and polymer industries. As described herein, the present invention relates to compositions and methods for transforming an arene substrate to the corresponding silyl compound. The compositions and methods of the invention utilize simple, readily available substrates and reaction mixtures and, thus, have wide applicability.

In various embodiments, the present invention provides a catalytic procedure for the silylation of arene and heteroarene substrates that occurs with readily available and non-hazardous reagents. This reaction tolerates a wide range of substituents. e.g., alkyl, alkoxy, halide, ether, boron-containing groups and haloalkyl functionalities, and occurs in high yield even with ortho-substituted substrates. The simplicity and generality of this method makes it attractive for the introduction of silicon into functionally diverse arene compounds.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are intended to be defined as indicated below.

II. Definitions

As used in this specification and the appended claims, the singular forms "a", "an" and "the" include plural referents unless the content explicitly dictates otherwise. Thus, for example, reference to "cationic nickel catalyst" includes a mixture of two or more such compounds, and the like.

Where substituent groups are specified by their conventional chemical formulae, written from left to right, the structures optionally also encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" or "arene" means, unless otherwise stated, a polyunsaturated, aromatic, substituent that can be a single ring or multiple rings (preferably from 1 to 3 rings), which are fused together or linked covalently. The term "heteroaryl" or "heteroarene" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl." "heteroalkyl," "heteroarene", "aryl". "arene" and "heteroaryl") are meant to optionally include both substituted and unsubstituted forms of the indicated radical. Exemplary substituents for each type of radical are provided below. The discussion regarding aryl and heteroaryl radicals is relevant to embodiments in which an arene or heteroarene is the substrate.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'". —OC(O)R', —C(O)R'. —CO$_2$R', —CONR'R", —OC(O)NR'R", —NR"C(O)R', —NR'—C(O)NR'R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl and heteroaryl groups and arene and heteroarene substrates are generically referred to as "aryl group substituents." The substituents are selected from, for example: H, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR'R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl. These terms encompass groups considered exemplary "aryl group substituents", which are components of exemplary "substituted aryl" and "substituted heteroaryl" moieties.

As used herein, the term "acyl" describes a substituent containing a carbonyl residue. C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si), phosphorus (P), and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "ligand" has the meaning ordinarily ascribed to it in the art. Exemplary ligands include at least one donor atom capable of binding to a transition metal. Ligands can include sterically bulky species, such as substituted or unsubstituted aryl, substituted or unsubstituted heteroaryl and substituted or unsubstituted fused ring systems, secondary and tertiary alkyl groups and the like. As described below, a ligand of use in the invention can be conceptualized as including a linker joining two or more donor atoms, which are the same or different atoms.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers and d and l isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The compounds disclosed herein may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

A "directing group", as this term is used herein refers to an "aryl group substituent", which causes a reaction to occur at a position ortho to the directing group. Examples of these groups include —OMe, C(O)NR$_2$, 2-pyridyl, and —C(NR)R. These groups typically bond to the metal catalyst or metal of a basic reagent, such as BuLi, causing the reaction to occur at the position ortho to this group.

Below are examples of specific embodiments for carrying out the present invention. The examples are offered for illustrative purposes only, and are not intended to limit the scope of the present invention in any way.

III. The Compositions

In various embodiments, there is provided a reaction mixture for silylating a substituted aryl compound. The reaction mixture includes: (i) the substituted arene substrate; (ii) a silicon source; and (ii) a metal catalyst (e.g., Ir or Rh). The metal ion source mediates silylation of the arene substrate. In various embodiments, the composition further comprises an organic solvent.

An exemplary arene substrate is substituted with one or more "aryl group substituents" as this term is defined herein. In an exemplary embodiment, the substrate is di-substituted in a 1, 2 or 1,3, or 1,4-pattern. In various embodiments, the substrate is a fused ring system including two or more arene rings, two or more heteroarene rings or a combination of arene and heteroarene rings.

In various embodiments, the substrate has the formula:

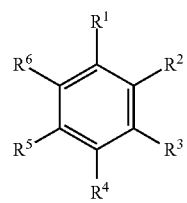

wherein $R^1$, $R^2$, $R^1$, $R^4$, $R^5$, and $R^6$ are independently members selected from H, substituted or unsubstituted alkyl, substituted or unsubstituted heteroalkyl, substituted or unsubstituted aryl, substituted or unsubstituted heteroaryl, halogen, BR$^7$R$^8$, CN, CF$_3$, acyl, —SO$_2$NR$^7$R$^8$, —NR$^7$R$^8$, —OR$^7$, —S(O)$_2$R$^7$, —C(O)R$^7$, —COOR$^7$, —CONR$^7$R$^8$, —S(O)$_2$OR$^7$, —OC(O)R$^7$, —C(O)NR'R$^8$, —NR$^7$C(O)R$^8$, —NR$^7$SO$_2$R$^8$ and —NO$_2$. Optionally, two or more of R$^1$, R$^2$, R$^3$, R$^4$, R$^5$, R$^6$, R$^7$ and R$^8$, together with the atoms to which they are bonded, are joined to form a ring system which is a member selected from substituted or unsubstituted cycloalkyl, substituted or unsubstituted heterocycloalkyl, substituted or unsubstituted aryl and substituted or unsubstituted heteroaryl.

R$^7$ and R$^8$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. Optionally, R$^7$ and R$^8$, together with the atoms to which they are bonded, are joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

The silicon source is any silicon source useful to provide a reactive species under the conditions of the reaction of the present invention. In various embodiments, the silicon source is a hydrosilane. An exemplary hydrosilane of use in the invention is one bearing one, two or more heteroatom(s). An exemplary silicon source of use in the present invention has the formula:

(1)

in which $R^s$, $R^t$ and $R^u$ are independently selected from H, substituted or unsubstituted alkyl, substituted or unsubstituted heteroalkyl and XR$^x$, in which R$^x$ is H or substituted or unsubstituted alkyl, substituted or unsubstituted aryl or substituted silyl, and X is a heteroatom, e.g, O, Si. In an exemplary embodiment, one or two or three of R$^s$, R$^t$ and R$^u$ is OR$^x$. In these cases, the R$^s$, R$^t$ and R$^u$ groups, which is (are) not OR$^x$ is (are) independently selected from an alkyl, aryl, or silyl group. Two or more OR$^x$ groups can be linked to each other by a carbon chain. In another embodiment, one or two or three of R$^s$, R$^t$ and R$^u$ is a halogen, e.g., fluoride. In this compound according to Formula I, the R$^s$, R$^t$ and R$^u$ which is (are) not a halogen, is (are) independently selected from an alkyl, alkoxy, aryl, silyl or silyloxy groups.

In an exemplary embodiment, the silicon source includes at least one group bound to the silicon atom which is other than an alkyl group or a hydrogen, e.g., the silicon source is not HSiR$_3$, in which R is alkyl. In an exemplary embodiment, the silicon source includes at least one heteroatom bound to a silicon atom of the silicon source, e.g., the silicon source is HSiR(X—(X')$_n$R$^x$$_m$)$_2$, in which X and X' are independently selected heteroatoms, the index m is 1, 2, or 3, n is 0 or 1, and R and R$^x$ are independently selected from substituted or unsubstituted alkyl, substituted and unsubstituted aryl. In an exemplary embodiment X is O. In an exemplary embodiment, X' is Si. In an exemplary embodiment, R and R' are selected from C$_1$-C$_6$ alkyl, which, other than the bond joining it to the remainder of the molecule is otherwise unsubstituted. An exemplary silicon source according to this embodiment is $HSiMe(OSiMe_3)_2$.

In an exemplary embodiment, the reaction includes the silicon source in a molar ratio of less than 10:1 to the substrate, e.g., arene. In various embodiments, the silicon source is a silane having at least one heteroatom and is in a molar ratio with the substrate of less than 10:1. In an exemplary embodiment, the silicon source is a hydrosilane having at least one heteroatom and is in a molar ratio with the substrate of less than 10:1. In an exemplary embodiment, the silicon source is a silane having at least one heteroatom and is in a molar ratio with the substrate of less than 10:1. In various embodiments, the silicon source is a hydrosilane having at least one heteroatom and is in a molar ratio with the substrate of less than 10:1, and the metal atom is selected from Ir and Rh. In an exemplary embodiment, the silicon source is a silane having at least one heteroatom and is in a molar ratio with the substrate of less than 10:1, and the substrate is not substituted with a directing group In an exemplary embodiment, when the moiety on the substrate undergoing silylation ("silylatable moiety") is a five membered heteroarene or heteroaryl ring, the silicon source is as described in the paragraph above. In various embodiments, when the moiety on the substrate undergoing silylation is a five-membered heteroarene or heteroaryl ring including a single heteroatom selected from N, S and O, the silicon source is as described in the paragraph above. In various embodiments, when the moiety on the substrate undergoing silylation is a five-membered nitrogen-, oxygen-, or sulfur containing heteroarene or heteroaryl ring, the silicon source is as described in the paragraph above. In various embodiments, when the moiety on the substrate undergoing silylation is an arene or aryl ring, or a heteroarene or a heteroaryl ring other than a five-membered heteroarene or heteroaryl ring including one or more heteroatoms selected from N, S and O, the silicon source has essentially any useful structure, e.g., a silicon source according to Formula I.

In an exemplary embodiment, when the moiety on the substrate undergoing silylation is a five-membered nitrogen-containing heteroaryl ring, the silicon source includes at least one group bound to the silicon atom which is other than an alkyl group or a hydrogen, e.g., the silicon source is not $HSiR_3$, in which R is alkyl.

In an exemplary embodiment, the reaction mixture also includes a hydrogen acceptor. Exemplary hydrogen acceptors are alkenes, e.g., cycloalkenes, e.g., cyclohexene or norbornene or are hindered alkenes, e.g. tert-butyl ethylene.

As noted above, the reaction mixture and the reactions of the invention include a metal atom supported by one or more ligand, e.g., a phosphine ligand. In exemplary embodiments, a ligand of use in the present compositions is a multidentate ligand, including 2, 3, 4 or more donor atoms. In various compounds of the invention, the ligand is rigid (e.g., a ring structure) and is robust under a variety of chemical conditions (e.g., those utilized for hydrosilylation of pi-bonded organic substrates). Exemplary ligands include one or more moiety on which the pattern of substitution and/or the nature of the substituents is readily varied (e.g., an aryl or heteroaryl moiety), which allows for the facile modification of the electronic properties of the ligand and provides a route to tune the electronic properties of the compositions of the invention to induce, optimize, minimize or prevent a particular type of reaction mediated by the composition of the invention. Furthermore, the ease of engineering a composition of the invention allows for the design of a catalyst that functions optimally with a selected substrate or class of substrates (e.g., primary, secondary or tertiary hydrosilanes, substituted or unsubstituted alkenes, substituted or unsubstituted alkynes, carbonyl-containing compounds and the like).

In an exemplary embodiment, the ligand is a biaryl ligand with two coordinating phosphorus atoms.

In various embodiments, the phosphine ligand of use in the invention has the formula:

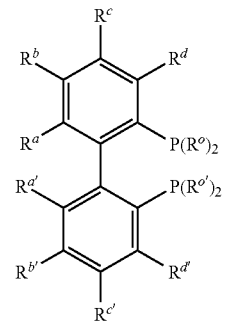

in which $R^a$, $R^b$, $R^c$, $R^d$, $R^o$, $R^{a'}$, $R^{b'}$, $R^{c'}$, $R^{d'}$, and $R^{o'}$, are each members independently selected from those moieties referred to herein as "aryl group substituents".

In various embodiments, $R^a$, $R^b$, $R^c$, $R^d$, $R^{a'}$, $R^{b'}$, $R^{c'}$, and $R^{d'}$ are each members independently selected from H, substituted or unsubstituted alkyl, substituted or unsubstituted heteroalkyl, halogen, CN, $CF_3$, acyl, $-SO_2NR^eR^f$, $-NR^eR^f$, $-OR^e$, $-S(O)_2R^e$, $-C(O)R^e$, $-COOR^e$, $-CONR^eR^f$, $-S(O)_2OR^e$, $-OC(O)R^e$, $-C(O)NR^eR^f$, $-NR^eC(O)R^f$, $-NR^eSO_2R^f$ and $-NO_2$, wherein two or more of $R^a$, $R^b$, $R^c$, $R^d$, $R^e$, $R^f$, $R^{a'}$, $R^{b'}$, $R^{c'}$, and $R^{d'}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

Exemplary moieties for $R^e$ and $R^f$ include members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^e$ and $R^f$, together with the atoms to which they are bonded, are optionally joined to form a 5- to 7-membered ring.

In various embodiments, each $R^o$ and $R^{o'}$ is an independently selected substituted or unsubstituted alkyl, substituted or unsubstituted heteroalkyl moiety, a substituted or unsubstituted aryl or a substituted or unsubstituted heteroaryl moiety (e.g., a substituted or unsubstituted aryloxy or heteroaryloxy moiety). In various embodiments. Ro and Ro are independently selected from alkoxo, amino and silyl groups.

The composition and method of the invention is exemplified herein by reference to species in which the ligand is a phosphorus-containing ligand, e.g., phosphine, or phosphinyl ligand. In an exemplary embodiment, a phosphorus atom of the ligand is a donor atom for the metal species, e.g., Ir, Rh. Exemplary ligands include both a donor phosphorus atom and a donor nitrogen atom. Those of skill in the art will recognize that this focus is for clarity of illustration and other ligands have utility as well.

Phosphorus-containing ligands are ubiquitous ligands in catalysis and are used for a number of commercially important chemical transformations. Phosphorus-containing ligands commonly encountered in catalysis include phosphines and phosphites. Monophosphine and monophosphite ligands are compounds that contain a single phosphorus atom that serves as a donor to a metal. Bisphosphine, bisphosphite, and bis(phosphorus) ligands in general, contain two phosphorus donor atoms and normally form cyclic chelate structures with transition metals.

There is a wealth of information in the art regarding the preparation of phosphorus-containing ligands, their coordination to various metal centers and the properties of the resulting compounds. Many of these ligands are of use the compounds of the present invention.

Other exemplary art-recognized phosphorus-containing ligands of use in the present invention include substituted and unsubstituted bis(8-quinolyl)(3,5-di-tert-butylphenoxy)phosphine, (R)-(−)-1-[(S)-2-diphenylphosphino)ferrocenyl]ethyldi-tert-butylphosphine; [(4R)-[4,4'-bi-1,3-benzodioxole]-5,5'-diyl]bis[bis[3,5-bis(1,1-dimethylethyl)-4-methoxyphenyl]-phosphine; and (R)-(−)-1-(6,6-dimethoxybiphenyl-2,2'-diyl)bis(3,5-dimethylphenyl)phosphine); and combinations thereof. Specific examples of the chiral ligand include cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis(substituted phospholano)benzene (DuPHOS), 1,2-bis(substituted phospholano)ethane(BPE), 1-(substituted phospholano)-2-(diphenylphosphino)benzene (UCAP-Ph), 1-[bis(3,5-dimethylphenyl)phosphino]-2-(substituted phospholano)benzene (UCAP-DM), 1-(substituted phospholano)-2-[bis(3,5-di(t-butyl)-4-methoxyphenyl)phosphino]benzene (UCAP-DTBM), 1-(substituted phospholano)-2-(di-naphthalen-1-yl-phosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octahydrobinaphthyl)(H$_8$-BINAP), 2,2'-bis(di-p-tolylphosphino)-1,1'-binaphthyl (TOL-BINAP), 2,2'-bis[di(3,5-dimethylphenyl)phosphino]-1, 1'-binaphthyl (DM-BINAP), 2,2'-bis(diphenylphosphino)-6,6'-dimethyl-1-1'-biphenyl (BICHEP), [4,4'-bi-1,3-benzodioxole]-5,5'-diylbis[diphenylphosphine] (SEGPHOS), [4,4'-bi-1,3-benzodioxole]-5,5'-diylbis[bis(3,5-dimethylphenyl)phosphine] (DM-SEGPHOS), [(4S)-[4,4'-bi-1,3-benzodioxole]-5,5'-diyl]bis[bis[3,5,-bis(1,1-dimethylethyl)-4-methoxyphenyl]phosphine] (DTBM-SEGPHOS), etc.

In various embodiments, a ligand in a compound of the invention is a phosphinite, phosphonite or phosphite ligand. This ligand is bound to a metal atom, e.g., Rh or Ir. Similar to phosphine ligands, phosphinite, phosphonite and phosphites have recently emerged as versatile ligands in transition metal catalyzed reactions. Positioning of electronegative groups and heteroatoms such as N and O (but not limited thereto) allow subtle modulation of electronic properties of these ligands that are often beneficial to catalytic reactions. The presence of adjacent O and N provides additional oxidative stabilities to these ligands compared to their phosphine analogues. These ligands are easy to make in high yield due to availability of large natural and synthetic chiral pool derived amino alcohols and chiral diols (for a modular approach, see Velder, J.; Robert, T.; Weidner, I.; Neudorfl, J.-M.; Lex, J.; Schmalz, H-G. *Adv. Synth. Catal.* 2008, 350, 1309-1315: for a review on synthesis of phosphites, see Montserrat Diéguez, Oscar Pimies, Aurora Ruiz, and Carmen Claver, *Methodologies in Asymmetric Catalysis*, Chapter 11, 2004, pp 161-173 ACS *Symposium Series*, Volume 880 for synthesis of phosphites. See Adriaan J. Minnaard, Ben L. Feringa, Laurent Lefort and Johannes G. de Vries *Acc. Chem. Res.*, 2007, 40 (12), pp 1267-1277 for the synthesis of phosphoramidites).

Examples where phosphinite ligands have been used as ligands for metal-based catalysts include Blankenstein, J.; Pflatz. A. *Angew Chem. Int. Ed.*, 2001, 40, 4445-47) and Pd catalyzed Suzuki cross coupling reaction (Punji, B.; Mague, J. T.; Balakrishna. M. S. *Dalton Trans.*, 2006, 1322-1330), Braunstein, P.; Naud, F.; Pflatz, A.; Rettig, S. *Organometallics*, 2000, 19, 2676-2683), Martorell, A.; Naasz, R.; Ferringa, B. L.; Pringle, P. G. *Tetrahedron Asymmetry*, 2001, 12, 2497-2499 and Peng. X.; Wang, Z.; Xia, C.; Ding, K. *Tetrahedron Lett.*, 2008, 49, 4862-4864)

Rajanbabu and coworkers have prepared nickel compounds supported on phosphinite, phosphite and phosphoramidite ligands and have used these catalysts for asymmetric hydrovinylation reactions (Park, H.; Kumareswaran. R.; Rajanbabu, T. V. R. *Tetrahedron*, 2005, 61, 6352-67). Sandoval et al., have used Rh(T) diphosphite ligands for asymmetric hydrogenation of dehydroamino acid derivatives (Sandoval, C. A.; Liu, S. *J. Molecular. Catalysis. A*, 2010, 325, 65-72). Pd phosphite catalyzed dehalogenation of arenes was reported by Lee et al., (Moon, J.; Lee, S. *J. Organometal. Chem.*, 2009, 694, 473-77). Pd-triphenyl phosphite was shown to catalyze dehydrative allylation using allyl alcohol (Kayaki, Y.; Koda, T.; Ikariya, T. *J. Org. Chem.*, 2004, 69, 2595-97). Pd-based biaryl phosphite catalyst is known to be effective in asymmetric allylic substitution reactions of allyl acetate, carbonate and halides (Dieguez, M.; Pamies, O. *Ace. Chem. Res.*, 2010, 43, 312-22). Calixarene phosphites have been used as hemispherical chelator ligands for obtaining high linear to branched ratio of olefin in Rh(0) catalyzed hydroformylation reaction (Monnereau. L.; Semeril, D.; Matt, D.; Toupet, L. *Adv. Synth. Catal.* 2009, 351, 1629-36).

In various embodiments, the ligand in the compound of the invention is a phosphoramidite ligand. Phosphoramidite ligands have been used in catalytic asymmetric hydrogenations (Minnaard, A. J.; Feringa, B. L.; Lefort, L.; de Vries, J. G. *Ace. Chem. Res.*, 2007, 40, 1267-77), conjugate addition to enones (Jagt, R. B. C.; de Vries, J. G.; Ferringa, B. L.; Minnaard, A. J. *Org. Lett.*, 2005, 7, 2433-35), and allylic alkylation with diethyl zinc (Malda, H.; van Zijl, A. W.; Arnold, L. A.; Feringa, B. L. *Org. Lett.*, 2001, 3, 1169-1171).

Any metal atom useful to accomplish the dehydrogenative coupling of arenes with silanes to form aryl silanes is of use in the present invention. In an exemplary embodiment, the metal atom is Rh or Ir. In various embodiments, the metal is selected from Pt, Fe, Ru, Os, Mn, and Re.

In various embodiments, the ligand is a substituted or unsubstituted phenanthroline, such as:

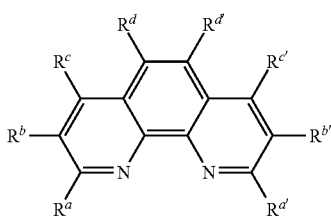

in which $R^a$, $R^b$, $R^c$, $R^d$, $R^{a'}$, $R^{b'}$, $R^{c'}$ and $R^{d'}$ are as defined above. In an exemplary embodiment, the ligand is a phenanthroline and the metal is Ir.

In various embodiments, the ligand is a bipyridine. An exemplary bipyridine is:

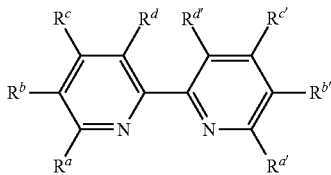

in which $R^a$, $R^b$, $R^c$, $R^d$, $R^{a'}$, $R^{b'}$, $R^{c'}$ and $R^{d'}$ are as defined above. In an exemplary embodiment, the ligand is a bipyridine and the metal is Ir.

The metal atom can be introduced to the reaction mixture complexed with the ligand or the metal-ligand complex can be formed in situ. In this latter embodiment, the substrate is preferably added after the formation of the complex, though this is not essential.

The components can be combined in any useful amount and proportion. In an exemplary embodiment, the reaction mixture is proportioned such that the arene substrate is the limiting reagent. In an exemplary embodiment, the reaction mixture includes a 1:2 ratio of arene to silicon source.

The invention also provides a reaction mixture as set forth above further containing a product of the reaction selected. An exemplary product is one in which the silicon atom is attached to the intra-annular carbon atom at the least sterically hindered site on the arene. In various embodiments, the product is derived from silylation of a 1,3-disubstituted arene.

In other embodiments, the product of the reaction that includes both the silyl substituent and $BR^7R^8$.

IV. The Methods

Also provided is a method of utilizing such a reaction mixture to prepare a silyl arene compound. In general terms, the method includes incubating the reaction mixture under conditions sufficient to form the silyl arene.

The method of the invention leads to the coupling of arenes with silanes to form aryl silanes in high yields. In an exemplary embodiment, the method is performed with a ratio of arene to silane between 2:1 and 1:3 with an arene lacking a group to direct the silylation at an ortho position. In various embodiments, the reactions occur with remarkably high selectivities at the most sterically accessible C—H bond of 1,3-disubstituted arenes. In various embodiments, the method of the invention proceeds with 1,2 and 1,4-substituted arenes with selectivities that are higher that those achieved from the borylation of the same substrates, which provides a statistical mixtures of products.

In an exemplary embodiment, the coupling is a dehydrogenative coupling.

In a further exemplary embodiment, the method of the invention leads to the coupling, e.g., the dehydrogenative coupling, of arenes with hydrosilanes with a ratio of arene to silane between 2:1 and 1:3. In an exemplary embodiment, the arene substrate lacks a group to direct the silylation at an ortho position. A preferred method of the invention forms silyl arenes in high yields, e.g., at least 40%.

In a further exemplary embodiment, the method of the invention leads to the dehydrogenative coupling of arenes lacking a group to direct the silylation at an ortho position with hydrosilanes in which the hydrosilane contains one or more silicon-heteroatom bonds and a rhodium catalyst to form aryl silanes in high yields.

In an exemplary embodiment, the method of the invention provides a method for a transformation orthogonal to the transformation of arylboron derivatives, and this orthogonality allows C—H silylation and borylation to generate intermediates that can be derivatized sequentially to form a variety of arenes with substitution patterns difficult to access by classical electrophilic aromatic substitution or the more recently developed C—H bond oxidation or borylation alone.

In various embodiments, the product of the reaction includes both the silyl moiety and $BR^7R^8$. In an exemplary embodiment, one or both of these groups is replaced with another moiety in a reaction subsequent to the reaction forming the product. In a further exemplary embodiment, functional group interconversions are conducted at other parts of the molecule after formation of the aryl silane and prior to transformation of the carbon-silicon bond to a carbon-carbon or carbon-heteroatom bond. The following examples are offered to illustrate exemplary embodiments of the invention, are not to be construed as limiting the invention.

EXAMPLES

Example 1

General Comments

All air-sensitive manipulations were conducted under an inert atmosphere in a nitrogen-filled glovebox. Tetrahydrofuran, benzene, and toluene were dried with an Innovative Technology Pure-Solv solvent purification system. Reagents were purchased from commercial sources unless otherwise indicated and degassed prior to use. [Ir(cod)OMe]$_2$ was obtained from Johnson-Matthey. 2-Methylphenanthroline (2-MePhen) (Poole, et al., *Org. Biomol. Chem.* 3:1013-1024 (2005)), [Rh(coe)$_2$Cl]$_2$ (Ent, et al., *Inorg. Synth.* 27:90-92 (1990)), [Rh(C$_2$H$_4$)$_2$Cl]$_2$ (R. Cramer, *Inorg. Synth.* 15:14-18 (1974)). [Rh(coe)$_2$OH]$_2$ (Werner, et al., *J. Chem. Soc., Dalton Trans.*, 3549-3558 (1998)), tert-butyldimethyl(m-tolyloxy)silane (7a) (Watahiki, et al., *Green Chem.* 5:82-84 (2003)), 4'-methoxy-3-methyl-1,1'-biphenyl (17a) (Cheng, et al., *Tetrahedron Lett.* 44:7095-7098 (2003)), N,N-diethyl-2-methylbenzamide (33a) (Buswell, et al., *Org. Biomol. Chem.* 2:3006-3017 (2004)), and 2-triisopropylsilyloxyanisole (26a) (Shashack, et al., *ACS Chem. Neurosci.* 2:640-644 (2011)) were synthesized according to the literature procedures. [Ir(cod)OMe]2,1 2-methyl-1,10-phenanthroline (L1), 2,2-tert-butyl-1,10-phenathroline (L9), 3 2-methoxy-1,10-phenathroline (L7) (Krapcho et al., S., *J. Heterocyclic Chem.* 2008, 45, 1167-1170.), and L10 (Ishikawa et al., *Synthesis* 2005, 13, 2176-2182) were synthesized according to literature procedures. 2-Ethyl-1,10-phenanthroline was synthesized according to the procedure for L12 using EtLi instead of MeLi, and the NMR data match the literature data.

Chen et al., *Chem. Commun.* 2012, 48, 2906-2908. Duloxetine, chlopidogrel, ketotifen, clonidine, bupropion, and palonosetron were purchased as the corresponding ammonium salts and neutralized with $K_2CO_3$.

GC analyses were conducted on an HP 6890 GC equipped with an HP-5 column (25 m×0.20 mm ID×0.33 m film) and an FID detector. GC yields were calculated using dodecane as the internal standard. HPLC analyses were conducted on a Waters chromatography system (1525 binary pump, 717+ autosampler, 2487 dual wavelength detector) with using chiral stationary columns (0.46 cm×25 cm) from Daicel. High-resolution mass spectra were obtained via the Micro-Mass/Analytical Facility operated by the College of Chemistry, University of California, Berkeley. NMR spectra were acquired on Bruker AVB-400, DRX 500, and AV-600 spectrometers. Chemical shifts were reported in ppm relative to residual solvent peaks ($CDCl_3$=7.26 ppm for $^1H$ and 77.16 ppm for $^{13}C$). Coupling constants were reported in Hz. Flash column chromatography was performed on a Teledyne ISCO CombiFlash® Rf system. Products were visualized on TLC plates under 254 nm UV light or by staining with $I_2$.

Synthesis of Substrates

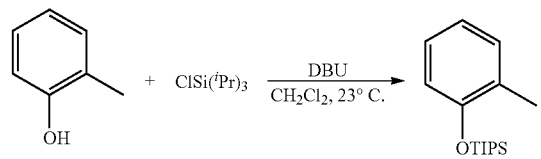

2-Triisopropylsiloxytoluene (25a): To a solution of $ClSi(^iPr)_3$ (1.93 g, 10.0 mmol) and 1,8-diazabicyclo[5.4.0]undec-7-ene (1.52 g, 10.0 mmol) in dry $CH_2Cl_2$ (10 mL) was added slowly o-cresol (1.10 g, 10.2 mmol), and the reaction was stirred at 23° C. for 14 h. The reaction was then quenched with water (10 mL), washed with saturated aqueous $NaHCO_3$, and the organic layer was separated, dried over $MgSO_4$, and the solvent was evaporated in vacuo. The residue was purified by column chromatography on silica (0→920% ethyl acetate in hexanes) to afford the product as a colorless liquid (1.14 g, 43% yield). $^1H$ NMR (600 MHz, $CDCl_3$) δ 7.13 (d, J=7.3 Hz, 1H), 7.04 (t, J=7.5 Hz, 1H), 6.84 (t, J=7.4 Hz, 1H), 6.79 (d, J=8.0 Hz, 1H), 2.25 (s, 3H), 1.36-1.26 (m, 3H), 1.13 (d, J=7.5 Hz, 18H). $^{13}C$ NMR (151 MHz, $CDCl_3$) δ 154.45 (s), 131.01 (s), 128.70 (s), 126.68 (s), 120.73 (s), 118.09 (s), 18.20 (s), 17.17 (s), 13.18 (s). GC-MS (EI+): 264 (M), 221 (M-$^iPr$).

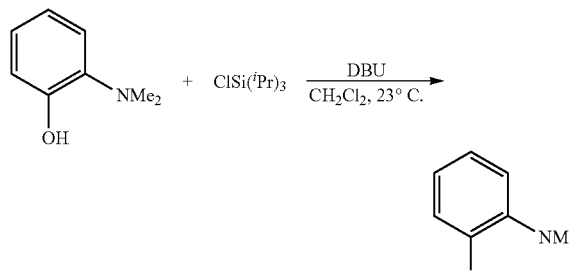

2-Triisopropylsiloxy-N,N-dimethylaniline (27a): Following a procedure similar to the one for the synthesis of 25a starting from N,N-dimethylaminophenol (Wang, et al., *J. Org. Chem.* 73:8639-8642 (2008)) (223 mg, 1.63 mmol), the product was obtained as a colorless liquid (265 mg, 55% yield). $^1H$ NMR (600 MHz, $CDCl_3$) δ 6.93-6.86 (m, 2H), 6.86-6.79 (m, 2H), 2.76 (s, 6H), 1.35-1.25 (m, 3H), 1.12 (d, J=7.5 Hz, 18H). $^{13}C$ NMR (151 MHz. $CDCl_3$) δ 149.13 (s), 144.99 (s), 121.78 (s), 121.48 (s), 120.09 (s), 118.50 (s), 43.25 (s), 18.11 (s), 13.16 (s). GC-MS (EI+): 293 (M), 250 (M-$^iPr$).

Evaluation of Reaction Conditions for the Silylation of Arenes

Reactions were conducted on a 0.05 mmol scale. In a nitrogen-atmosphere glovebox, the metal precursor, the ligand, the solvent (THF), the silane, the hydrogen acceptor, and the substrate were combined, in this order, in a 4-mL glass vial equipped with a magnetic stirrer. The vial was sealed with a Teflon-lined cap, and the contents were stirred at room temperature for 15 min and then at the desired temperature for 16 h. The yields were determined by GC.

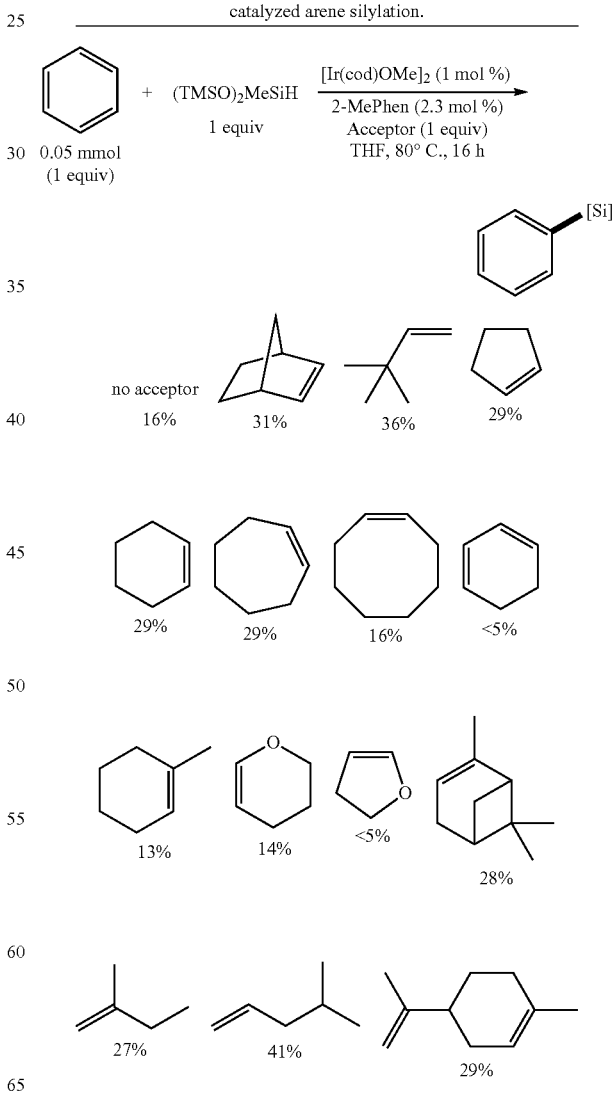

Chart 1. Effect of hydrogen acceptor on the yields of the iridium-catalyzed arene silylation.

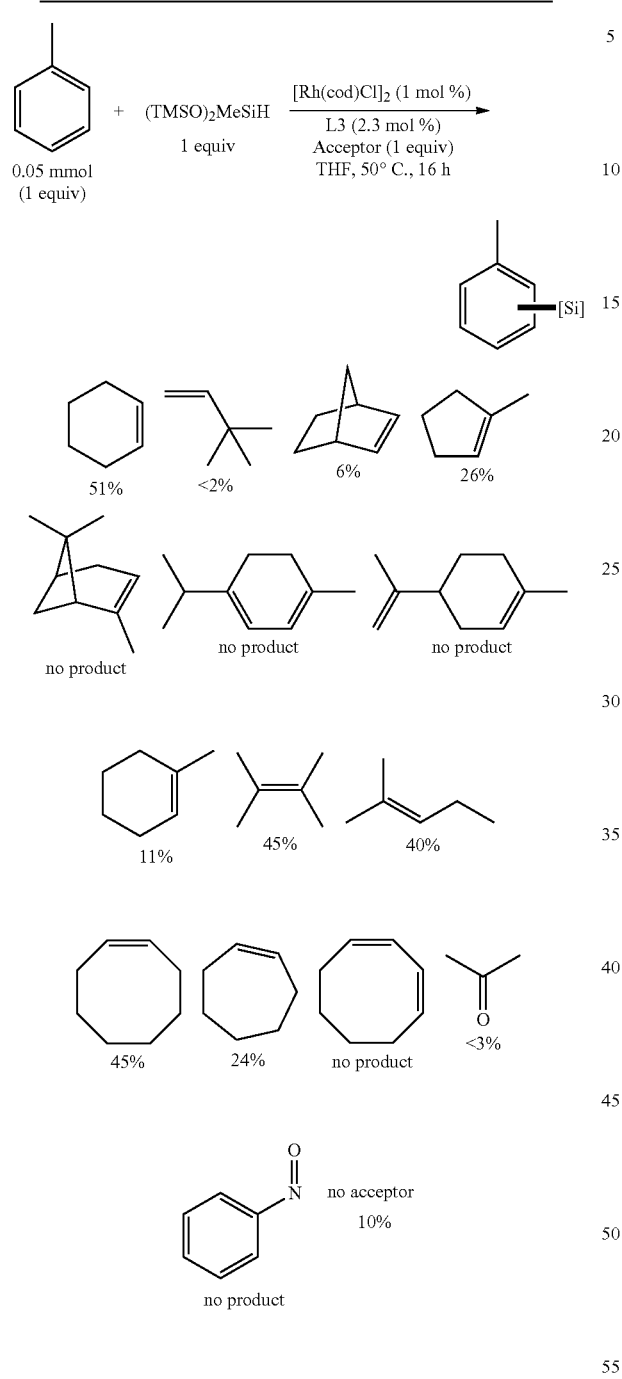

Chart 2. Effect of hydrogen acceptor on the yields of the rhodium-catalyzed arene silylation.

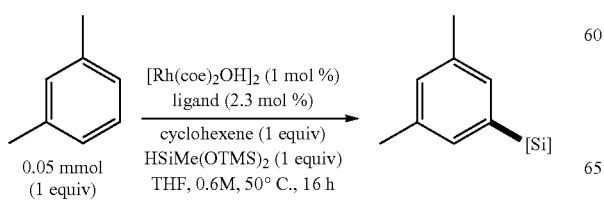

Chart 3. Effect of ligand structure on the yields of the rhodium-catalyzed arene silylation.

-continued

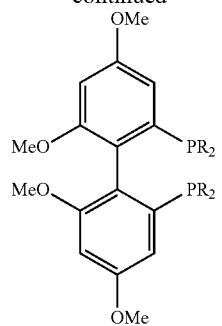

Garphos
R = -3,5-(CF$_3$)$_2$—Ph
38%
R = DTBM
81%
R = -3,5-Me$_2$—Ph
83%
R = -3,5-Me$_2$-4-MeO—Ph
54%

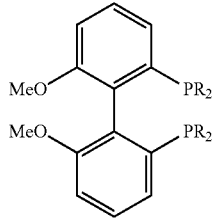

MeO—BIPHEP
R = DTBM (L1)
79%
R = 2-furyl
no product
R = -3,4,5-(MeO)$_3$—Ph
(L2) 87%
R = -3,5-iPr$_2$-4-NMe$_2$—Ph
26%

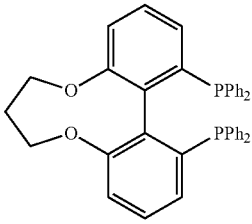

C3-Tunephos
no product

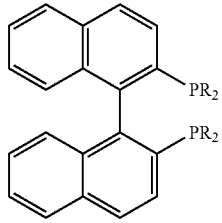

BINAP
R = -4-Me—Ph
21%
R = -3,5-Me$_2$—Ph
70%
R = DTBM
7%

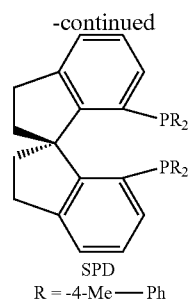

SPD
R = -4-Me—Ph
no product
R = -3,5-Me₂—Ph
no product

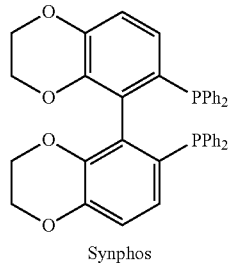

Synphos
8%

DTBM = 3,5-(ᵗBu)₂-4-MeO—Ph

Typical Procedure for the Silylation of Arenes

In a nitrogen-atmosphere glovebox, (TMSO)₂MeSiH (133 mg, 0.600 mmol) was added to a solution of [Rh(coe)₂OH]₂ (2.0 mg, 3.0 µmol) and L2 (6.2 mg, 6.6 µmol) in THF (200 mg), and the mixture was stirred at 23° C. for 5 min. To the mixture was then added cyclohexene (49 mg, 0.60 mmol) and the arene (0.30 mmol), and the reaction mixture was stirred at 23° C. for 15 min and then at 45° C. The reaction progress was monitor by GC. After complete conversion of the silane (usually within 16 h), the volatile materials were evaporated in vacuo, and the residue was purified by flash column chromatography on silica to give the arylsilane product.

The general procedure was followed with 1,3-dimethoxybenzene (68.1 mg, 0.493 mmol). The product was obtained as a colorless liquid (160 mg, 89% yield). ¹H NMR (500 MHz, CDCl₃) δ 6.75 (d, J=2.2 Hz, 2H), 6.52 (t, J=2.0 Hz, 1H), 3.83 (s, 6H), 0.30 (s, 3H), 0.17 (s, 18H). ¹³C NMR (126 MHz, CDCl₃) δ 160.44 (s), 140.90 (s), 110.76 (s), 101.67 (s), 55.26 (s), 1.99 (s), 0.12 (s). HRMS (EI+) calcd for [C₁₅H₃₀O₄Si₃]: 358.1452, found: 358.1461.

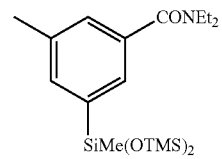

The general procedure was followed with N,N-diethyl-3-methylbenzamide (58.8 mg, 0.307 mmol). The product was obtained as a colorless liquid (121 mg, 96% yield). ¹H NMR (500 MHz. CDCl₃) δ 7.34 (s, 1H), 7.29 (s, 1H), 7.17 (s, 1H), 3.52 (bs, 2H), 3.21 (bs, 2H), 2.34 (s, 3H), 1.22 (bs, 3H), 1.07 (bs, 3H), 0.23 (s, 3H), 0.08 (s, 18H). ¹³C NMR (126 MHz, CDCl₃) δ 171.87 (s), 138.61 (s), 137.23 (s), 136.53 (s), 134.65 (s), 128.13 (s), 127.81 (s), 43.26 (s), 39.12 (s), 21.45 (s), 14.28 (s), 12.95 (s), 1.91 (s), 0.06 (s). HRMS (EI+) calcd for [C₁₉H₃₇NO₃Si₃]: 411.2081, found: 411.2065.

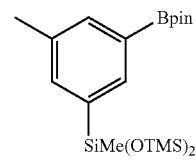

The general procedure was followed with 4,4,5,5-tetramethyl-2-(m-tolyl)-1,3,2-dioxaborolane (442 mg, 2.03 mmol). After the reaction has completed, the solvent was evaporated, and the residue was suspended in hexanes. The mixture was filtered over celite, and filtrate was concentrated. The residue was then purified by flash column chromatography to give the product as a colorless liquid (851 mg, 96% yield). ¹H NMR (500 MHz, CDCl₃) δ 7.86 (s, 1H), 7.68 (s, 1H), 7.49 (s, 1H), 2.39 (s, 3H), 1.37 (s, 12H), 0.31 (s, 3H), 0.15 (s, 18H). ¹³C NMR (126 MHz, CDCl₃) δ 137.63 (s), 137.20 (s), 137.03 (s), 136.56 (s), 136.08 (s), 83.72 (s), 25.00 (s), 21.49 (s), 2.03 (s), 0.35 (s). ¹¹B NMR (128 MHz, CDCl₃) δ 30.35 (bs). HRMS (EI+) calcd for [C₂₀H₉BO₄Si₃]: 438.2249, found: 438.2250.

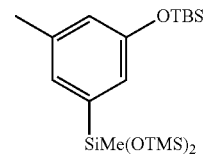

The general procedure was followed with tert-butyldimethyl(m-tolyloxy)silane (67.8 mg, 0.304 mmol), The product was obtained as a colorless liquid (91 mg, 67% yield). ¹H NMR (500 MHz, CDCl₃) δ 6.97 (s, 1H), 6.86 (s, 1H), 6.71 (s, 1H), 2.33 (s, 3H), 1.02 (s, 9H), 0.27 (s, 3H), 0.22 (s, 6H), 0.14 (s, 18H). ¹³C NMR (126 MHz, CDCl₃) δ 155.12 (s), 139.80 (s), 138.76 (s), 127.10 (s), 122.27 (s), 121.68 (s), 25.88 (s), 21.53 (s), 18.37 (s), 2.03 (s), 0.18 (s), —4.22 (s). HRMS (EI+) calcd for [C₂₀H₄₂O₃Si₄]: 442.2211, found: 442.2207.

The general procedure was followed with N,N,3-trimethylaniline (43.3 mg, 0.320 mmol). The product was obtained as a colorless liquid, 74 mg, 65% yield. ¹H NMR (500 MHz, CDCl₃) δ 6.83 (s, 1H), 6.79 (s, 1H), 6.64 (s, 1H), 2.98 (s, 6H), 2.37 (s, 3H), 0.29 (s, 3H), 0.17 (s, 18H). ¹³C NMR (126

MHz, CDCl$_3$) δ 150.14 (s), 138.94 (s), 137.89 (s), 122.89 (s), 114.99 (s), 114.95 (s), 40.92 (s), 22.04 (s), 2.07 (s), 0.41 (s). HRMS (EI+) calcd for [C$_{16}$H$_{33}$NO$_2$Si$_3$]: 355.1819, found: 355.1823.

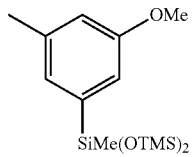

The general procedure was followed with 3-methylanisole (37.4 mg, 0.306 mmol). The product was obtained as a colorless liquid, 86 mg, 82% yield. $^1$H NMR (500 MHz, CDCl$_3$) δ 6.98 (s, 1H), 6.94 (s, 1H), 6.77 (s, 1H), 3.83 (s, 3H), 2.37 (s, 3H), 0.29 (s, 3H), 0.15 (s, 18H). $^{13}$C NMR (126 MHz, CDCl$_3$) δ 159.06 (s), 139.93 (s), 138.81 (s), 126.55 (s), 116.01 (s), 115.45 (s), 55.14 (s), 21.68 (s), 2.03 (s), 0.24 (s). HRMS (EI+) calcd for [C$_{15}$H$_{30}$O$_3$Si$_3$]: 342.1503, found: 342.1510.

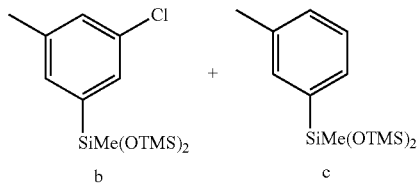

b                    c

The general procedure was followed with 3-chlorotoluene (38.2 mg, 0.302 mmol). The product was obtained as a colorless liquid (98.4 mg, 86% yield of b, 4% yield of c). $^1$H NMR (500 MHz, CDCl$_3$) δ 7.31 (s, 1H), 7.22 (s, 1H), 7.19 (s, 1H), 2.35 (s, 3H), 0.28 (s, 3H), 0.14 (s, 18H). $^{13}$C NMR (126 MHz, CDCl$_3$) δ 140.94 (s), 139.20 (s), 133.95 (s), 132.11 (s), 130.24 (s), 21.32 (s), 2.00 (s), 0.11 (s). HRMS (EI+) calcd for [C$_{14}$H$_{27}$ClO$_2$Si$_3$]: 346.1002. found: 346.1000.

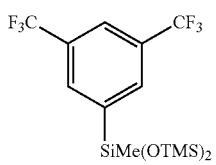

The general procedure was followed with 1,3-bis(trifluoromethyl)benzene (64.3 mg, 0.300 mmol). The product was obtained as a colorless liquid (104 mg, 78% yield). $^1$H NMR (500 MHz, CDCl$_3$) δ 7.98 (s, 2H), 7.88 (s, 1H), 0.33 (s, 3H), 0.14 (s, 18H). $^{13}$C NMR (126 MHz, CDCl$_3$) δ 141.93 (s), 133.26 (s), 130.83 (q, J=32.8 Hz), 123.81 (q, J=272.6 Hz), 123.55-123.00 (m), 1.88 (s), —0.02 (s). $^{19}$F NMR (470 MHz, C$_6$D$_6$) δ −63.10 (s). HRMS (EI+) calcd for [C$_{14}$H$_{21}$F$_6$O$_2$Si$_3$] (M−CH3): 419.0754, found: 419.0764.

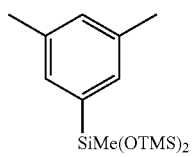

The general procedure was followed with 1,3-xylene (32.7 mg, 0.308 mmol). The product was obtained as a colorless liquid (83.3 mg, 83% yield). $^1$H NMR (600 MHz, CDCl$_3$) δ 7.21 (s, 2H), 7.06 (s, 1H), 2.37 (s, 6H), 0.30 (s, 3H), 0.17 (s, 18H). $^{13}$C NMR (151 MHz, CDCl$_3$) δ 138.40 (s), 136.92 (s), 131.25 (s), 131.15 (s), 21.54 (s), 2.04 (s), 0.33 (s). HRMS (EI+) calcd for [C$_{15}$H$_{30}$O$_2$Si$_3$]: 326.1554, found: 326.1563.

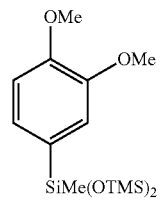

The general procedure was followed with 1,2-dimethoxybenzene (42.3 mg, 0.306 mmol). The product was obtained as a colorless liquid (104 mg, 95% yield). $^1$H NMR (500 MHz, CDCl$_3$) δ 7.13 (d, J=7.8 Hz, 1H), 7.06 (s, 1H), 6.89 (d, J=7.8 Hz, 1H), 3.91 (s, 3H), 3.89 (s, 3H), 0.27 (s, 3H), 0.12 (s, 18H). $^{13}$C NMR (126 MHz, CDCl$_3$) δ 150.22 (s), 148.36 (s), 130.25 (s), 126.58 (s), 115.56 (s), 110.74 (s), 55.76 (s), 55.70 (s), 1.97 (s), 0.25 (s). HRMS (EI+) calcd for [C$_{15}$H$_{30}$O$_4$Si$_3$]: 358.1452, found: 358.1450.

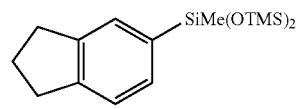

The general procedure was followed with 2,3-dihydro-1H-indene (33.6 mg, 0.284 mmol). The product was obtained as a colorless liquid (87 mg, 90% yield). $^1$H NMR (500 MHz, CDCl$_3$) δ 7.49 (s, 1H), 7.40 (d, J=7.3 Hz, 1H), 7.29 (d, J=7.3 Hz, 1H), 3.00-2.94 (m, 4H), 2.12 (p, J=7.4 Hz, 2H), 0.32 (s, 3H), 0.18 (s, 18H). $^{13}$C NMR (126 MHz, CDCl$_3$) δ 145.83 (s), 143.49 (s), 135.98 (s), 131.32 (s), 129.37 (s), 123.95 (s), 33.13 (s), 32.89 (s), 25.33 (s), 2.07 (s), 0.48 (s). HRMS (EI+) calcd for [C$_{16}$H$_{30}$O$_2$Si$_3$]: 338.1554, found: 338.1558.

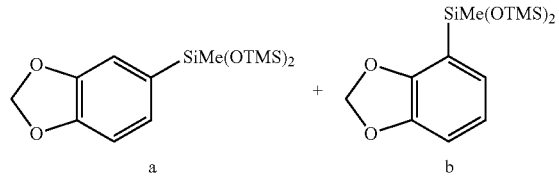

a                    b

The general procedure was followed with benzo[d][1,3]dioxole (35.9 mg, 0.294 mmol) and L1 as the ligand. The product was obtained as a colorless liquid (91.7 mg, 91% yield, a:b=92:8). $^1$H NMR (major isomer, 500 MHz, CDCl$_3$) δ 7.09 (d, J=7.6 Hz, 1H), 7.05 (s, 1H), 6.88 (d, J=7.6 Hz, 1H), 5.97 (s, 2H), 0.29 (s, 3H), 0.15 (s, 18H). $^{13}$C NMR (major isomer, 126 MHz, CDCl$_3$) δ 148.76 (s), 147.25 (s), 131.96 (s), 127.59 (s), 112.79 (s), 108.52 (s), 100.60 (s), 2.00 (s), 0.25 (s). HRMS (EI+) calcd for [C$_{14}$H$_{26}$O$_4$Si$_3$]: 342.1139, found: 342.1138.

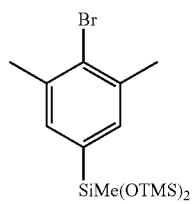

The general procedure was followed with 2-bromo-1,3-dimethylbenzene (54.0 mg, 0.292 mmol). The product was obtained as a colorless liquid (56.8 mg, 48% yield). $^1$H NMR (500 MHz, CDCl$_3$) δ 7.24 (s, 2H), 2.44 (s, 6H), 0.27 (s, 3H), 0.14 (s, 18H). $^{13}$C NMR (126 MHz, CDCl$_3$) δ 137.51 (s), 137.01 (s), 133.17 (s), 129.64 (s), 24.06 (s), 2.03 (s), 0.26 (s). HRMS (EI+) calcd for [C$_{15}$H$_{29}$BrO$_2$Si$_3$]: 404.0659, found: 404.0669.

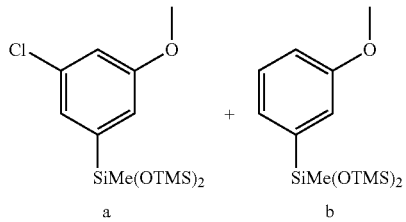

The general procedure was followed with 3-chloroanisole (45.5 mg, 0.319 mmol). The product was obtained as a colorless liquid (94.4 mg, 74% yield of b, 8% yield of c). $^1$H NMR (500 MHz, CDCl$_3$) δ 7.10 (d, J=0.8 Hz, 1H), 6.98 (d, J=2.0 Hz, 1H), 6.92 (s, 1H), 3.81 (s, 3H), 0.28 (s, 3H), 0.14 (s, 18H). $^{13}$C NMR (126 MHz, CDCl$_3$) δ 159.89 (s), 141.97 (s), 134.76 (s), 125.41 (s), 117.14 (s), 115.20 (s), 55.46 (s), 1.99 (s), 0.03 (s). HRMS (EI+) calcd for [C$_4$H$_{27}$ClO$_3$Si$_3$]: 362.0957, found: 362.0965.

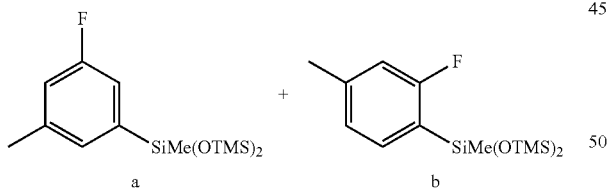

The general procedure was followed with 3-fluorotoluene (32.2 mg, 0.292 mmol) and L1 as the ligand. The product was obtained as a colorless liquid (70.0 mg, 72% yield, a:b =89:11). $^1$H NMR (major isomer, 600 MHz, CDCl$_3$) δ 7.13 (s, 1H), 7.04 (d, J=8.2 Hz, 1H), 6.89 (d, J=9.8 Hz, 1H), 2.37 (s, 3H), 0.28 (s, 3H), 0.14 (s, 18H). $^{13}$C NMR (major isomer, 151 MHz, CDCl$_3$) δ 162.74 (d, J=247.2 Hz), 141.25 (d, J=4.4 Hz), 139.83 (d, J=6.6 Hz), 129.63 (d, J=2.3 Hz), 117.11 (d, J=21.0 Hz), 116.62 (d, J=18.6 Hz), 21.41 (s), 1.98 (s), 0.08 (s). $^{19}$F NMR (major isomer, 565 MHz, CDCl$_3$) δ −116.19 (t, J=9.2 Hz). $^{19}$F NMR (minor isomer, 565 MHz, CDCl$_3$) δ −103.48 (s, J=7.2 Hz). HRMS (EI+) calcd for [C$_{14}$H$_{27}$FO$_2$Si$_3$]: 330.1303, found: 330.1311.

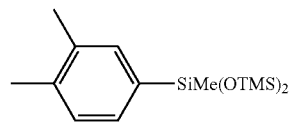

The general procedure was followed with 1,2-xylene (31.0 mg, 0.300 mmol). The product was obtained as a colorless liquid (82.8 mg, 85% yield). $^1$H NMR (500 MHz, CDCl$_3$) δ 7.36 (s, 1H), 7.34 (d, J=7.6 Hz, 1H), 7.17 (d, J=7.3 Hz, 1H), 2.32 (s, 3H), 2.31 (s, 3H), 0.30 (s, 3H), 0.16 (s, 18H), $^{13}$C NMR (126 MHz, CDCl$_3$) δ 138.09 (s), 135.74 (s), 134.76 (s), 131.05 (s), 129.14 (s), 20.01 (s), 19.92 (s), 2.05 (s), 0.38 (s). HRMS (EI+) calcd for [C$_{15}$H$_{30}$O$_2$Si$_3$]: 326.1554, found: 326.1559.

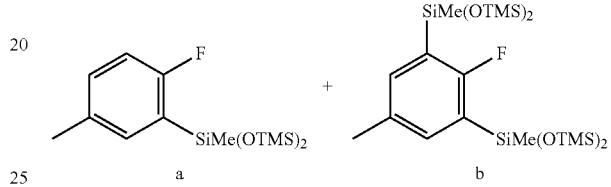

The general procedure was followed with 4-fluorotoluene (32.6 mg, 0.296 mmol). The product was obtained as a colorless liquid (95.7 mg, 98% yield, a:b=96:4). $^1$H NMR (500 MHz, CDCl$_3$) δ 7.30 (dd, J=4.9, 2.0 Hz, 1H), 7.21-7.13 (m, 1H), 6.89 (t, J=8.3 Hz, 1H), 2.34 (s, 3H), 0.35 (d, J=0.8 Hz, 3H), 0.16 (s, 18H). $^{13}$C NMR (126 MHz. CDCl$_3$) δ 165.47 (d, J=239.2 Hz), 135.87 (d, J=10.7 Hz), 132.80 (d, J=3.1 Hz), 132.34 (d, J=8.1 Hz), 124.24 (d, J=29.3 Hz), 114.47 (d, J=25.5 Hz), 20.83 (s), 1.91 (s), 1.22 (s). $^{19}$F NMR (470 MHz, C$_6$D$_6$) δ −107.04 (d, J=4.2 Hz). HRMS (EI+) calcd for [C$_{14}$H$_{27}$FO$_2$Si$_3$]: 330.1303, found: 330.1306.

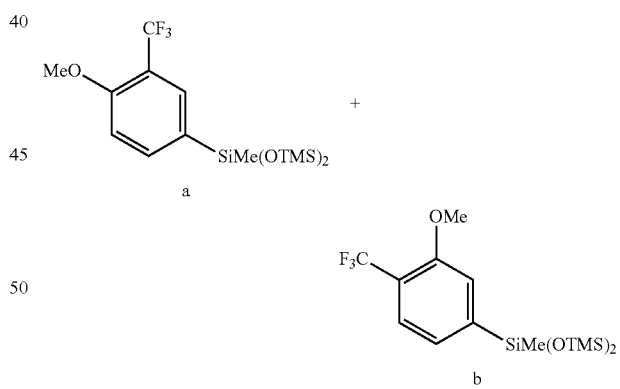

The general procedure was followed with 2-trifluoromethylanisole (52.1 mg, 0.296 mmol) and L1 as the ligand. Following column chromatography, the mixture was distilled to give the product as a colorless liquid (108 mg, 92% yield, a:b=98:2). $^1$H NMR (500 MHz, CDCl$_3$) δ 7.76 (s, 1H), 7.70 (d, J=8.2 Hz, 1H), 7.02 (d, J=8.2 Hz, 1H), 3.92 (s, 3H), 0.29 (s, 3H), 0.14 (s, 18H). $^{13}$C NMR (126 MHz, CDCl$_3$) δ 158.63 (s), 138.71 (s), 132.10 (q, J=5.1 Hz), 129.80 (s), 124.10 (q, J=272.5 Hz), 118.15 (q, J=30.4 Hz), 111.34 (s), 55.84 (s), 1.96 (s), 0.24 (s). $^{19}$F NMR (565 MHz, CDCl$_3$) δ −63.38 (s). HRMS (EI+) calcd for [C$_{15}$H$_{27}$F$_3$O$_3$Si$_3$]: 396.1220, found: 396.1221.

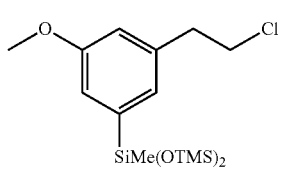

The general procedure was followed with 1-(2-chloroethyl)-3-methoxybenzene (19.5 mg, 0.114 mmol). The product was obtained as a colorless liquid (39.4 mg, 88% yield). $^1$H NMR (600 MHz, CDCl$_3$) δ 6.97 (d, J=2.8 Hz, 2H), 6.77 (s, 1H), 3.81 (s, 3H), 3.70 (t, J=7.5 Hz, 2H), 3.05 (t, J=7.5 Hz, 2H), 0.26 (s, 3H), 0.11 (s, 18H). $^{13}$C NMR (151 MHz, CDCl$_3$) δ 159.23 (s), 140.59 (s), 139.03 (s), 126.15 (s), 116.83 (s), 115.86 (s), 55.25 (s), 45.02 (s), 39.49 (s), 2.02 (s), 0.15 (s). HRMS (EI+) calcd for [C$_{16}$H$_{31}$ClO$_3$Si$_3$]: 390.1270, found: 390.1272.

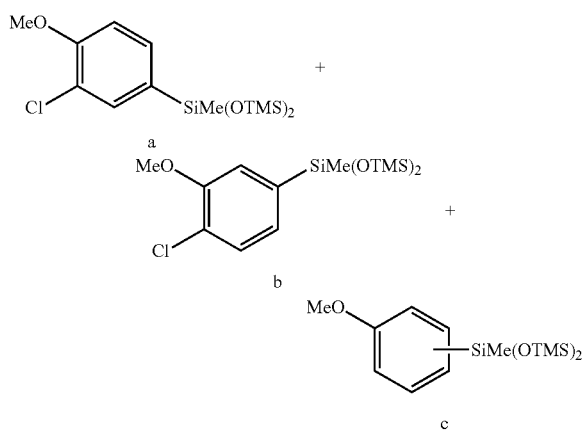

The general procedure was followed with 2-chloroanisole (42.2 mg, 0.296 mmol). The product was obtained as a colorless liquid (101.5 mg, 86% yield of a+b (a:b=94:6), 9% yield of c). $^1$H NMR (a, 600 MHz, CDCl$_3$) δ 7.53 (s, 1H), 7.42 (d, J=7.7 Hz, 1H), 6.94 (d, J=7.9 Hz, 1H), 3.92 (s, 3H), 0.27 (s, 3H), 0.13 (s, 18H). $^{13}$C NMR (151 MHz, CDCl$_3$) δ 156.01 (s), 135.14 (s), 133.09 (s), 131.50 (s), 122.28 (s), 111.66 (s), 56.00 (s), 1.98 (s), 0.19 (s). HRMS (EI+) calcd for [C$_{14}$H$_{27}$ClO$_3$Si$_3$]: 362.0957, found: 362.0957.

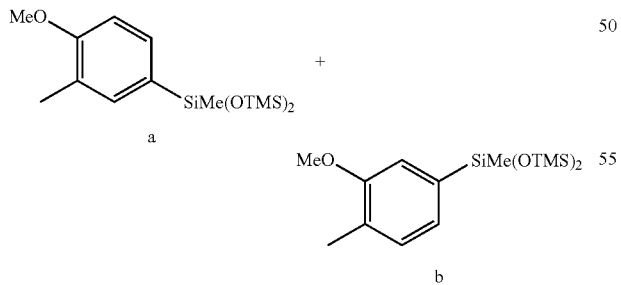

The general procedure was followed with 2-methylanisole (38.4 mg, 0.314 mmol). The product was obtained as a colorless liquid (100.2 mg, 93% yield, a:b=86:14). $^1$H NMR (600 MHz, CDCl$_3$) δ 7.43 (d, J=7.8 Hz, 1H), 7.37 (s, 1H), 6.87 (d, J=7.9 Hz, 1H), 3.88 (s, 3H), 2.29 (s, 3H), 0.31 (s, 3H), 0.17 (d, J=0.7 Hz, 18H). $^{13}$C NMR (151 MHz, CDCl$_3$) δ 159.08 (s), 135.87 (s), 132.56 (s), 129.45 (s), 125.82 (s), 109.33 (s), 55.16 (s), 16.43 (s), 2.05 (s), 0.42 (s). HRMS (EI+) calcd for [C$_{15}$H$_{30}$O$_3$Si$_3$]: 342.1503, found: 342.1499.

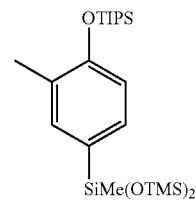

The general procedure was followed with triisopropyl(o-tolyloxy)silane (81.3 mg, 0.307 mmol) with L1 as the ligand. The product was obtained as a colorless liquid (134.8 mg, 90% yield). $^1$H NMR (600 MHz, CDCl$_3$) δ 7.33 (s, 1H), 7.27 (d, J=7.7 Hz, 1H), 6.81 (d, J=7.8 Hz, 1H), 2.28 (s, 3H), 1.40-1.26 (m, 3H), 1.15 (d, J=7.5 Hz, 18H), 0.28 (s, 3H), 0.14 (s, 18H). $^{13}$C NMR (151 MHz, CDCl$_3$) δ 155.79 (s), 136.33 (s), 132.20 (s), 129.93 (s), 127.81 (s), 117.56 (s), 18.22 (s), 17.22 (s), 13.23 (s), 2.04 (s), 0.34 (s). HRMS (EI+) calcd for [C$_3$H$_{48}$O$_3$Si$_4$]: 484.2681, found: 484.2678.

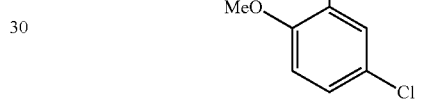

The general procedure was followed with 4-chloroanisole (41.7 mg, 0.292 mmol). The product was obtained as a colorless liquid (87.6 mg, 83% yield). $^1$H NMR (600 MHz, CDCl$_3$) δ 7.43 (s, 1H), 7.30 (d, J=8.6 Hz, 1H), 6.74 (d, J=8.6 Hz, 1H), 3.78 (s, 3H), 0.29 (s, 3H), 0.13 (s, 18H). $^{13}$C NMR (151 MHz, CDCl$_3$) δ 162.55 (s), 135.27 (s), 130.86 (s), 128.59 (s), 125.66 (s), 110.77 (s), 55.14 (s), 1.91 (s), 1.00 (s). HRMS (EI+) calcd for [C$_{14}$H$_{27}$ClO$_3$Si$_3$]: 362.0957, found: 362.0963.

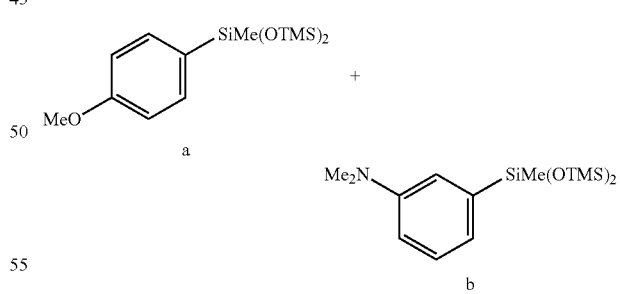

The general procedure was followed with N,N-dimethylaniline (36.3 mg, 0.300 mmol). Following column chromatography, the mixture was distilled to give the product as a colorless liquid (85.9 mg, 84% yield, a:b=92:8). $^1$H NMR (a, 500 MHz, CDCl$_3$) δ 7.49 (d, J=8.5 Hz, 2H), 6.77 (d, J=8.4 Hz, 2H), 3.01 (s, 6H), 0.30 (s, 3H), 0.17 (s, 18H). $^{13}$C NMR (a, 126 MHz, CDCl$_3$) δ 151.37 (s), 134.56 (s), 124.24 (s), 111.68 (s), 40.31 (s), 2.06 (s), 0.47 (s). HRMS (EI+) calcd for [C$_{15}$H$_{31}$NO$_2$Si$_3$]: 341.1663, found: 341.1664.

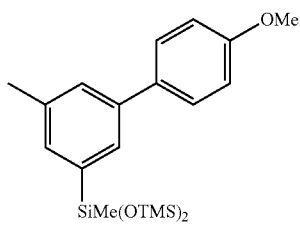

The general procedure was followed with 4'-methoxy-3-methyl-1,1'-biphenyl (58.5 mg, 0.295 mmol). The product was obtained as a colorless liquid (99.2 mg, 80% yield). $^1$H NMR (600 MHz, CDCl$_3$) δ 7.62 (s, 1H), 7.59 (d, J=8.0 Hz, 2H), 7.45 (s, 1H), 7.39 (s, 1H), 7.05 (d, J=8.0 Hz, 2H), 3.90 (s, 3H), 2.48 (s, 3H), 0.37 (s, 3H), 0.21 (s, 18H). $^{13}$C NMR (151 MHz, CDCl$_3$) δ 159.15 (s), 140.07 (s), 138.97 (s), 137.41 (s), 134.36 (s), 132.53 (s), 128.96 (s), 128.95 (s), 128.31 (s), 114.29 (s), 55.42 (s), 21.74 (s), 2.09 (s), 0.35 (s). HRMS (EI+) calcd for [C$_{21}$H$_{34}$O$_3$Si$_3$]: 418.1816, found: 418.1825.

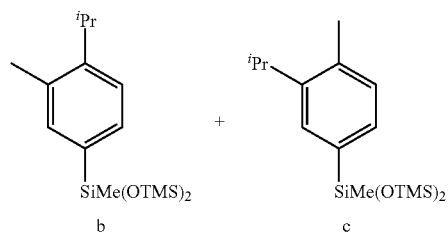

The general procedure was followed with o-cymene (42.0 mg (0.313 mmol). The product was obtained as a colorless liquid (76.6 mg, 69% yield, b:c=82:18). $^1$H NMR (b, 500 MHz, CDCl$_3$) δ 7.41 (d, J=7.6 Hz, 1H), 7.34 (s, 1H), 7.27 (d, J=7.6 Hz, 1H), 3.20-3.13 (m, 1H), 2.38 (s, 3H), 1.26 (d, J=6.9 Hz, 6H), 0.29 (s, 3H), 0.16 (s, 18H). $^{13}$C NMR (b, 126 MHz, CDCl$_3$) δ 148.25 (s), 135.42 (s), 135.27 (s), 134.14 (s), 131.42 (s), 124.09 (s), 29.46 (s), 23.27 (s), 19.53 (s), 2.06 (s), 0.47 (s). HRMS (EI+) calcd for [C$_{17}$H$_{14}$O$_2$Si$_3$]: 354.1867, found: 354.1872.

Derivatization of the Arylsilane Products

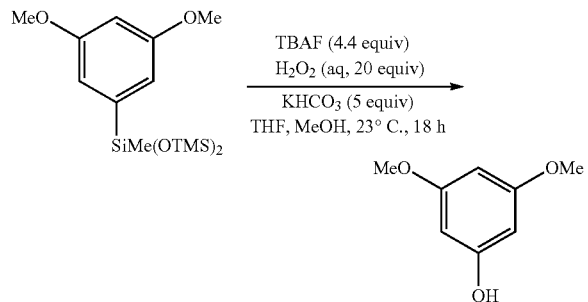

3,5-Dimethoxyphenol (51): To a solution of 4b (73.1 mg, 0.204 mmol) in THF (2.8 mL) was added dropwise TBAF (1.0 M THF solution, 1.0 mL) at 0° C., and the mixture was stirred at 0° C. for 15 min. Methanol (1.0 mL), KHCO$_3$ (100 mg), and H$_2$O$_2$ (30% aqueous solution, 1.0 mL) were then added to the reaction mixture, which was stirred at 23° C. for 18 h. The reaction mixture was diluted with ethyl acetate (10 mL) and quenched with KHSO$_4$ (saturated aqueous solution, 2 mL) at 0° C. The aqueous phase was extracted with ethyl acetate (5 mL×3), the combined organic layer was dried over MgSO$_4$, filtered, and the solvent was evaporated in vacuo. The residue was purified by flash column chromatography on silica (0→40% ethyl acetate in hexanes) to give the product as a colorless solid (21.7 mg, 69% yield). $^1$H NMR (400 MHz, CDCl$_3$) δ 6.08 (s, 1H), 6.03 (s, 2H), 5.32 (bs, 1H), 3.75 (s, 6H). $^{13}$C NMR (101 MHz, CDCl$_3$) δ 161.74 (s), 157.53 (s), 94.36 (s), 93.26 (s), 55.48 (s). The NMR spectra agree with those of the authentic sample.

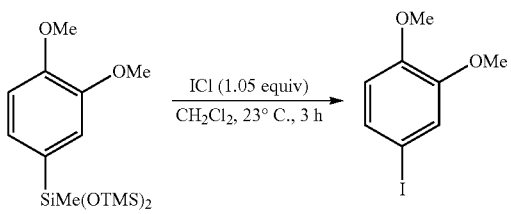

4-Iodo-1,2-dimethoxybenzene (52) (Janssen, et al., *J. Org. Chem.* 20:1326-1329 (1955)): To a solution of 13b (97.6 mg, 0.272 mmol) in CH$_2$Cl$_2$ (1 mL) was added a solution of ICl (46.3 mg, 1.05 equiv) in CH$_2$Cl$_2$ (1 mL) at 0° C. The reaction mixture was stirred at 23° C. for 3 h. The volatile materials were evaporated in vacuo, and the residue was purified by flash column chromatography on silica (0→20% ethyl acetate in hexanes) to give the product as a colorless liquid that solidified at 23° C. (67.5 mg, 94% yield). $^1$H NMR (600 MHz, CDCl$_3$) δ 7.20 (d, J=8.4 Hz, 1H), 7.10 (s, 1H), 6.60 (d, J=8.4 Hz, 1H), 3.84 (s, 3H), 3.83 (s, 3H). $^{13}$C NMR (151 MHz. CDCl$_3$) δ 149.83 (s), 149.16 (s), 129.78 (s), 120.33 (s), 113.18 (s), 82.39 (s), 56.13 (s), 55.96 (s).

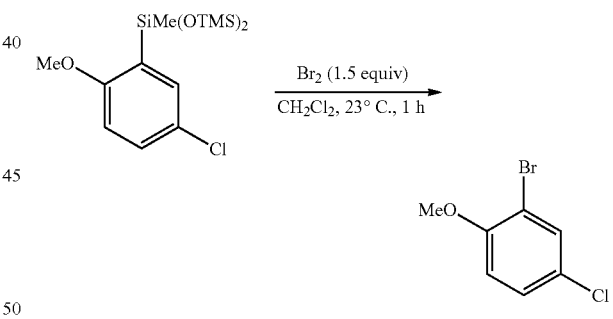

2-Bromo-4-chloro-1-methoxybenzene (54) (Hamashima, et al., *J. Am. Chem. Soc.* 127:10164-10165 (2005)): To a solution of 16b (151 mg, 0.416 mmol) in CH$_2$Cl$_2$ (5 mL) was added bromine (100 mg, 0.626 mmol) at 0° C., and the reaction mixture was stirred at 23° C. for 1 h. The reaction was then quenched with Na$_2$S$_2$O$_3$ (30% aqueous solution, 2 mL) at 0° C. The aqueous phase was extracted with ethyl acetate, the combined organic layer was dried over MgSO$_4$, filtered, and the solvent was evaporated in vacuo. The residue was purified by flash column chromatography (0→10% ethyl acetate in hexanes) to give the product as a colorless liquid (81.6 mg, 89% yield). $^1$H NMR (600 MHz, CDCl$_3$) δ 7.53 (d, J=2.4 Hz, 1H), 7.24 (dd, J=8.8, 2.4 Hz, 1H), 6.81 (d, J=8.8 Hz, 1H), 3.87 (s, 3H). $^{13}$C NMR (151 MHz, CDCl$_3$) δ 154.87 (s), 132.93 (s), 128.41 (s), 126.07 (s), 112.64 (s), 112.23 (s), 56.58 (s).

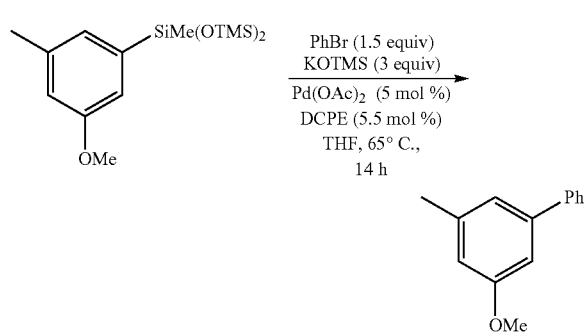

3-Methoxy-5-methyl-1,1'-biphenyl (53): To a solution of Pd(OAc)$_2$ (2.5 mg) and 1,2-bis(dicyclohexylphosphino)ethane (DCPE, 5.2 mg) in THF (660 mg) was added 2b (76.9 mg, 0.224 mmol), bromobenzene (52 mg, 0.33 mmol), and KOTMS (85 mg, 0.66 mmol), and the reaction mixture was stirred at 65° C. for 14 h. The solvent was then evaporated in vacuo. and the residue was purified by flash column chromatography (hexanes) to give the product as a colorless liquid (36.5 mg, 82% yield). $^1$H NMR (600 MHz. CDCl$_3$) δ 7.62 (d, J=7.9 Hz, 2H), 7.46 (t. J=7.6 Hz, 2H), 7.37 (t, J=7.3 Hz, 1H), 7.05 (s, 1H), 6.98 (s, 1H), 6.76 (s, 1H), 3.88 (s, 3H), 2.43 (s, 3H). $^{13}$C NMR (151 MHz, CDCl$_3$) δ 160.09 (s), 142.71 (s), 141.39 (s), 139.88 (s), 128.80 (s), 127.45 (s), 127.33 (s), 120.76 (s), 113.69 (s), 110.08 (s), 55.39 (s), 21.80 (s). HRMS (EI+) calcd for [C$_{14}$H$_{14}$O]: 198.1045, found: 198.1048.

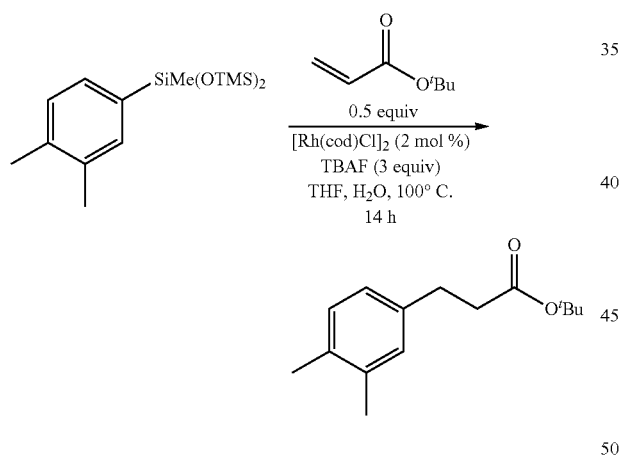

tert-Butyl 3-(3,4-dimethylphenyl)propanoate (55): To a solution of [Rh(cod)Cl]$_2$ (2.0 mg), 14b (131 mg, 0.401 mmol), and tert-butylacrylate (26 mg, 0.20 mmol) in THF (800 mg) was added dropwise TBAF (1.0 M THF solution, 0.6 mL) at 0° C. Degassed water (0.3 mL) was then added, and the reaction mixture was stirred vigorously at 100° C. for 14 h. The organic layer was then separated and the aqueous phase diluted with NH$_4$Cl (saturated aqueous solution, 2 mL). The aqueous phase was extracted with hexanes (3 mL×3), the combined organic phase dried over MgSO$_4$, filtered, and the solvents were evaporated in vacuo. The residue was purified by flash column chromatography (0→10% ethyl acetate in hexanes) to give the product as a colorless liquid (41.9 mg, 87% yield). $^1$H NMR (600 MHz, CDCl$_3$) δ 7.04 (d, J=7.6 Hz, 1H), 6.98 (s, 1H), 6.93 (d, J=7.6 Hz, 1H), 2.87-2.79 (m, 2H), 2.54-2.48 (m, 2H), 2.23 (s, 3H), 2.22 (s, 3H), 1.43 (s, 9H). $^{13}$C NMR (151 MHz, CDCl$_3$) δ 172.61 (s), 138.37 (s), 136.60 (s), 134.32 (s), 129.80 (d, J=5.3 Hz), 125.75 (s), 80.39 (s), 37.46 (s), 30.83 (s), 28.24 (s), 19.85 (s), 19.43 (s). HRMS (EI+) calcd for [C$_{15}$H$_{22}$O$_2$]: 234.1620, found: 234.1625.

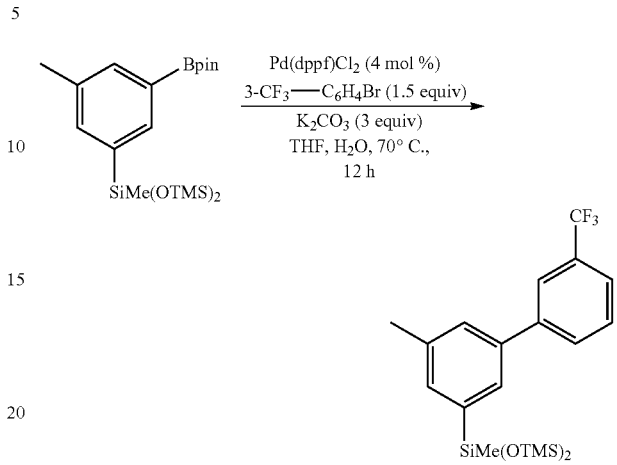

1,1,1,3,5,5,5-Heptamethyl-3-(5-methyl-3'-(trifluoromethyl)-[1,1'-biphenyl]-3-yl)trisiloxane (61): To a solution of Pd(dppf)Cl2 (9.8 mg), 10b (135.1 mg, 0.308 mmol), and 1-bromo-3-(trifluoromethyl)benzene (101 mg, 0.449 mmol) in THF (2.4 g) was added K$_2$CO$_3$ (124 mg, 0.897 mmol). Water (0.2 mL) was then added, and the reaction mixture was stirred vigorously at 70° C. for 12 h. The solvents were evaporated in vacuo, and the residue was purified by flash column chromatography to give the product as a colorless liquid (139.2 mg, 99% yield). $^1$H NMR (600 MHz, CDCl$_3$) δ 7.93 (s, 1H), 7.83 (d, J=7.6 Hz, 1H), 7.70-7.63 (m, 2H), 7.61 (t, J=7.7 Hz, 1H), 7.50 (d, J=3.1 Hz, 2H), 2.52 (s, 3H), 0.40 (s, 3H), 0.23 (s, 18H). $^{13}$C NMR (151 MHz, CDCl$_3$) δ 142.68 (s), 139.61 (s), 139.11 (s), 137.88 (s), 133.92 (s), 131.34 (q, J=31.9 Hz), 130.55 (s), 129.42 (s), 129.34 (s), 129.25 (s), 124.46 (q, J=272.3 Hz), 124.17 (q, J=3.7 Hz), 123.89 (q, J=3.5 Hz), 21.69 (s), 2.06 (s), 0.35 (s). $^{19}$F NMR (376 MHz, CDCl$_3$) δ −61.82 (s). HRMS (EI+) calcd for [C$_{21}$H$_{31}$F$_3$O$_2$Si$_3$]: 456.1584. found: 456.1590.

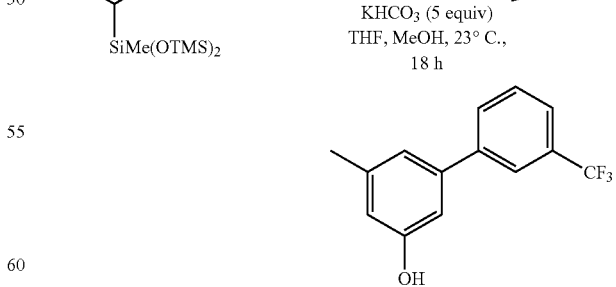

5-Methyl-3'-(trifluoromethyl)-[1,1'-biphenyl]-3-ol (62): A procedure similar to the oxidation of 4b was followed with 61 (67.8 mg, 0.148 mmol). The product was obtained as a colorless solid (34.0 mg, 91% yield). $^1$H NMR (600 MHz, CDCl$_3$) δ 7.80 (s, 1H), 7.72 (d, J=7.7 Hz, 1H), 7.60 (d, J=7.7

Hz, 1H), 7.53 (t, J=7.7 Hz, 1H), 6.99 (s, 1H), 6.88 (s, 1H), 6.71 (s, 1H), 5.09 (s, 1H), 2.39 (s, 3H). $^{13}$C NMR (151 MHz, CDCl$_3$) δ 156.06 (s), 141.79 (s), 141.45 (s), 140.65 (s), 131.21 (q, J=32.3 Hz), 130.50 (s), 129.29 (s), 124.32 (q, J=272.5 Hz), 124.18 (q, J=3.7 Hz), 124.03 (q, J=3.9 Hz), 120.85 (s), 115.84 (s), 111.44 (s), 21.56 (s). $^{19}$F NMR (376 MHz, CDCl$_3$) δ −62.51 (s). HRMS (EI+) calcd for [C$_{14}$H$_{11}$F$_3$O]: 252.0762, found: 252.0763.

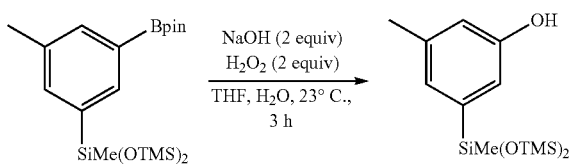

3-(1,1,1,3,5,5,5-Heptamethyltrisiloxan-3-yl)-5-methylphenol (63): To a solution of 10b (114.5 mg, 0.261 mmol) in THF (3 mL) and water (1 mL) was added NaOH (21 mg) and dropwise H$_2$O$_2$ (30% aqueous solution, 54 μL). The reaction mixture was stirred at 23° C. for 4 h. The reaction was then diluted with ethyl acetate (5 mL) and quenched with KHSO$_4$ (saturated aqueous solution, 2 mL) at 0° C. The aqueous phase was extracted with ethyl acetate (4 mL×4), the combined organic layer was dried over MgSO$_4$, filtered, and the solvents were evaporated in vacuo. The residue was purified by flash column chromatography to give the product as a colorless liquid (79.4 mg, 91% yield). $^1$H NMR (500 MHz, CDCl$_3$) δ 6.95 (s, 1H), 6.85 (s, 1H), 6.69 (s, 1H), 5.14 (s, 1H), 2.33 (s, 3H), 0.27 (s, 3H), 0.14 (s, 18H). $^{13}$C NMR (126 MHz. CDCl$_3$) δ 154.91 (s), 140.31 (s), 139.13 (s), 126.64 (s), 117.35 (s), 116.91 (s), 21.47 (s), 2.00 (s), 0.16 (s). HRMS (EI+) calcd for [C$_{14}$H$_{28}$O$_3$Si$_3$]: 328.1346, found: 328.1353.

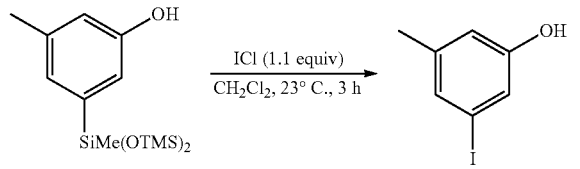

3-Iodo-5-methylphenol (64): A procedure similar to the iodination of 13b was followed with 63 (49.3 mg, 0.150 mmol). The product was obtained as a colorless solid (27.8 mg, 79% yield). $^1$H NMR (600 MHz, CDCl$_3$) δ 7.12 (s, 1H), 7.01 (s, 1H), 6.61 (s, 1H), 4.99 (s, 1H), 2.25 (s, 3H). $^{13}$C NMR (151 MHz, CDCl$_3$) δ 155.96 (s), 141.71 (s), 130.94 (s), 121.76 (s), 115.93 (s), 94.24 (s), 21.04 (s). HRMS (EI+) for [C$_7$H$_7$IO]: 233.9542, found: 233.9546.

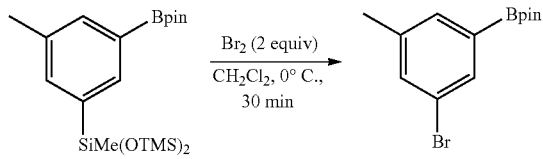

2-(3-Bromo-5-methylphenyl)-4,4,5,5-tetramethyl-1,3,2-dioxaborolane (65): A procedure similar to the bromination of 16b was followed with 10b (94.8 mg, 0.216 mmol) at 0° C. for 30 min. The product was obtained as a colorless solid (53.1 mg, 83% yield). $^1$H NMR (500 MHz, CDCl$_3$) δ 7.74 (s, 1H), 7.54 (s, 1H), 7.42 (s, 1H), 2.33 (s, 3H), 1.34 (s, 12H). $^{13}$C NMR (126 MHz, CDCl$_3$) δ 139.66 (s), 134.90 (s), 134.56 (s), 133.98 (s), 122.40 (s), 84.21 (s), 24.96 (s), 21.06 (s). $^{11}$B NMR (193 MHz, CDCl$_3$) δ 29.93 (bs). HRMS (EI+) for [C$_{13}$H$_{18}$BBrO$_2$]: 296.0583, found: 296.0585.

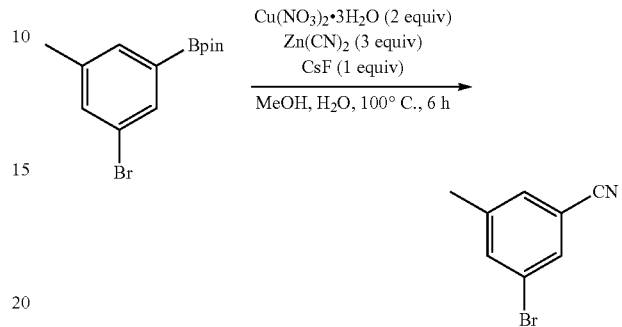

3-Bromo-5-methylbenzonitrile (66) (Murphy, et al., *J. Am. Chem. Soc.* 129:15434-15435 (2007)): The literature procedure (Liskey, et al., *J. Am. Chem. Soc.* 132:11389-11391 (2010)) was followed with 65 (52.6 mg, 0.177 mmol). The product was obtained as a colorless solid, 20.5 mg (59% yield). $^1$H NMR (600 MHz, CDCl$_3$) δ 7.59 (s, 1H), 7.56 (s, 1H), 7.40 (s, 1H), 2.38 (s, 3H). $^{13}$C NMR (151 MHz, CDCl$_3$) δ 141.43 (s), 136.92 (s), 131.94 (s), 131.39 (s), 122.75 (s), 117.61 (s), 113.98 (s), 21.06 (s).

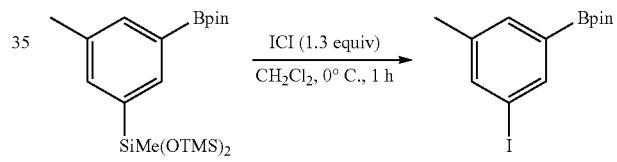

2-(3-Iodo-5-methylphenyl)-4,4,5,5-tetramethyl-1,3,2-dioxaborolane (67): A procedure similar to the iodination of 13b was followed with 10b (66.6 mg, 0.152 mmol) at 0° C. for 1 h. The product was obtained as a colorless solid (45.8 mg, 88% yield). $^1$H NMR (500 MHz, CDCl$_3$) δ 7.94 (s, 1H), 7.64 (s, 1H), 7.57 (s, 1H), 2.30 (s, 3H), 1.34 (s, 12H). $^{13}$C NMR (126 MHz, CDCl$_3$) δ 140.85 (s), 140.53 (s), 139.74 (s), 134.59 (s), 94.70 (s), 84.21 (s), 24.97 (s), 20.96 (s). $^{11}$B NMR (160 MHz, CDCl$_3$) δ 30.27 (bs). HRMS (EI+) calcd for [C$_{13}$H$_{18}$BIO$_2$]: 344.0445, found: 344.0449.

Intramolecular Silylation of Arenes

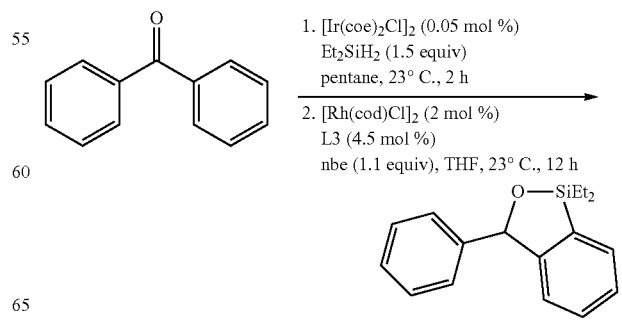

1,1-Diethyl-3-phenyl-1,3-dihydrobenzolo[c][1,2]oxasilole (73) (Simmons, et al., *Am. Chem. Soc.* 132:17092-17095 (2010)): To a solution of benzophenone (38.0 mg, 0.209 mmol) in pentane (100 mg) was added a stock solution of [Ir(coe)$_2$Cl]$_2$ (0.05 mol %) in Et$_2$SiH$_2$ (27 mg), and the reaction mixture was stirred at 23° C. for 2 h. The volatile materials were then evaporated in vacuo, and the residue was dissolved in THF (100 mg) and added to a solution of [Rh(cod)Cl]$_2$ (2.0 mg) and L3 (DTBM-Segphos, 10.5 mg) in THF (100 mg). Norbornene (20 mg) was added, and the reaction mixture was stirred at 23° C. for 12 h. The volatile materials were then evaporated in vacuo, and the residue was purified by flash column chromatography (0→5% ethyl acetate in hexanes) to give the product as a colorless liquid (47.6 mg, 87% yield, Chiralpak OJH column, 1% isopropanol in hexanes, e.r.=95:5). $^1$H NMR (600 MHz, CDCl$_3$) δ 7.64 (d, J=6.4 Hz, 1H), 7.39-7.28 (m, 7H), 7.05 (d, J=7.1 Hz, 1H), 6.19 (s, 1H), 1.11 (t, J=7.8 Hz, 3H), 1.05-0.99 (m, 5H), 0.98-0.86 (m, 2H). $^{13}$C NMR (151 MHz, CDCl$_3$) δ 153.14 (s), 143.90 (s), 133.59 (s), 131.35 (s), 129.85 (s), 128.60 (s), 127.95 (s), 127.50 (s), 127.10 (s), 123.92 (s), 84.39 (s), 7.38 (s), 7.07 (s), 6.97 (s), 6.64 (s).

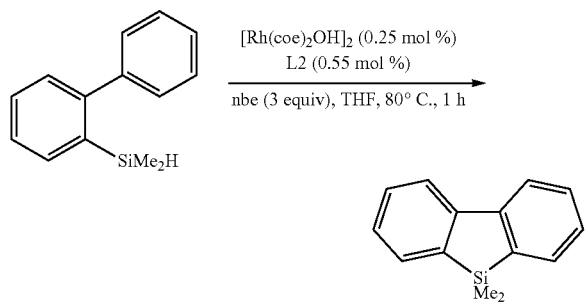

5,5-Dimethyl-5H-dibenzo[b,d]silole (71) (Ureshino, et al., *J. Am. Chem. Soc.* 132:14324-14326 (2010)): To a stock solution of [Rh(coe)$_2$OH]$_2$ (0.25 mol %) and L2 (0.55 mol %) in THF (50 mg) was added [1,1'-biphenyl]-2-yldimethylsilane (20.8 mg, 0.0979 mmol) (Ureshino, et al., *J. Am. Chem. Soc.* 132:14324-14326 (2010)) and norbornene (30 mg). The reaction mixture was heated at 80° C. for 1 h. The volatile materials were then evaporated in vacuo, and the residue was purified by flash column chromatography to give the product as a colorless liquid (19.4 mg, 94% yield). $^1$H NMR (600 MHz, CDCl$_3$) δ 7.85 (d, J=7.7 Hz, 2H), 7.66 (d, J=7.0 Hz, 2H), 7.46 (t, J=7.5 Hz, 2H), 7.31 (t, J=7.2 Hz, 2H), 0.45 (s, 6H). $^{13}$C NMR (151 MHz, CDCl$_3$) δ 147.93 (s), 139.06 (s), 132.85 (s), 130.30 (s), 127.47 (s), 120.94 (s), —3.12 (s).

Results and Discussion

For arene silylation to be practical, the reaction is preferably conducted with a readily available silicon source, e.g., hydrosilane, bearing at least one heteroatom, under mild conditions, with arenes as the limiting reagent. The present invention provides reaction including a catalyst and hydrogen acceptor that leads to the dehydrogenative coupling of arenes with silanes to form aryl silanes in high yields, with a 1:2 ratio of arene to silane. The reactions occur with remarkably high selectivities at the most sterically accessible C—H bond of 1,3-disubstituted arenes, as well as with high selectivities for many 1,2 and 1,4-substituted arenes for which the borylation of the same substrates gives statistical mixtures of products. The hydrosilane reagent in the new process contains two siloxy groups. Thus, the products are useful intermediates for cross-coupling, oxidation, and halogenation. Finally, the conditions for these transformations are orthogonal to those for the transformation of arylboron derivatives, and this orthogonality allows C—H silylation and borylation to generate intermediates that can be derivatized sequentially to form a variety of arenes with substitution patterns difficult to access by classical electrophilic aromatic substitution or the more recently developed C—H bond oxidation or borylation alone.

Drawing upon recent experience with the dehydrogenative silylation of terminal alkenes (Cheng, et al., *Angew. Chem. Int. Ed.* 52:8984-8989 (2013)), we investigated the reactivity of (TMSO)$_2$MeSiH, a trisiloxane available in bulk quantities, in the silylation of arenes. With the same catalyst for the silylation of alkenes generated from [Ir(cod)OMe]$_2$ and 2-methyl-1,10-phenanthroline (2-MePhen) (Poole, et al., *Org. Biomol. Chem.* 3:1013-1024 (2005)) and equal molar of benzene and (TMSO)$_2$MeSiH in THF at 80° C., silylbenzene was obtained in 16% yield after 18 h. Running the reaction in the presence of hydrogen acceptor norbornene (nbe) increased the yield to 31%, but a side product, silylnorbornene (nbe-Si, m/z=299.1), generated from dehydrogenative silylation of nbe, was also formed in 57% yield. Surveying a series of alkenes revealed that reaction run with cyclohexene as the hydrogen acceptor afforded the product in 29% yield without the formation of any alkene silylation product.

The activity of the catalyst was investigated as a series of alternative combinations of metal complexes and ligands not investigated previously for arene silylation or even arene borylation. The reactivity of the combination of [Rh(cod)Cl]$_2$ and several phosphine ligands was probed. Although phosphine-ligated rhodium complexes are used commonly for hydrogenation and hydrosilylation of alkenes (*Modern Rhodium-Catalyzed Organic Reactions*. (Wiley-VCH, ed. 1, 2005)), they have not been reported to catalyzed the intermolecular silylation or borylation of arenes. For applications of phosphine-ligated rhodium catalysts in intramolecular silylation, see T. Ureshino, T. Yoshida, Y. Kuninobu, K. Takai, *J. Am. Chem. Soc.* 132, 14324-14326 (2010) and Y. Kuninobu, T. Nakahara, H. Takeshima, K. Takai, *Org. Lett* 15, 426-428 (2013). Reactions run with simple bisphosphines, such as dppb or dcpe, as the ligand gave no silylbenzene product. However, reaction run with DTBM-Segphos (L3) as the ligand afforded the desired product in 68% yield. Silylcyclohexane (Si—Cy, m/z=304.2), from hydrosilylation of cyclohexene, was produced in parallel in 30% yield. This side reaction accounted for the silane that was not converted to the silylarene product. Other hydrogen acceptors we tested were more prone to hydrosilylation, and lower yields of the desired dehydrogenative coupling product were obtained. However, reactions with catalysts generated from other rhodium precursors, such as [Rh(coe)$_2$Cl]$_2$ and [Rh(coe)$_2$OH]$_2$, led to lower yields of the hydrosilylation product and higher yields of the desired arylsilane. Finally, a series of phosphine ligands containing biaryl architecture similar to the one in L3 was investigated. While reactions with several members of the MeO-BIPHEP, Segphos, Garphos, and BINAP ligand family afforded the product in synthetically useful yields, L1 and L2 were selected for further studies because reactions with these ligands gave the highest yields of the product (entries 13 and 14), while the two ligands possess very different steric properties.

Scheme 1. Investigation of the reaction conditions for the silylation of arenes.[a]

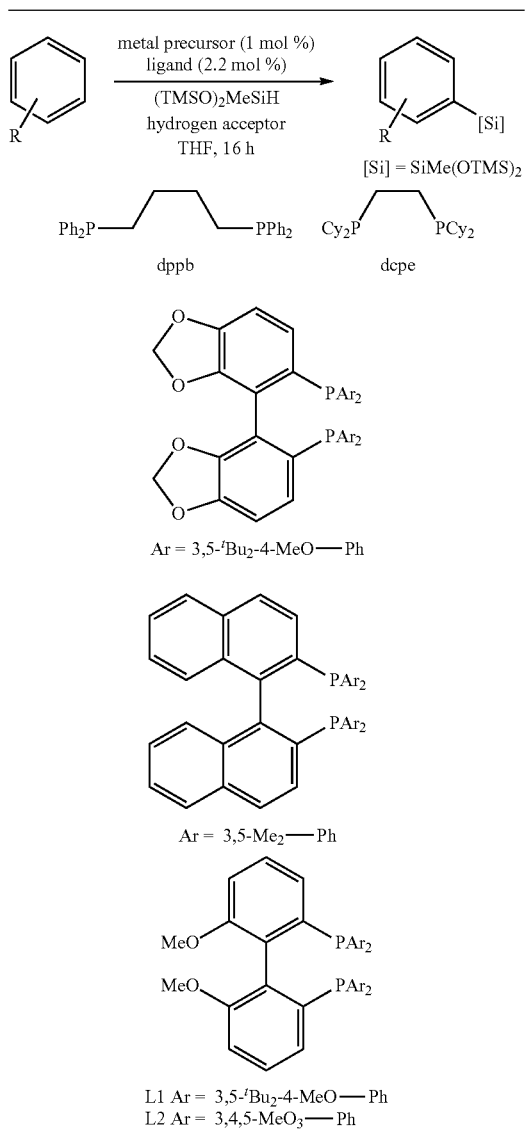

| entry | arene | metal precursor | ligand | acceptor | T (° C.) | yield (%) |
|---|---|---|---|---|---|---|
| 1 | benzene | [Ir(cod)OMe]$_2$ | 2-MePhen | none | 80 | 16 |
| 2 | benzene | [Ir(cod)OMe]$_2$ | 2-MePhen | nbe | 80 | 31[b] |
| 3 | benzene | [Ir(cod)OMe]$_2$ | 2-MePhen | tbe[c] | 80 | 36[d] |
| 4 | benzene | [Ir(cod)OMe]$_2$ | 2-MePhen | cyclohexene | 80 | 29 |
| 5 | benzene | [Rh(cod)Cl]$_2$ | dppb | cyclohexene | 80 | 0 |
| 6 | benzene | [Rh(cod)Cl]$_2$ | dcpe | cyclohexene | 80 | 0 |
| 7 | benzene | [Rh(cod)Cl]$_2$ | L3 | cyclohexene | 80 | 68 |
| 8 | toluene | [Rh(cod)Cl]$_2$ | L3 | cyclohexene | 65 | 38 |
| 9 | toluene | [Rh(coe)$_2$Cl]$_2$ | L3 | cyclohexene | 65 | 68 |
| 10 | toluene | [Rh(coe)$_2$OH]$_2$ | L3 | cyclohexene | 65 | 74 |
| 11 | 1,3-xylene | [Rh(coe)$_2$OH]$_2$ | L3 | cyclohexene | 50 | 64 |
| 12 | 1,3-xylene | [Rh(coe)$_2$OH]$_2$ | L4 | cyclohexene | 50 | 60 |
| 13 | 1,3-xylene | [Rh(coe)$_2$OH]$_2$ | L1 | cyclohexene | 50 | 68 |
| 14 | 1,3-xylene | [Rh(coe)$_2$OH]$_2$ | L2 | cyclohexene | 50 | 75 |
| 15[e] | 1,3-xylene | [Rh(coe)$_2$OH]$_2$ | L2 | cyclohexene | 45 | 92[f] |

[a]Yields of the products were determined by GC analysis.
[b]Silylated alkene was obtained in 57% yield.
[c]3,3-Dimethyl-1-butene.
[d]Silylated alkene was obtained in 60% yield.
[e]Reaction was run with 2 equivalents of silane and cyclohexane.
[f]The yield was determined by NMR spectroscopy.

Because the silane and cyclohexene are commercially available and inexpensive, the reaction of 1,3-xylene catalyzed by [Rh(coe)$_2$OH]$_2$ and L2 with 2 equivalents of silane and acceptor was conducted to ensure complete conversion of the arene. The silylation product was obtained in 92% yield (Table 1, entry 15). The reactions of a series of substituted arenes under these conditions gave the arylsilane products as single isomers in good to excellent yields (Scheme 2). The regioselectivity of the arene silylation is controlled largely by steric effects. The reactions of 1,3-disubstituted arenes occurred only at the mutually meta position (except for reactions of fluoroarenes, vida infra). The reaction is compatible with a wide range of functional groups, including silyl ethers, tertiary amines, tertiary amides, and the pinacolboronate (Bpin) group, the last of which allows selective, sequential 1,3-difunctionalization of arenes (vida infra). Even reaction with substrate 9 bearing a potentially directing amide group gave the 1,3,5-trisubstituted arene (9b) as the single product. This selectivity parallels the selectivity of the valuable borylation of arenes, but with a more practical reagent and to form a linkage that undergoes subsequent transformations under conditions orthogonal to those of arylboronates.

Silylation of certain 1,4-disubstituted arenes also proceeded with high selectivity, and this selectivity was higher than that of the borylation of arenes. For example, silylation of 4-chloroanisole (16a) gave exclusively 4-chloro-2-silylanisole, whereas borylation of this substrate gave a mixture of two monoborylation isomers and a diborylation product in a ratio of 43:18:39 (borylation reaction was carried out according to the literature procedure: Liskey, et al., J. Am. Chem. Soc. 132:11389-11391 (2010)). Similarly, selective silylation of the 1,3-disubstituted aryl ring of 3-(4-MeO-Ph)-toluene (17a) occurred, while borylation of this substrate gave a mixture of isomers (13:87) (borylation reaction was carried out according to the literature procedure: Liskey, et al., J. Am. Chem. Soc. 132:11389-11391 (2010)). This high level of regioselectivity is though to be due to the steric bulk of the ligand.

Scheme 2. The regioselective silylation of arenes.[a]

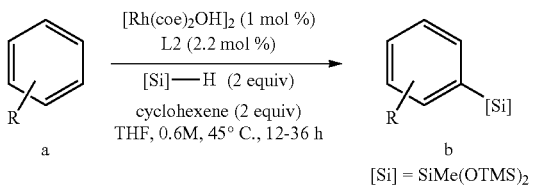

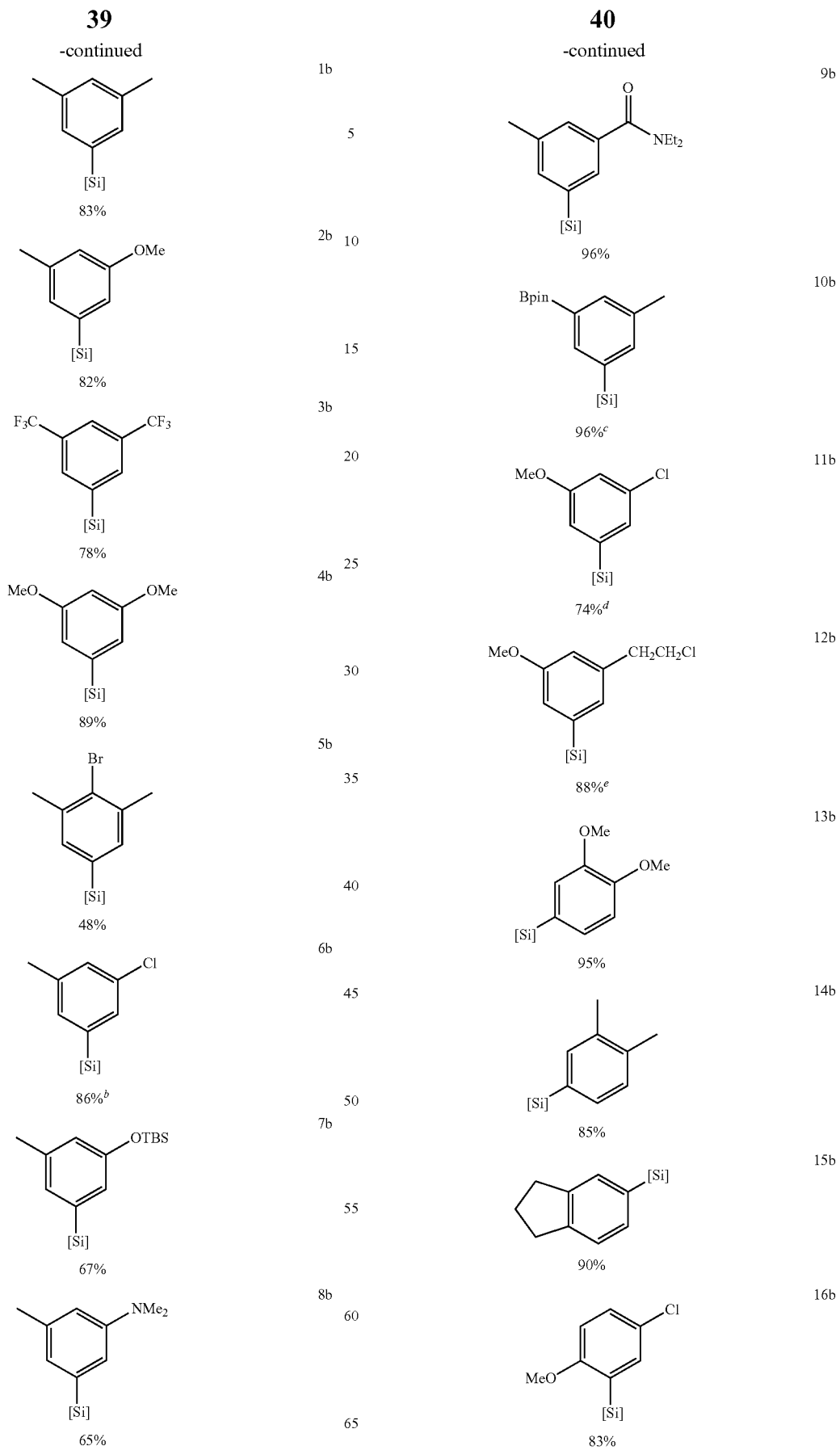

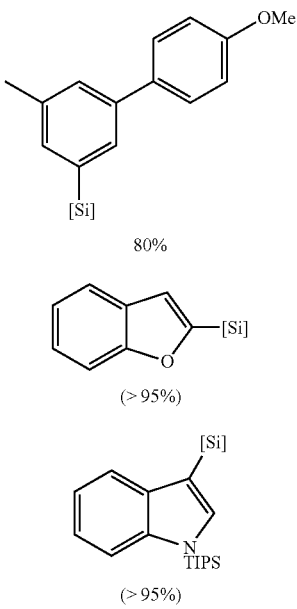

17b, 80%

18b, (>95%)

19b, (>95%)

[a]Reactions conducted on a 0.3 mmol scale unless otherwise stated. Isolated yields reported. [b]Dechloronated product was also obtained in 4% yield. [c]Reaction run on a 2.0 mmol scale. [d]Dechloronated product was also obtained in 8% yield. [e]Reaction run on a 0.1 mmol scale.

Regioselective functionalization of unsymmetrically 1,2-substituted benzene derivatives is challenging because the steric properties of the substituents are conveyed from the meta position. Similarly, regioselective functionalization of fluoroarenes is challenging because of the small size of the fluorine atom and thus facile functionalization ortho to the fluorine. Borylation of unsymmetrically 1,2-substituted benzene generally affords a mixture of constitutional isomers as well as products of diborylation when one of the two substituents is small.

Indeed, the silylation of unsymmetrically 1,2-disubstituted arenes occurred with selectivities and yields that are synthetically useful. Consistent with the hypothesis that remote steric effects can be exploited, higher regioselectivity was achieved by running the reaction with the more sterically hindered ligand L1 bearing tert-butyl groups than with L2 bearing methoxy groups. More importantly, the selectivities for functionalization at the more sterically accessible site was much higher for silylation conducted with L2 than those for the borylation of the same arene catalyzed by [Ir(COD)OMe]$_2$ and di-tert-butylbipyridine (dtbpy), and products from difunctionalization of fluoroarenes (21a and 22a) were obtained in much lower yields. For example, the reaction of 3-fluorotoluene (22a) with L1 as the ligand occurred with a selectivity of 89:11 favoring the silylation at the mutually meta position. In contrast, borylation of this substrate was completely unselective toward the C—H bonds ortho and meta to the fluorine. Likewise, the reaction of benzodioxole (24a) with L1 afforded the 1,2,4-substituted product because of the steric hindrance at the ortho-position, whereas borylation of the same substrate catalyzed by the iridium system gives predominantly the ortho-functionalized products (Vanchura, et al., *Chem. Commun.* 46:7724-7726 (2010); Borylation of benzodioxole following the procedure in reference 26 afforded a mixture of meta, ortho, and difunctionalized products (92% yield) in a ratio of 6:33:61 (Scheme 3). This discrepancy is likely due to the difference in the amount of the diboron reagent used). Furthermore, we found that a very large substituent such as the OTIPS group severely retarded meta-functionalization and promoted para-functionalization with high selectivities (25-27).

In addition to the steric properties, the electronic properties of the substituents also influence the regioselectivities of reactions of 1,2-disubstituted arenes. For example, silylation of a series of 2-substituted anisoles (28-30) catalyzed by the complex containing L1 predominantly occurred at the more electron-rich position. Despite relatively minor difference in sizes of the substituents, 2-trifluoromethylanisole (28a) underwent silylation at the position para to the OMe group with a selectivity of 98:2. In contrast, the borylation of the same substrate afforded two isomers in a ratio of 31:69 (borylation reaction was carried out according to the literature procedure: Liskey, et al., *J Am. Chem. Soc.* 132:11389-11391 (2010)). When the steric and electronic properties would lead to different isomers, the regioselectivity of the silylation reaction is low. For example, reaction of substrate 33a in which the carbon meta to the amide group is more electron rich yet more sterically hindered led to a mixture of isomers in a ratio of 60:40.

Scheme 3. Silylation of 1,2-disubstituted arenes and fluoroarenes.[a]

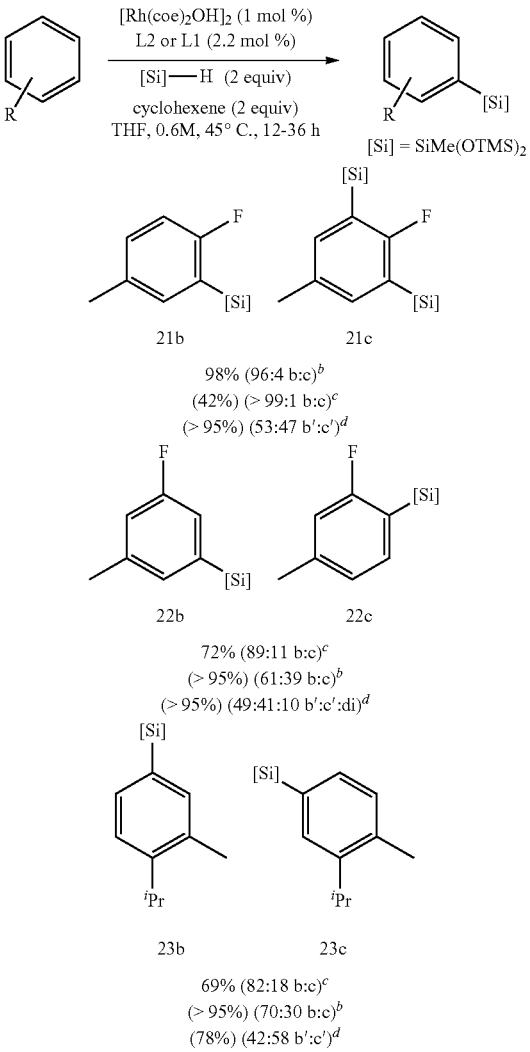

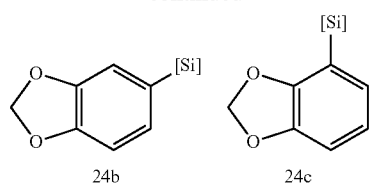

24b     24c (>95%) (41:18:41 b:c:di)[b]
91% (92:8 b:c)[c]
- (4:96 b':c')[e]

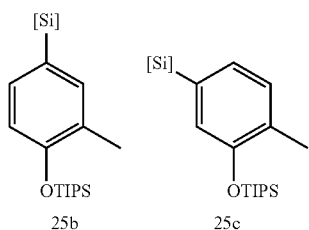

25b     25c

90% (>99:1 b:c)[c]
(>95%) (94:6 b:c)[b]
(81%) (28:72 b':c')[d]

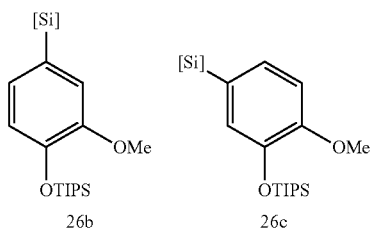

26b     26c (89%) (>99:1 b:c)[c]
(>95%) (>99:1 b:c)[b]
(80%) (51:49 b':c')[d]

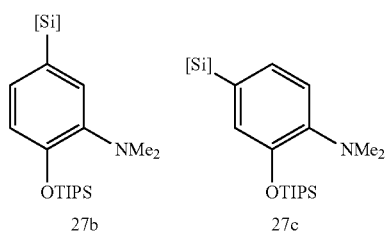

27b     27c (58%) (97:3 b:c)[c]
(75%) (95:5 b:c)[b]
(79%) (54:46 b':c')[d]

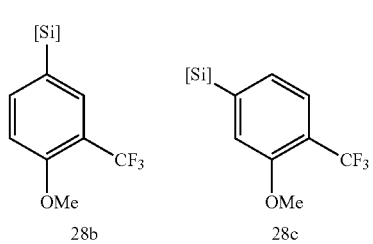

28b     28c

92% (98:2 b:c)[c]
(>95%) (78:22 b:c)[b]
(95%) (31:69 b':c')[d]

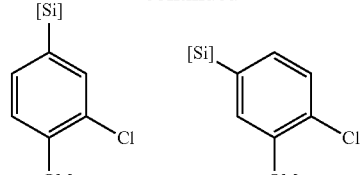

29b     29c

86% (94:6 b:c)[c,f]
(82%) (67:33 b:c)[b]
(94%) (40:60 b':c')[g]

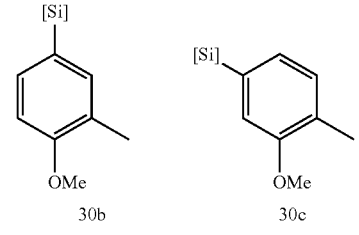

30b     30c

93% (86:14 b:c)[c]
87% (42:58 b:c)[b]
(75%) (25:75 b':c')[g]

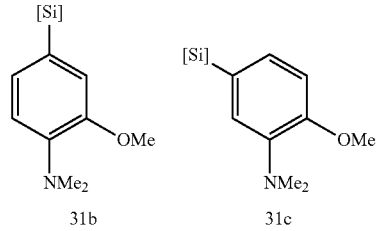

31b     31c (>95%) (70:30 b:c)[c]
(>95%) (61:39 b:c)[b]
(93%) (58:42 b':c')[d]

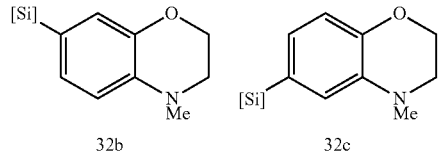

32b     32c (88%) (82:18 b:c)[c]

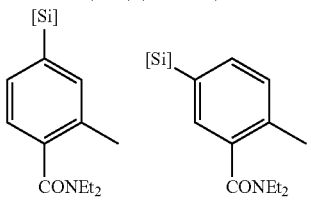

33b     33c (>95%) (60:40 b:c)[b]
(48%) (60:40 b:c)[c]
(>95%) (52:48 b':c')[d]

[a]Reactions conducted on a 0.3 mmol scale unless otherwise stated. Isolated yields of all isomers combined are reported. Yields in parentheses are determined by GC analysis for reactions run on a 0.05 mmol scale. [b]Silylation run with L2 as the ligand. "di" denotes disilylation products. [c]Silylation run with L1 as the ligand. d See reference (borylation reaction was carried out according to the literature procedure: Liskey, et al., J. Am. Chem. Soc. 132:11389-11391 (2010)). "di" denotes diborylation products. [e]Results of borylation of the substrates obtained from reference (Vanchura, et al., Chem. Commun. 46:7724-7726 (2010)). [f]Dechloronated product was also obtained in 9% yield. [g]Results of borylation of the substrates obtained from reference (Tajuddin, et al., Chem. Sci. 3:3505-3515 (2012)).

The influence of the electronic properties of the substituents on the regioselectivity is even more pronounced in the reactions with mono-substituted benzene derivatives. For example, silylation of trifluoromethylbenzene (42a) occurs predominantly at the more electron-rich meta-positions regardless of the choice of the ligand. Similarly, even though the MeO group in 41a is smaller in size than the tert-butyl or trimethylsilyl groups in 43a and 46a, silylation of 41a with L1 afforded more para-functionalized product than silylation of 43a or 46a. Nevertheless, the influence of the size of the ligand on the regioselectivity agrees with our previous observation: reactions run with the more sterically hindered ligand L1 resulted in higher selectivities for silylation at the more sterically accessible site than reactions run with L2. Even reaction of fluorobenzene (48a) with catalyst generated from L1 did not lead to the ortho-functionalized product. Finally, difunctionalized products were not observed from reactions run with L1 as ligand (except for fluorobenzene): this monoselectivity contrasts the selectivities observed for the silylation reactions run with L2 as ligand and for the borylation reactions with the iridium catalyst.

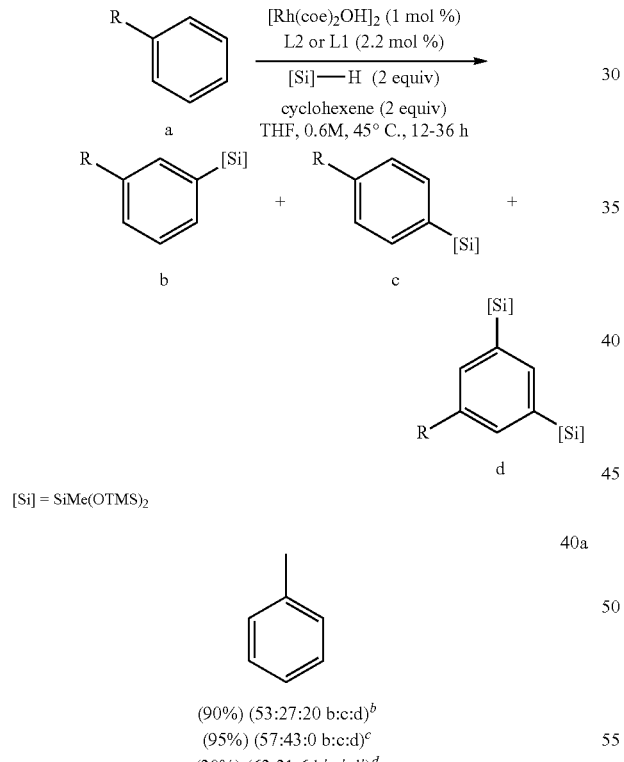

Scheme 4. Silylation of mono-substituted arenes.[a]

[Si] = SiMe(OTMS)$_2$

40a (90%) (53:27:20 b:c:d)[b]
(95%) (57:43:0 b:c:d)[c]
(30%) (63:31:6 b':c':d')[d]

41a

OMe (90%) (57:24:19 b:c:d)[b]
(91%) (21:79:0 b:c:d)[c]
76% (68:16:16 b':c':d')[d]

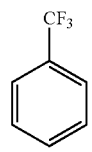

42a

CF$_3$ (>95%) (68:18:14 b:c:d)[b]
(>95%) (78:22:0 b:c:d)[c]
(>99%) (29:31:40 b':c':d')[d]

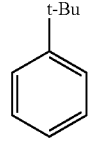

43a t-Bu (89%) (55:45:0 b:c:d)[b]
(78%) (33:67:0 b:c:d)[c]
64% (68:24:8 b':c':d')[d]

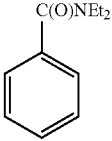

44a

C(O)NEt$_2$ (87%) (69:31:0 b:c:d)[b]
(71%) (41:59:0 b:c:d)[c]
(>95%) (27:28:45)[e]

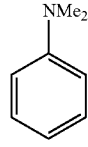

45a

NMe$_2$ (82%) (65:30:5 b:c:d)[b]
84% (8:92:0 b:c:d)[c]
53% (75:21:4 b':c':d')[d]

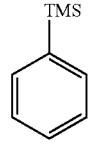

46a

TMS (91%) (51:42:7 b:c:d)[b]
(66%) (33:67:0 b:c:d)[c]
52% (56:28:16 b':c':d')[d]

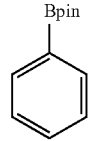

47a

Bpin (49%) (67:33:0 b:c:d)[b]
(69%) (58:42:0 b:c:d)[c]
40% (32:64:4 b':c':d')[d]

-continued

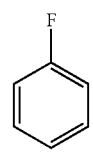

48a (>95%) (18:39:11:32 o:b:c:d)[b]
(>95%) (40:53:7 b:c:d)[c]
(>95%)[e,f]

[a]Reactions conducted on a 0.3 mmol scale unless otherwise stated. Combined isolated yields of all isomers are reported. Yields in parentheses are determined by GC analysis for reactions run on a 0.05 mmol scale. [b]Silylation run with L2 as the ligand. [c]Silylation run with L1 as the ligand. [d]Results of borylation of the substrates obtained from reference (Tajuddin, et al., *Chem. Sci.* 3:3505-3515 (2012)). [e]See reference (borylation reaction was carried out according to the literature procedure: Liskey, et al., *J. Am. Chem. Soc.* 132:11389-11391 (2010)). [f]Borylation of this substrate resulted in a mixture of 3 mono-borylated, 4 di-borylated, and 1 tri-borylated products.

Example 2

Example 2 shows the scope of the iridium-catalyzed silylation of arenes. The functional group compatibility of this iridium-catalyzed C—H silylation of arenes is broad. This method is compatible with ester, ketone, bromide, iodide, nitrile, and sulfone functionalities (Scheme 4). Hydrosilylation of carbonyl groups was not observed, and protodehalogenation was only observed for aryl iodides in 3% yield (7). In addition, the reaction proceeded with high levels of sterically derived regioselectivity. Various 1,3-disubstituted arenes undergo silylation exclusively at the mutually-meta positions, with the exception of 3-CF$_3$-anisole (6) and 3-tolunitrile (1), each affording 4% of the product in which the silyl group was installed ortho to the relatively small OMe and CN groups. However, the selectivities are still higher than that of from the C—H borylation.

Scheme 5. C-H silylation of functionalized arenes.[a]

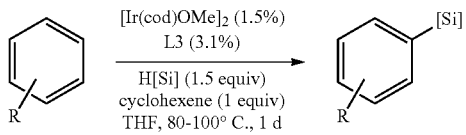

[Ir(cod)OMe]$_2$ (1.5%)
L3 (3.1%)
H[Si] (1.5 equiv)
cyclohexene (1 equiv)
THF, 80-100° C., 1 d 1
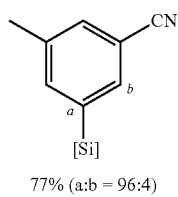
77% (a:b = 96:4)

2
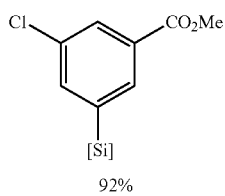
92%

3
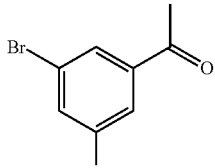
68%

4
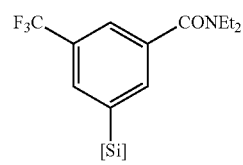
84%

5
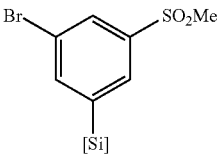
82%

6
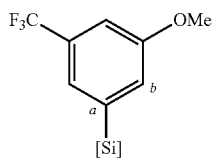
86% (a:b = 96:4)

7
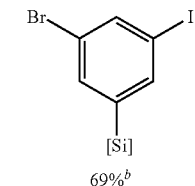
69%[b]

8
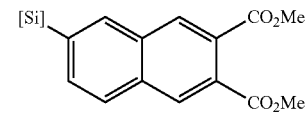
94%

[a]Yields of isolated products. [b]3% of unisolable protodeiodination product was also obtained.

The compatibility of the reaction with heteroarenes, especially those containing basic-nitrogen atoms, was then evaluated. Silylation of potentially coordinating pyrazines, pyrimidines, and azaindoles afforded the corresponding silylarenes in good yields (Scheme 6). Reaction of the more active five-membered heteroarenes required lower temperatures and proceeded with high levels of regioselectivity for the positions α- to the heteroatoms. In cases where the α-positions are substituted or sterically hindered because of a large substituent on the nitrogen, silylation occurred at the β-positions. The free NH group of indoles and pyrroles were not silylated under the reaction conditions, whereas silylation of azaindoles first occurred at the N—H bond. Subsequent silylation at the C—H bond and hydrolysis of the N—Si bond furnished the desired C—H silylation product.

Scheme 6. C-H silylation of heteroarenes.[a]

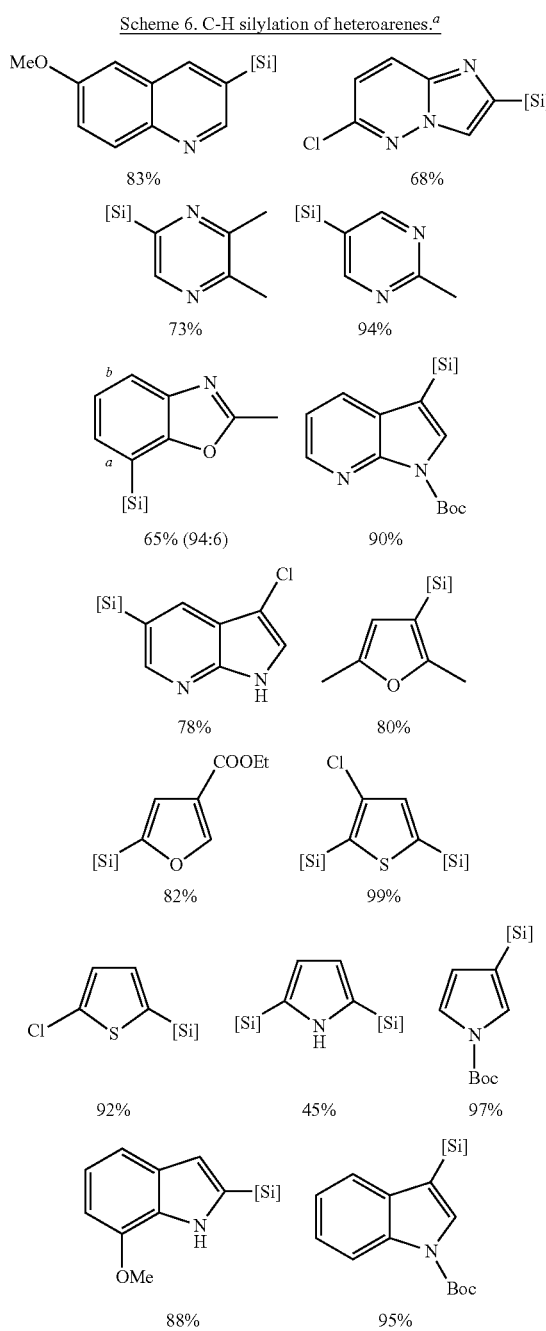

[a]Reactions conducted under conditions similar to the conditions in Scheme 4.

Unless otherwise stated, the silylation of arenes was conducted on a 0.3 mmol scale. To a solution of [Ir(cod)OMe]2 (3.0 mg, 4.5 μmol) and L3 (2.1 mg, 9.3 μmol) in THF (300 mg) in a 20-mL vial was added the desired amount of HSiMe(OSiMe$_3$)$_2$, cyclohexene, and substrate, and the mixture was heated to the desired temperature for 24-48 h. Purification methods are detailed below.

Synthesis of Ligands

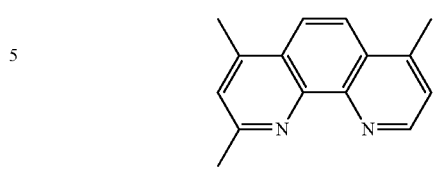

2,4,7-Trimethyl-1,10-phenanthroline (L3): To a stirring suspension of 4,7-dimethyl-1,10-phenanthroline (1.00 g, 4.80 mmol) in dry THF (10 mL) at 0° C. was added drop wise MeLi (3.0 mL of 1.6 M ethereal solution), and the mixture was stirred at room temperature for 16 h. The mixture was then cooled to 0° C. and quenched with water (10 mL). The organic solvents were evaporated, and the aqueous layer was extracted with ethyl acetate (15 mL×3). To the organic layer was added MnO$_2$ (5.0 g, 58 mmol), and the mixture was stirred vigorously at room temperature for 1.5 h. The mixture was dried with MgSO4, filtered, and solvents were evaporated. The crude product was purified by flash column chromatography (2:8 acetone:hexanes→100% acetone) to afford the product as a colorless solid (505 mg, 47% yield). $^1$H NMR (600 MHz, CDCl$_3$) δ 9.04 (d, J=4.4 Hz, 1H), 7.95 (q, J=9.2 Hz, 2H), 7.41 (d, J=4.4 Hz, 1H), 7.34 (s, 1H), 2.89 (s, 3H), 2.76 (s, 3H), 2.72 (s, 3H). $^{13}$C NMR (151 MHz, CDCl$_3$) δ 159.12 (s), 150.01 (s), 146.07 (s), 145.99 (s), 144.17 (s), 144.16 (s), 128.04 (s), 126.02 (s), 124.70 (s), 123.81 (s), 122.10 (s), 121.08 (s), 25.88 (s), 19.21 (s), 19.08 (s).

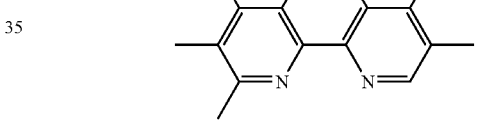

2,3,4,7,8-Pentamethyl-1,10-phenanthroline (L4): This ligand was synthesized from 3,4,7,8-tetramethyl-1,10-phenanthroline (0.93 g, 4.2 mmol) and MeLi according to the procedure for the synthesis of L3. The product was obtained as a colorless solid (338 mg, 32% yield). $^1$H NMR (600 MHz, C$_6$D$_6$) δ 8.93 (s, 1H), 7.95 (q, J=9.4 Hz, 2H), 2.89 (s, 3H), 2.66 (s, 3H), 2.64 (s, 3H), 2.50 (s, 3H), 2.45 (s, 3H). $^{13}$C NMR (151 MHz, CDCl$_3$) δ 158.26 (s), 151.72 (s), 144.81 (s), 143.85 (s), 141.30 (s), 140.86 (s), 130.16 (s), 129.59 (s), 126.91 (s), 125.79 (s), 122.38 (s), 121.02 (s), 25.53 (s), 17.65 (s), 16.07 (s), 14.92 (s), 14.61 (s).

2-Methyl-4,7-dimethoxy-1,10-phenanthroline (L5): This ligand was synthesized from 4,7-dimethoxy-1,10-phenanthroline (240 mg, 1.0 mmol) and MeLi according to the procedure for the synthesis of L3. The product was obtained as a colorless solid (45.6 mg, 18% yield). $^1$H NMR (600 MHz, C$_6$D$_6$) δ 9.02 (d, J=5.3 Hz, 1H), 8.11 (q, J=9.2 Hz, 2H), 6.96 (d, J=5.3 Hz, 1H), 6.87 (s, 1H), 4.07 (s, 3H), 4.05

(s, 3H), 2.88 (s, 3H). $^{13}$C NMR (151 MHz, C$_6$D$_6$) δ 162.49 (s), 162.45 (s), 160.62 (s), 151.11 (s), 146.42 (s), 146.24 (s), 121.20 (s), 119.39 (s), 119.13 (s), 118.03 (s), 103.17 (s), 102.64 (s), 55.95 (s), 55.84 (s), 26.45 (s).

Silylation

Unless otherwise stated, the silylation of arenes was conducted on a 0.3 mmol scale. To a solution of [Ir(cod)OMe]$_2$ (3.0 mg, 4.5 μmol) and L3 (2.1 mg, 9.3 μmol) in THF (300 mg) in a 20-mL vial was added the desired amount of HSiMe(OSiMe$_3$)$_2$, cyclohexene, and substrate, and the mixture was heated to the desired temperature for 24-48 h. Purification methods are detailed below.

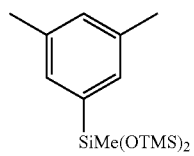

From 1,3-xylene (61.7 μL, 0.5 mmol), 1.5 equiv silane, 100° C., 2 d. purified by preparative TLC (hexanes) to afford the product as a colorless liquid (59.6 mg, 37% yield). $^1$H NMR (500 MHz, CDCl$_3$) δ 7.20 (s, 2H), 7.05 (s, 1H), 2.35 (s, 6H), 0.29 (s, 3H), 0.15 (s, 18H). $^{13}$C NMR (126 MHz, CDCl$_3$) δ 138.39 (s), 136.92 (s), 131.19 (d, J=13.3 Hz), 21.54 (s), 2.05 (s), 0.34 (s). The NMR spectra agree with the literature data.[7]

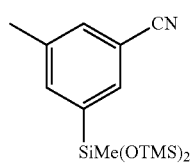

From 3-methylbenzonitrile (35.6 μL, 0.300 mmol), 1.5 equiv silane, 100° C. 2 d. purified by preparative TLC (1:9 ethyl acetate:hexanes) to afford the product A as a colorless liquid (78 mg, 77% yield, isomeric purity determined by GC: 96%). $^1$H NMR (400 MHz, CDCl$_3$) δ 7.61 (s, 1H), 7.55 (s, 1H), 7.46 (s, 1H), 2.39 (s, 3H), 0.27 (s, 3H), 0.12 (s, 18H). $^{13}$C NMR (101 MHz, CDCl$_3$) δ 140.37 (s), 138.29 (s), 138.16 (s), 134.12 (s), 133.26 (s), 119.49 (s), 111.91 (s), 21.28 (s), 1.92 (s), −0.06 (s). HRMS (EI+) calcd for [C$_{14}$H$_{24}$NO$_2$Si$_3$.] (M−CH$_3$): 322.1115, found: 322.1121.

From N,N-diethyl-3-(trifluoromethyl)benzamide (73.6 mg, 0.300 mmol), 1.5 equiv silane, 100° C., 2 d. purified by preparative TLC (3:7 ethyl acetate:hexanes) to afford the product B as a colorless liquid (117 mg, 84% yield). $^1$H NMR (400 MHz, CDCl$_3$) δ 7.79 (s, 1H), 7.68 (s, 1H), 7.62 (s, 1H), 3.54 (bs, 2H), 3.19 (bs, 2H), 1.24 (bs, 3H), 1.10 (s, 3H), 0.27 (s, 3H), 0.09 (s, 18H). $^{13}$C NMR (101 MHz, CDCl$_3$) δ 170.22 (s), 140.59 (s), 137.19 (s), 134.18 (s), 130.48 (q, J=3.4 Hz), 130.21 (q, J=32.2 Hz), 124.34 (q, J=3.6 Hz), 124.09 (q, J=272.7 Hz), 43.42 (s), 39.51 (s), 14.25 (s), 12.91 (s), 1.85 (s), −0.05 (s). $^{19}$F NMR (470 MHz, C$_6$D$_6$) δ −63.06 (s). HRMS (EI+) calcd for [C$_{19}$H$_{34}$F$_3$NO$_3$Si$_3$]: 465.1799, found: 465.1786.

From methyl 3-chlorobenzoate (51.4 mg, 0.301 mmol), 1.5 equiv silane, 100° C., 1 d. purified by preparative TLC (1:9 ethyl acetate:hexanes) to afford the product as a colorless liquid (108 mg, 92% yield). $^1$H NMR (400 MHz, CDCl$_3$) δ 8.10 (s, 1H), 8.04-7.97 (t, J=1.8 Hz, 1H), 7.67 (d, J=1.5 Hz, 1H), 3.92 (s, 3H), 0.29 (s, 3H), 0.13 (s, 18H). $^{13}$C NMR (101 MHz, CDCl$_3$) δ 166.24 (s), 141.69 (s), 137.52 (s), 134.42 (s), 132.47 (s), 131.29 (s), 130.52 (s), 52.43 (s), 1.93 (s), −0.01 (s). HRMS (EI+) calcd for [C$_{14}$H$_{24}$ClO$_4$Si$_3$.] (M−CH$_3$): 375.0671, found: 375.0671.

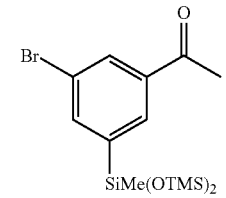

From 1-(3-bromophenyl)ethan-1-one (59.0 mg, 0.296 mmol), 1.2 equiv silane, 80° C., 2 d. purified by preparative TLC (1:9 ethyl acetate:hexanes) to afford the product C as a colorless liquid (84 mg, 68% yield). $^1$H NMR (400 MHz, CDCl$_3$) δ 8.08 (t. J=1.8 Hz, 1H), 8.03 (t. J=1.0 Hz, 1H), 7.82 (dd, J=1.8, 0.6 Hz, 1H), 2.59 (s, 3H), 0.29 (s, 3H), 0.13 (s, 18H). $^{13}$C NMR (101 MHz, CDCl$_3$) δ 197.01 (s), 142.31 (s), 140.52 (s), 138.23 (s), 132.16 (s), 131.52 (s), 123.24 (s), 26.74 (s), 1.97 (s), 0.04 (s). HRMS (EI+) calcd for [C$_{14}$H$_{24}$BrO$_3$Si$_3$.] (M−CH$_3$): 403.0217, found: 403.0216.

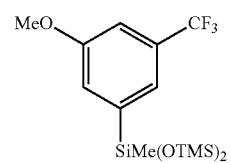

From 1-methoxy-3-(trifluoromethyl)benzene (52.2 mg, 0.296 mmol), 1.5 equiv silane, 100° C., 1 d. purified by flash column chromatography (hexanes) to afford the product D as a colorless liquid (101 mg, 86% yield, isomeric purity determined by GC and NMR: 96%). 1H NMR (600 MHz, CDCl$_3$) δ 7.40 (s, 1H), 7.27 (s, 1H), 7.14 (s, 1H), 3.87 (s, 3H), 0.31 (s, 3H), 0.15 (s, 18H). $^{13}$C NMR (151 MHz, CDCl$_3$) δ 159.22 (s), 141.68 (s), 131.42 (q, J=31.5 Hz), 124.37 (q, J=272.5 Hz), 122.37 (s), 122.07 (q, J=3.8 Hz), 111.53 (d, J=3.7 Hz), 55.48 (s), 1.95 (s), 0.03 (s). $^{19}$F NMR (565 MHz, CDCl$_3$) δ −63.65 (s). HRMS (EI+) calcd for [C$_{15}$H$_{27}$F$_3$O$_3$Si$_3$]: 396.1220, found: 396.1218.

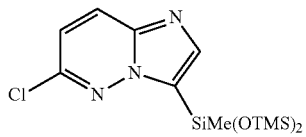

From 6-chloroimidazo[1,2-b]pyridazine (46.1 mg, 0.300 mmol), 1.2 equiv silane, 100° C., 1 d. purified by preparative TLC (3:7 ethyl acetate:hexanes) to afford the product E as a colorless liquid (84 mg, 68% yield). $^1$H NMR (600 MHz, CDCl$_3$) δ 7.89 (d, J=9.4 Hz, 1H), 7.82 (s, 1H), 7.03 (d, J=9.4 Hz, 1H), 0.39 (s, 3H), 0.10 (s, 18H). $^{13}$C NMR (151 MHz. CDCl$_3$) δ 146.22 (s), 142.83 (s), 140.18 (s), 127.94 (s), 126.74 (s), 119.07 (s), 1.81 (s), 0.49 (s). HRMS (EI+) calcd for [C$_{13}$H$_{24}$ClN$_3$O$_2$Si$_3$]: 373.0865, found: 373.0861.

From 3-bromoiodobenzene (83.9 mg, 0.297 mmol), 1.2 equiv silane, 100° C. 2 d. purified by preparative TLC (hexamethyldisiloxane) to afford the product K as a colorless liquid (103 mg, 69% yield, contains 3% inseparable de-iodination product). $^1$H NMR (400 MHz, C$_6$D$_6$) δ 7.87 (t, J=1.7 Hz, 1H), 7.76 (dd. J=1.5, 0.6 Hz, 1H), 7.59 (dd, J=1.8, 0.6 Hz, 1H), 0.27 (s, 3H), 0.13 (s, 18H). $^{13}$C NMR (101 MHz. C$_6$D$_6$) δ 144.23 (s), 140.61 (s), 140.42 (s), 135.16 (s), 123.27 (s), 95.31 (s), 1.99 (s), −0.04 (s). HRMS (EI+) calcd for [C$_3$H$_{24}$BrIO$_2$Si$_3$]: 501.9312, found: 501.9315.

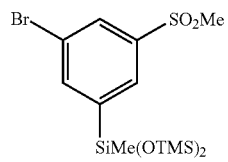

From 1-bromo-3-(methylsulfonyl)benzene (73.3 mg, 0.312 mmol), 1.3 equiv silane, 80° C., 1 d. purified by preparative TLC (3:7 ethyl acetate:hexanes) to afford the product F as a colorless liquid (116 mg, 82% yield). $^1$H NMR (400 MHz, CDCl$_3$) δ 8.06 (t. J=1.8 Hz, 1H), 7.99 (dd, J=1.5, 0.6 Hz, 1H), 7.88 (d, J=1.8, 0.6 Hz, 1H), 3.04 (s, 3H), 0.29 (s, 3H), 0.12 (s, 18H). $^{13}$C NMR (101 MHz, CDCl$_3$) δ 143.85 (s), 141.77 (s), 141.22 (s), 131.00 (s), 130.23 (s), 123.40 (s), 44.60 (s), 1.92 (s), −0.08 (s). HRMS (EI+) calcd for [C$_{13}$H$_{24}$BrO$_4$SSi$_3$.] (M−CH$_3$): 438.9886, found: 438.9882.

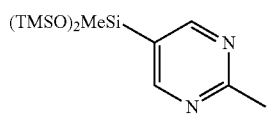

From 2-methylpyrimidine (28.9 mg, 0.307 mmol), 1.5 equiv silane, 100° C. 1 d. The resulting mixture was purified by Kugelrohr distillation to afford the product as a colorless liquid (90.8 mg, 94% yield). $^1$H NMR (400 MHz, CDCl$_3$) δ 8.66 (s, 2H), 2.70 (s, 3H), 0.27 (s, 3H), 0.10 (s, 18H). $^{13}$C NMR (101 MHz, CDCl$_3$) δ 168.72 (s), 161.58 (s), 126.68 (s), 26.30 (s), 1.92 (s), 0.38 (s). HRMS (EI+) calcd for [C$_{12}$H$_{26}$N$_2$O$_2$Si$_3$]: 314.1302, found: 314.1302.

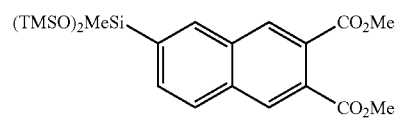

From dimethyl 2,3-naphthalenedicarboxylate (72.9 mg, 0.298 mmol), 2 equiv silane, 100° C., 1 d. The resulting mixture was purified by preparative TLC (2:8 ethyl acetate:hexanes) to afford the product as a light yellow liquid (130.3 mg, 94%). $^1$H NMR (600 MHz, CDCl$_3$) δ 8.29 (s, 1H), 8.24 (s, 1H), 8.13 (s, 1H), 7.90 (d, J=8.1 Hz, 1H), 7.77 (d, J=8.1 Hz, 1H), 3.96 (s, 3H), 3.95 (s, 3H), 0.36 (s, 3H), 0.14 (s, 18H). $^{13}$C NMR (151 MHz, CDCl$_3$) δ 168.28 (s), 168.21 (s), 139.67 (s), 134.66 (s), 134.00 (s), 132.74 (s), 132.40 (s), 130.66 (s), 130.01 (s), 129.00 (s), 128.41 (s), 127.65 (s), 52.73 (s), 1.95 (s), 0.02 (s). HRMS (EI+) calcd for [C$_{21}$H$_{32}$O$_6$Si$_3$]: 464.1507, found: 464.1504.

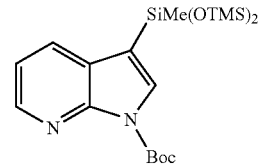

From N-Boc-7-azaindole (62.9 mg, 0.288 mmol), 1.3 equiv silane, 80° C., 1 d. The resulting mixture was purified by preparative TLC (2:8 ethyl acetate:hexanes) to afford the product as a light yellow liquid (113.2 mg, 90% yield). $^1$H NMR (600 MHz, CDCl$_3$) δ 8.45 (d, J=4.0 Hz, 1H), 7.91 (d, J=7.5 Hz, 1H), 7.64 (s, 1H), 7.15 (dd. J=7.7, 4.8 Hz, 1H), 1.63 (s, 9H), 0.30 (s, 3H), 0.08 (s, 18H). $^{13}$C NMR (151 MHz, CDCl$_3$) δ 149.61 (s), 147.82 (s), 144.85 (s), 133.10 (s), 130.13 (s), 126.28 (s), 118.39 (s), 113.07 (s), 83.93 (s), 28.08 (s), 1.87 (s), 1.24 (s). HRMS (ESI+) calcd for [C$_{19}$H$_{35}$N$_2$O$_4$Si$_3$$^+$] (M+H$^+$): 439.1899, found: 439.1896.

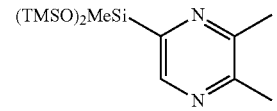

From 2,3-dimethylpyrazine (33.7 mg, 0.311 mmol), 2 equiv silane, 100° C., 1 d. The resulting mixture was purified by flash column chromatography over silica pretreated with Et$_3$N (0→10% ethyl acetate in hexanes) to afford the product as a colorless liquid (74.3 mg, 73% yield). $^1$H NMR (600 MHz. CDCl$_3$) δ 8.40 (s, 1H), 2.52 (s, 3H), 2.49 (s, 3H), 0.29 (s, 3H), 0.09 (s, 18H). $^{13}$C NMR (151 MHz, CDCl$_3$) δ 155.30 (s), 152.88 (s), 151.89 (s), 145.44 (s), 22.40 (s), 22.34 (s), 1.90 (s), −0.62 (s). HRMS (EI+) calcd for [C$_3$H$_{28}$N$_2$O$_2$Si$_3$]: 328.1459, found: 328.1457.

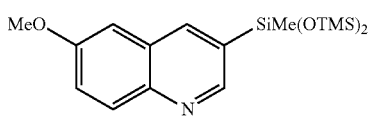

From 6-methoxyquinoline (48.0 mg, 0.302 mmol), 2 equiv silane, 100° C., 1 d. The resulting mixture was purified by preparative TLC (2:8 ethyl acetate:hexanes) to afford the product G as a light yellow liquid (95.2 mg, 83% yield). $^1$H NMR (400 MHz, CDCl$_3$) δ 8.86 (d, J=1.5 Hz, 1H), 8.19 (s, 1H), 7.97 (d, J=9.2 Hz, 1H), 7.36 (dd, J=9.2, 2.8 Hz, 1H), 7.06 (d, J=2.7 Hz, 1H), 3.91 (s, 3H), 0.36 (s, 3H), 0.13 (s, 18H). $^{13}$C NMR (101 MHz, CDCl$_3$) δ 157.73 (s), 151.50 (s), 144.76 (s), 141.07 (s), 131.16 (s), 130.78 (s), 128.64 (s), 122.84 (s), 105.34 (s), 55.58 (s), 1.97 (s), 0.31 (s). HRMS (EI+) calcd for [C$_{17}$H$_{29}$NO$_3$Si$_3$]: 379.1455, found: 379.1456.

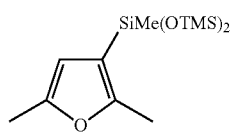

From 2,5-dimethylfuran (30.8 mg, 0.320 mmol), 1.5 equiv silane, 80° C., 1 d. The volatile materials were evaporated, and the resulting mixture was diluted with hexanes and filtered over a pad of silica to afford the product as a colorless liquid (81.6 mg, 80% yield). $^1$H NMR (400 MHz, CDCl$_3$) δ 5.83 (d, J=0.6 Hz, 1H), 2.32 (s, 3H), 2.25 (s, 3H), 0.21 (s, 3H), 0.13 (s, 18H). $^{13}$C NMR (101 MHz, CDCl$_3$) δ 156.04 (s), 149.75 (s), 112.94 (s), 110.01 (s), 14.30 (s), 13.27 (s), 2.00 (s), 1.45 (s). HRMS (EI+) calcd for [C$_{13}$H$_{28}$O$_3$Si$_3$]: 316.1346, found: 316.1343.

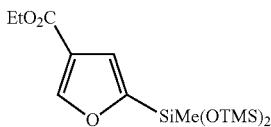

From ethyl 3-furoate (45.3 mg, 0.323 mmol), 1.2 equiv silane, 65° C., 1 d. The resulting mixture was purified by preparative TLC (1:9 ethyl acetate:hexanes) to afford the product as a colorless liquid (95.1 mg, 82% yield). $^1$H NMR (400 MHz, CDCl$_3$) δ 8.15 (s, 1H), 6.96 (s, 1H), 4.28 (q, J=7.1 Hz, 2H), 1.33 (t, J=7.1 Hz, 3H), 0.26 (s, 3H), 0.09 (s, 18H). $^{13}$C NMR (101 MHz, CDCl$_3$) δ 163.54 (s), 160.15 (s), 151.31 (s), 119.78 (s), 119.49 (s), 60.44 (s), 14.45 (s), 1.75 (s), −0.12 (s). HRMS (EI+) calcd for [C$_{14}$H$_2$O$_5$Si$_3$]: 360.1245, found: 360.1244.

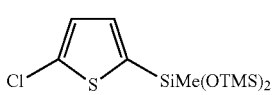

From 2-chlorothiophene (37.1 mg, 0.312 mmol), 1.0 equiv silane, 65° C., 1 d. The volatile materials were evaporated, and the resulting mixture was diluted with hexanes and filtered over a pad of silica to afford the product as a colorless liquid (97.9 mg, 92% yield). $^1$H NMR (400 MHz, CDCl$_3$) δ 7.06 (d, J=2.1 Hz, 1H), 6.95 (d, J=2.1 Hz, 1H), 0.31 (s, 3H), 0.14 (s, 18H). $^{13}$C NMR (101 MHz, CDCl$_3$) δ 138.36 (s), 134.96 (s), 133.98 (s), 127.38 (s), 1.93 (s), 1.01 (s). HRMS (EI+) calcd for [C$_{11}$H$_{23}$ClO$_2$SSi$_3$]: 338.0415, found: 338.0414.

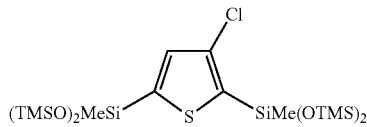

From 3-chlorothiophene (40.9 mg, 0.345 mmol), 2.5 equiv silane, 80° C., 1 d. The volatile materials were evaporated, and the resulting mixture was diluted with hexanes and filtered over a pad of silica to afford the product as a colorless liquid (192.6 mg, 99% yield). $^1$H NMR (600 MHz. CDCl$_3$) δ 7.15 (s, 1H), 0.41 (s, 3H), 0.33 (s, 3H), 0.17 (s, 18H), 0.16 (s, 18H). $^{13}$C NMR (151 MHz, CDCl$_3$) δ 144.34 (s), 136.76 (s), 136.17 (s), 131.83 (s), 1.95 (s), 1.91 (s), 1.09 (s), 1.00 (s). HRMS (EI+) calcd for [C$_{18}$H$_{43}$ClO$_4$SSi$_6$]: 558.1186, found: 558.1185.

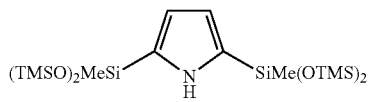

From pyrrole (19.1 mg, 0.285 mmol), 2.5 equiv silane, 80° C. 1 d. The resulting mixture was purified by flash column chromatography (0→15% ethyl acetate in hexanes) to afford the product as a colorless liquid (64.6 mg, 45% yield). $^1$H NMR (600 MHz, CDCl$_3$) δ 8.45 (s, 1H), 6.50 (s, 2H), 0.30 (s, 6H), 0.13 (s, 36H). $^{13}$C NMR (151 MHz, CDCl$_3$) δ 132.72 (s), 118.03 (s), 1.95 (s), 0.96 (s). HRMS (EI+) calcd for [C$_{15}$H$_{45}$NO$_4$Si$_6$]: 507.1964, found: 507.1970.

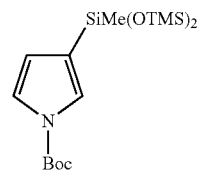

From N-Boc-pyrrole (51.9 mg, 0.310 mmol), 1.3 equiv silane, 80° C., 1 d. The resulting mixture was purified by flash column chromatography (0→10% ethyl acetate in hexanes) to afford the product as a colorless liquid (117 mg, 97% yield). $^1$H NMR (600 MHz, CDCl$_3$) δ 7.31 (s, 1H), 7.26 (s, 1H), 6.27 (dd, J=2.9, 1.4 Hz, 1H), 1.61 (s, 9H), 0.23 (s, 3H), 0.12 (s, 18H). $^{13}$C NMR (151 MHz, CDCl$_3$) δ 148.98 (s), 126.34 (s), 121.20 (s), 120.83 (s), 115.94 (s), 83.62 (s), 28.09 (s), 1.99 (s), 1.00 (s). HRMS (EI+) calcd for [C$_{16}$H$_{33}$NO$_4$Si$_3$]: 387.1717, found: 387.1714.

c

From 2-methylbenzoxazole (40.1 mg, 0.301 mmol), 1.2 equiv silane, 80° C., 1 d. The resulting mixture was purified by preparative TLC (2:8 ethyl acetate:hexanes) to afford the product as a colorless liquid (69.0 mg, 65% yield, b:c=94:6). $^1$H NMR (600 MHz, CDCl$_3$) b 7.67 (d, J=7.8 Hz, 1H), 7.42 (d, J=7.1 Hz, 1H), 7.28 (t, J=7.5 Hz, 1H), 2.64 (s, 3H), 0.39 (s, 3H), 0.11 (s, 18H). $^{13}$C NMR (151 MHz, CDCl$_1$) δ 163.71 (s), 155.05 (s), 140.29 (s), 129.90 (s), 123.89 (s), 120.87 (s), 120.47 (s), 14.70 (s), 1.89 (s), 0.94 (s). HRMS (EI+) calcd for [C$_{15}$H$_{27}$NO$_3$Si$_3$]: 353.1299, found: 353.1298.

From 7-methoxyindole (43.7 mg, 0.297 mmol), 1.2 equiv silane, 65° C., 1 d. The resulting mixture was purified by preparative TLC (1:9 ethyl acetate:hexanes) to afford the product as a colorless liquid (96.5 mg, 88% yield). $^1$H NMR (400 MHz, CDCl$_3$) δ 8.46 (s, 1H), 7.34 (d, J=8.0 Hz, 1H), 7.09 (t, J=7.8 Hz, 1H), 6.82 (d, J=2.2 Hz, 1H), 6.70 (d, J=7.6 Hz, 1H), 4.03 (s, 3H), 0.43 (s, 3H), 0.23 (s, 18H). $^{13}$C NMR (101 MHz. CDCl$_3$) δ 146.35 (s), 135.84 (s), 130.01 (s), 129.01 (s), 120.12 (s), 113.70 (s), 111.84 (s), 102.05 (s), 55.38 (s), 1.99 (s), 0.87 (s). The spectra match the ones reported.[7]

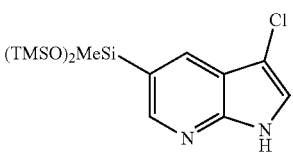

From 1-boc-indole (64.9 mg, 0.299 mmol), 1.2 equiv silane, 80° C., 1 d. The resulting mixture was purified by preparative TLC (1:9 ethyl acetate:hexanes) to afford the product as a colorless liquid (124 mg, 95% yield). $^1$H NMR (600 MHz, CDCl$_3$) δ 8.18 (s, 1H), 7.72 (d, J=7.9 Hz, 2H), 7.35 (t, J=7.6 Hz, 1H), 7.28 (t, J=7.4 Hz, 1H), 1.72 (s, 9H), 0.40 (s, 3H), 0.19 (s, 18H). $^{13}$C NMR (151 MHz, CDCl$_3$) δ 149.80 (s), 136.38 (s), 133.95 (s), 132.92 (s), 124.12 (s), 122.63 (s), 122.36 (s), 115.70 (s), 115.20 (s), 83.70 (s), 28.29 (s), 2.04 (s), 1.48 (s). HRMS (EI+) calcd for [C$_{20}$H$_{35}$NO$_4$Si$_3$]: 437.1874, found: 437.1878.

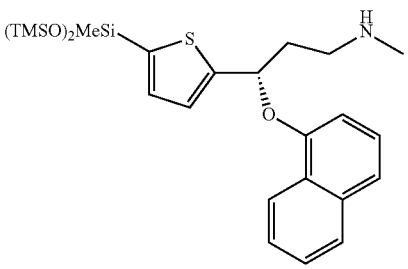

To [Ir(cod)OMe]$_2$ (2.0 mg, 3.0 μmol) and 2,4,7-trimethylphenanthroline (1.4 mg, 6.3 μmol) in a 4-mL vial was added THF (200 mg), HSiMe(OTMS)$_2$ (73.5 μL, 0.260 mmol, 1.3 equiv), cyclohexene (20 μL, 0.20 mmol), and clopidogrel (64.8 mg, 0.201 mmol). The mixture was heated at 80° C. for 14 h. The resulting mixture was cooled to room temperature and purified by preparative TLC (2:8 ethyl acetate:hexanes) to afford the product as a colorless viscous liquid (96.0 mg, 88% yield). $^1$H NMR (400 MHz, CDCl$_3$) δ 7.73 (dd, J=7.4, 1.6 Hz, 1H), 7.47-7.38 (m, 1H), 7.34-7.23 (m, 2H), 6.88 (s, 1H), 4.94 (s, 1H), 3.80 (d, J=14.0 Hz, 1H), 3.74 (s, 3H), 3.66 (d, J=14.1 Hz, 1H), 3.00-2.83 (m, 4H), 0.28 (s, 3H), 0.13 (s, 18H). $^{13}$C NMR (101 MHz, CDCl$_3$) δ 171.46 (s), 139.05 (s), 135.56 (s), 134.79 (s), 134.66 (s), 134.00 (s), 132.93 (s), 130.10 (s), 129.88 (s), 129.51 (s), 127.27 (s), 68.04 (s), 52.26 (s), 50.80 (s), 48.41 (s), 25.91 (s), 1.95 (s), 1.26 (s). HRMS (EI+) calcd for [C$_{23}$H$_{36}$ClNO$_4$SSi$_3$]: 541.1361, found: 541.1348.

From 3-chloro-7-azaindole (45.3 mg, 0.297 mmol), 2.5 equiv silane, 100° C., 1 d. After the reaction, the volatile materials were evaporated, and the residue was dissolved in ethyl acetate (7 mL). To the solution was added methanol (1 mL) and saturated aqueous NaHCO$_3$ solution (2 mL), and the mixture was stirred vigorously at room temperature for 5 h. The organic layer was separated, and the aqueous layer was extracted with ethyl acetate (2×2 mL). The combined organic layer was washed with brine and dried over MgSO$_4$. The solvents were evaporated, and the residue was purified by preparative TLC (3:7 ethyl acetate:hexanes) to afford the product as a light yellow solid (86.3 mg, 78% yield). $^1$H NMR (400 MHz, CDCl$_3$) δ 12.58 (s, 1H), 8.53 (d, J=1.2 Hz, H), 8.19 (d, J=1.3 Hz, 1H), 7.38 (s, 1H), 0.41 (s, 3H), 0.19 (s, 18H). $^{13}$C NMR (101 MHz, CDCl$_3$) δ 148.04 (s), 147.56 (s), 132.77 (s), 124.65 (s), 122.14 (s), 118.40 (s), 104.58 (s), 2.08 (s), 0.70 (s). HRMS (EI+) calcd for [C$_{14}$H$_{25}$ClN$_2$O$_2$Si$_3$]: 372.0912, found: 372.0911.

To [Ir(cod)OMe]$_2$ (2.0 mg, 3.0 μmol) and 2,4,7-trimethylphenanthroline (1.4 mg, 6.3 μmol) in a 4-mL vial was added THF (200 mg), HSiMe(OTMS)$_2$ (130 μL, 0.460 mmol, 2.3 equiv), cyclohexene (40 μL, 0.40 mmol), and duloxetine (59.2 mg, 0.199 mmol). The mixture was heated at 80° C. for 16 h. The resulting mixture was cooled to room temperature and purified by preparative TLC (pure ethyl acetate on a TLC plate pre-treated with Et$_3$N) to afford the product as a yellow viscous liquid (89.1 mg, 86% yield). $^1$H NMR (500 MHz, CDCl$_3$) δ 8.41 (dd, J=6.1, 3.3 Hz, 1H), 7.80 (dd, J=5.9, 3.3 Hz, 1H), 7.55-7.46 (m, 2H), 7.41 (d, J=8.2 Hz, 1H), 7.29 (t, J=8.0 Hz, 1H), 7.15 (d, J=3.3 Hz, 1H), 7.11 (d, J=3.3 Hz, 1H), 6.88 (d, J=7.7 Hz, 1H), 5.82 (dd, J=7.5, 5.2 Hz, 1H), 2.85 (td, J=6.8, 3.0 Hz, 2H), 2.53-2.46 (m, 1H), 2.45 (s, 3H), 2.27 (dt, J=6.8, 6.3 Hz, 1H), 1.30 (s, 1H), 0.31 (s, 3H), 0.10 (d, J=1.6 Hz, 18H). $^{13}$C NMR (101 MHz, CDCl$_3$) δ 153.58 (s), 150.61 (s), 137.68 (s), 134.66 (s), 134.36 (s), 127.55 (s), 126.36 (s), 126.28 (s), 125.83 (s), 125.62 (s), 125.30 (s), 122.31 (s), 120.64 (s), 107.29 (s), 75.03 (s), 48.46 (s), 39.12 (s), 36.70 (s), 1.85 (s), 1.07 (s). HRMS (ESI+) calcd for [C$_{25}$H$_{40}$NO$_3$SSi$_3^+$]: 518.2031, found: 518.2031.

1 d. The resulting mixture was cooled to room temperature and purified by preparative TLC (5:5 ethyl acetate:hexanes on a TLC plate pre-treated with Et$_3$N) to afford the product as a yellow viscous liquid (79.4 mg, 75% yield). $^1$H NMR (500 MHz, CDCl$_3$) δ 7.32-7.28 (m, 1H), 7.21-7.16 (m, 3H), 7.15 (s, 1H), 4.20 (d, J=13.5 Hz, 1H), 3.74 (d, J=13.5 Hz, 1H), 2.78-2.70 (m, 1H), 2.70-2.59 (m, 3H), 2.48-2.37 (m, 2H), 2.28 (s, 3H), 2.18 (td, J=10.9, 3.9 Hz, 1H), 2.08 (td, J=10.4, 3.1 Hz, 1H), 0.28 (s, 3H), 0.11 (s, 18H). $^{13}$C NMR (126 MHz, CDCl$_3$) δ 189.46 (s), 148.43 (s), 146.01 (s), 141.94 (s), 141.27 (s), 138.30 (s), 136.95 (s), 132.65 (s), 129.57 (s), 129.24 (s), 128.77 (s), 127.23 (s), 126.68 (s), 57.26 (s), 57.21 (s), 49.86 (s), 46.08 (s), 31.61 (s), 31.53 (s), 1.89 (s), 1.00 (s). HRMS (EI+) calcd for [C26H39NO3SSi3]: 529.1958, found: 529.1957.

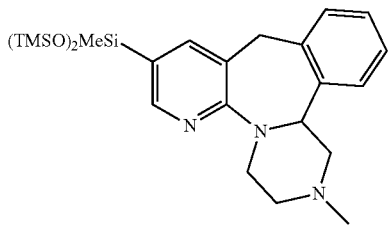

To [Ir(cod)OMe]$_2$ (2.0 mg, 3.0 μmol) and 2,4,7-trimethylphenanthroline (1.4 mg, 6.3 μmol) in a 20-mL vial was added THF (200 mg), HSiMe(OTMS)$_2$ (141 μL, 0.500 mmol, 2.5 equiv), cyclohexene (20 μL, 0.20 mmol), and mirtazapine (53.9 mg, 0.203 mmol). The mixture was heated at 80° C. for 2 d. The resulting mixture was cooled to room temperature and purified by preparative TLC (7:3 ethyl acetate:hexanes on a TLC plate pre-treated with Et$_3$N) to afford the product H as a yellow viscous liquid (45.7 mg, 46% yield). $^1$H NMR (500 MHz, CDCl$_3$) δ 8.27 (s, 1H), 7.39 (s, 1H), 7.20-7.09 (m, 4H), 4.43 (dd, J=23.2, 11.0 Hz, 2H), 3.74 (d, J=12.7 Hz, 1H), 3.49 (dd. J=29.6, 12.1 Hz, 2H), 2.94 (d, J=10.8 Hz, 1H), 2.84 (d, J=10.9 Hz, 1H), 2.55 (t, J=10.3 Hz, 1H), 2.37 (s, 3H), 2.34 (d, J=11.0 Hz, 1H), 0.20 (s, 3H), 0.09 (s, 18H). $^{13}$C NMR (126 MHz, CDCl$_3$) δ 160.16 (s), 151.19 (s), 139.71 (s), 138.24 (s), 137.08 (s), 130.02 (s), 129.72 (s), 128.05 (s), 127.60 (s), 127.04 (s), 125.23 (s), 64.56 (s), 64.16 (s), 55.68 (s), 48.87 (s), 45.98 (s), 38.76 (s), 2.01 (s), 0.56 (s). HRMS (EI+) calcd for [C$_{24}$H$_{39}$N$_3$O$_2$Si$_3$]: 485.2350, found: 485.2355.

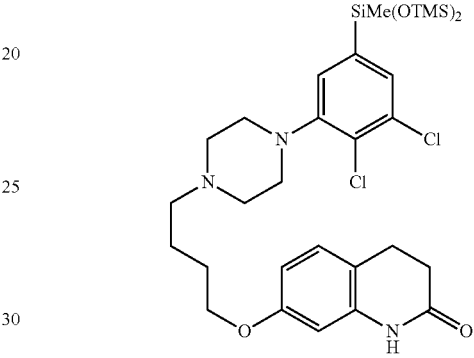

To [Ir(cod)OMe]$_2$ (4.0 mg, 6.0 μmol) and 2,4,7-trimethylphenanthroline (2.8 mg, 13 μmol) in a 20-mL vial was added THF (400 mg), HSiMe(OTMS)$_2$ (222 mg, 1.00 mmol, 5 equiv), cyclohexene (40 μL, 0.40 mmol), and aripiprazole (90.2 mg, 0.201 mmol). The mixture was heated at 100° C. for 1 d. The resulting mixture was cooled to room temperature, and the volatile materials were evaporated. To the residue was added ethyl acetate (5 mL) and saturated NaHCO$_3$ (aq, 2 mL), and the mixture was stirred vigorously for at room temperature for 30 min. The organic layer was separated, and the aqueous layer was extracted with ethyl acetate (2 mL×2). The combined organic layer was washed with brine, dried over MgSO$_4$, filtered, and the solvents were evaporated. The residue was purified by preparative TLC (5:5 ethyl acetate:hexanes on a TLC plate pre-treated with Et$_3$N) to afford the product I as a colorless solid (101 mg, 75% yield). $^1$H NMR (600 MHz, CDCl$_3$) δ 9.40 (s, 1H), 7.27 (d, J=0.9 Hz, 1H), 7.11 (d, J=0.8 Hz, 1H), 7.02 (d, J=8.3 Hz, 1H), 6.51 (dd, J=8.3, 2.4 Hz, 1H), 6.42 (d, J=2.3 Hz, 1H), 3.95 (t, J=6.2 Hz, 2H), 3.08 (bs, 4H), 2.88 (t, J=7.5 Hz, 2H), 2.66 (bs, 4H), 2.64-2.58 (m, 2H), 2.52-2.44 (m, 2H), 1.85-1.77 (m, 1H), 1.75-1.66 (m, 1H), 0.24 (s, 3H), 0.11 (s, 18H). $^{13}$C NMR (151 MHz, CDCl$_3$) δ 172.61 (s), 158.75 (s), 150.63 (s), 138.70 (s), 138.36 (s), 133.72 (s), 129.18 (s), 128.77 (s), 128.60 (s), 122.91 (s), 115.68 (s), 108.80 (s), 102.40 (s), 67.92 (s), 58.33 (s), 53.44 (s), 51.44 (s), 31.15 (s), 27.36 (s), 24.63 (s), 23.56 (s), 1.96 (s), —0.02 (s). HRMS (ESI+) calcd for [C$_{30}$H$_{48}$Cl$_2$N$_3$O$_4$Si$_3$] (M+H$^+$): 668.2324, found: 668.2319.

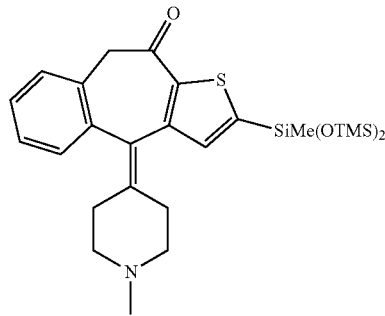

To [Ir(cod)OMe]$_2$ (2.0 mg, 3.0 μmol) and 2,4,7-trimethylphenanthroline (1.4 mg, 6.3 g±mol) in a 4-mL vial was added THF (200 mg), HSiMe(OTMS)$_2$ (68 μL, 0.24 mmol, 1.2 equiv), cyclohexene (20 μL, 0.20 mmol), and ketotifen (62.2 mg, 0.201 mmol). The mixture was heated at 80° C. for

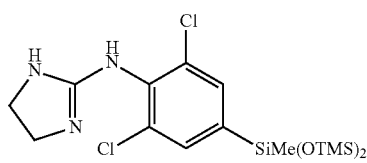

To [Ir(cod)OMe]$_2$ (4.0 mg, 6.0 µmol) and 2,4,7-trimethylphenanthroline (2.8 mg, 13 µmol) in a 20-mL vial was added THF (400 mg), HSiMe(OTMS)$_2$ (266 mg, 1.20 mmol, 6 equiv), cyclohexene (60 µL, 0.60 mmol), and clonidine (46.1 mg, 0.200 mmol). The mixture was heated at 100° C. for 2 d. The resulting mixture was cooled to room temperature, and the volatile materials were evaporated. To the residue was added ethyl acetate (5 mL) and saturated NaHCO$_3$ (aq, 2 mL), and the mixture was stirred vigorously for at room temperature for 30 min. The organic layer was separated, and the aqueous layer was extracted with ethyl acetate (2 mL×2). The combined organic layer was washed with brine, dried over MgSO$_4$, filtered, and the solvents were evaporated. The residue was purified by preparative TLC (5:5 ethyl acetate:hexanes on a TLC plate pre-treated with Et$_3$N) to afford the product as a light brown liquid (78.8 mg, 87% yield). $^1$H NMR (400 MHz, CDCl$_3$) δ 7.38 (s, 2H), 5.18 (bs, 1H), 3.52 (s, 4H), 0.24 (s, 3H), 0.12 (s, 18H). $^{13}$C NMR (101 MHz, CDCl$_3$) δ 157.82 (s), 145.91 (s), 133.58 (s), 132.98 (s), 129.51 (s), 42.58 (s), 1.97 (s), 0.15 (s). HRMS (ESI+) calcd for [C$_{16}$H$_{30}$Cl$_2$N$_3$O$_2$Si$_3$$^+$]: 450.1017, found: 450.1024.

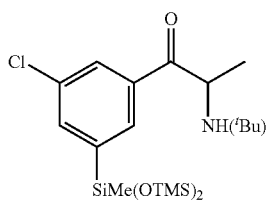

To [Ir(cod)OMe]$_2$ (2.0 mg, 3.0 µmol) and 2,4,7-trimethylphenanthroline (1.4 mg, 6.3 mol) in a 20-mL vial was added THF (300 mg). HSiMe(OTMS)$_2$ (74 µL, 0.26 mmol, 1.3 equiv), cyclohexene (20 µL, 0.20 mmol), and bupropion (49.2 mg, 0.205 mmol). The mixture was heated at 100° C. for 1 d. The resulting mixture was cooled to room temperature and purified by preparative TLC (2:8 ethyl acetate:hexanes on a TLC plate pre-treated with Et$_3$N) to afford the product as a brown liquid (64.7 mg, 69% yield). The product and the starting material slowly oxidize under air and should be stored under an inert atmosphere. $^1$H NMR (500 MHz, CDCl$_3$) δ 8.01 (s, 1H), 7.94 (s, 1H), 7.67 (s, 1H), 4.31 (q, J=7.0 Hz, 1H). 2.40 (bs, 1H), 1.25 (d, J=7.1 Hz, 3H), 1.04 (s, 9H), 0.30 (s, 3H), 0.12 (s, 18H). $^{13}$C NMR (126 MHz. CDCl$_3$) δ 204.27 (s), 142.18 (s), 137.80 (s), 136.07 (s), 135.13 (s), 130.97 (s), 129.30 (s), 52.32 (s), 50.94 (s), 29.84 (s), 22.65 (s), 1.98 (s), 0.04 (s). HRMS (ESI+) calcd for [C$_{20}$H$_{39}$ClNO$_3$Si$_3$$^+$]: 460.1921, found: 460.1924.

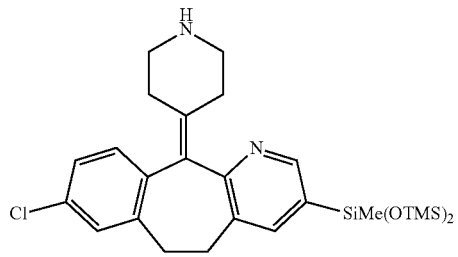

To [Ir(cod)OMe]$_2$ (4.0 mg, 6.0 µmol) and 2,4,7-trimethylphenanthroline (2.8 mg, 13 µmol) in a 20-mL vial was added THF (400 mg), HSiMe(OTMS)$_2$ (141 µL, 0.499 mmol, 2.5 equiv), cyclohexene (40 µL, 0.40 mmol), and desloratadine (62.0 mg, 0.199 mmol). The mixture was heated at 100° C. for 2 d. The resulting mixture was cooled to room temperature, and the volatile materials were evaporated. To the residue was added ethyl acetate (5 mL) and saturated NaHCO$_3$ (aq, 2 mL), and the mixture was stirred vigorously for at room temperature for 30 min. The organic layer was separated, and the aqueous layer was extracted with ethyl acetate (2 mL×2). The combined organic layer was washed with brine, dried over MgSO$_4$, filtered, and the solvents were evaporated. The residue was purified by preparative TLC (5:5 acetone:methanol on a TLC plate pre-treated with Et$_3$N) to afford the product as a brown liquid (83.6 mg, 79% yield). $^1$H NMR (400 MHz, CDCl$_3$) δ 8.48 (d, J=1.3 Hz, 1H), 7.50 (d, J=1.1 Hz, 1H), 7.16-7.04 (m, 3H), 3.47-3.29 (m, 2H), 3.11-2.95 (m, 2H), 2.91-2.70 (m, 2H), 2.70-2.57 (m, 2H), 2.46-2.36 (m, 1H), 2.36-2.22 (m, 3H), 1.82 (s, 1H), 0.23 (s, 3H), 0.09 (s, 18H). $^{13}$C NMR (101 MHz, CDCl$_3$) δ 158.11 (s), 150.92 (s), 142.54 (s), 139.78 (s), 139.60 (s), 138.06 (s), 132.65 (s), 132.63 (s), 132.41 (s), 131.34 (s), 130.82 (s), 128.93 (s), 126.06 (s), 48.30 (s, two peaks overlapping), 32.88 (s), 32.71 (s), 31.91 (s), 31.63 (s), 1.94 (s), 0.43 (s). HRMS (ESI+) calcd for [C$_{26}$H$_{40}$ClN$_2$O$_2$Si$_3$$^+$]: 531.2081, found: 531.2075.

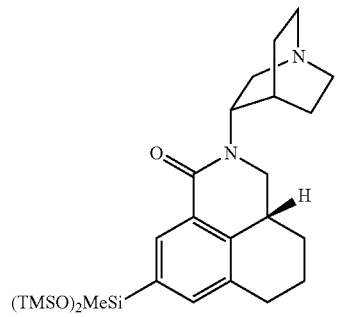

To [Ir(cod)OMe]$_2$ (4.0 mg, 6.0 µmol) and 2,4,7-trimethylphenanthroline (2.8 mg, 13 µmol) in a 20-mL vial was added THF (300 mg), HSiMe(OTMS)$_2$ (141 µL, 0.499 mmol, 2.5 equiv), cyclohexene (20 µL, 0.20 mmol), and palonosetron (59.3 mg, 0.200 mmol). The mixture was heated at 100° C. for 2 d. The resulting mixture was cooled to room temperature, and the volatile materials were evaporated. To the residue was added ethyl acetate (5 mL) and saturated NaHCO$_3$ (aq, 2 mL), and the mixture was stirred vigorously for at room temperature for 30 min. The organic layer was separated, and the aqueous layer was extracted with ethyl acetate (2 mL×2). The combined organic layer was washed with brine, dried over MgSO$_4$, filtered, and the solvents were evaporated. The residue was purified by preparative TLC (5:5 acetone:methanol on a TLC plate pre-treated with Et$_3$N) to afford the product J as a clear yellow wax (89.9 mg, 87% yield). $^1$H NMR (500 MHz, CDCl$_3$) δ 8.09 (s, 1H), 7.39 (s, 1H), 4.84-4.76 (m, 1H), 3.66 (dd, J=11.8, 4.7 Hz, 1H), 3.33 (ddd, J=14.0, 10.2, 1.8 Hz, 1H), 3.23 (t, J=12.5 Hz, 1H), 3.03-2.92 (m, 2H), 2.92-2.73 (m, 6H), 2.10-1.98 (m, 2H), 1.93 (dd, J=5.3, 2.7 Hz, 1H), 1.84-1.68 (m, 3H), 1.65-1.55 (m, 1H), 1.47 (td, J=10.8, 4.5 Hz, 1H), 1.41-1.30 (m, 1H), 0.24 (s, 3H), 0.10 (s, 9H), 0.09 (s, 9H). $^{13}$C NMR (126 MHz, CDCl$_3$) δ 165.92 (s), 138.16 (s), 137.14 (s), 136.73 (s), 133.62 (s), 131.15 (s), 128.12 (s), 52.48 (s), 50.22 (s), 48.04 (s), 47.66 (s), 46.92 (s), 35.15 (s), 28.73 (s), 28.17 (s), 26.39 (s), 26.26 (s), 22.24 (s), 22.06 (s), 1.96 (s), 0.18 (s). HRMS (ESI+) calcd for [C$_{26}$H$_{45}$N$_2$O$_3$Si$_3^+$] (M+H$^+$): 517.2732, found: 517.2725.

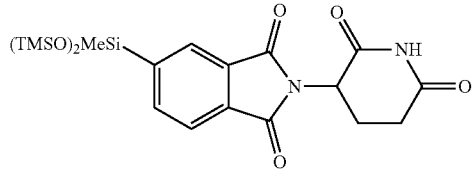

To [Ir(cod)OMe]$_2$ (4.0 mg, 6.0 I±mol) and 2,4,7-trimethylphenanthroline (2.8 mg, 13 μmol) in a 20-mL vial was added THF (300 mg), HSiMe(OTMS)$_2$ (222 mg, 1.00 mmol, 5 equiv), cyclohexene (40 μL, 0.40 mmol), and thalidomide (51.9 mg, 0.201 mmol). The mixture was heated at 120° C. for 2 d. The resulting mixture was cooled to room temperature, and the volatile materials were evaporated. To the residue was added ethyl acetate (5 mL) and saturated NaHCO$_3$ (aq, 2 mL), and the mixture was stirred vigorously for at room temperature for 30 min. The organic layer was separated, and the aqueous layer was extracted with ethyl acetate (2 mL×2). The combined organic layer was washed with brine, dried over MgSO$_4$, filtered, and the solvents were evaporated. The residue was purified by preparative TLC (3:7 ethyl acetate:hexanes) to afford the product as a colorless solid (43.2 mg, 45% yield). $^1$H NMR (500 MHz, CDCl$_3$) δ 8.47 (s, 1H), 8.04 (s, 1H), 7.94 (d, J=7.1 Hz, 1H), 7.84 (d, J=7.1 Hz, 1H), 5.01 (dd, J=11.7, 4.7 Hz, 1H), 3.01-2.69 (m, 3H), 2.21-2.04 (m, 1H), 0.31 (s, 3H), 0.12 (s, 18H). $^{13}$C NMR (126 MHz, CDCl$_3$) δ 171.31 (s), 168.29 (s), 167.83 (s), 167.61 (s), 147.49 (s), 139.46 (s), 132.43 (s), 130.69 (s), 128.29 (s), 122.86 (s), 49.35 (s), 31.50 (s), 22.75 (s), 1.97 (s), —0.05 (s). HRMS (ESI+) calcd for [C$_{20}$H$_{31}$N$_2$O$_6$Si$_3$](M+H$^+$): 479.1484, found: 479.1492; calcd for [C$_{20}$H$_{30}$N$_2$NaO$_6$Si$_3^+$] (M+Na$^+$): 501.1304, found: 501.1304.

The silylation of arenes was also conducted without a hydrogen acceptor (acceptorless procedure): To a solution of [Ir(cod)OMe]$_2$ (3.0 mg, 4.5 μmol) and L3 (2.1 mg, 9.3 μmol) in THF (300 mg) in a 20-mL vial was added the desired amount of HSiMe(OSiMe$_3$)$_2$, and the substrate, and the mixture was heated to the desired temperature for 24-48 h. The yields were determined by GC analysis

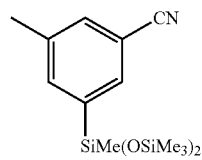

From 3-methylbenzonitrile (35.6 μL, 0.300 mmol) and 1.5 equiv silane following the general acceptorless procedure. The mixture was heated at 100° C. for 1 d. The product was obtained in 80% yield determined by GC analysis.

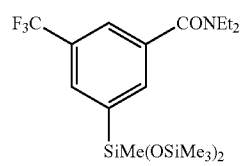

From N,N-diethyl-3-(trifluoromethyl)benzamide (73.6 mg, 0.300 mmol) and 1.5 equiv silane following the general acceptorless procedure. The mixture was heated at 100° C. for 1 d. The product was obtained in 81% yield determined by GC analysis.

Example 3

The silylarenes generated from the present methods underwent various reactions, e.g., cross-coupling with aryl bromides to form biaryl moieties and oxidation to form phenols (Scheme 8). These silylarenes also underwent bromination and iodination, and these halogenation reactions are more facile and can be conducted with simpler reagents than the copper-mediated halogenation of arylboronates (Murphy, et al., J. Am. Chem. Soc. 129:15434-15435 (2007)). Furthermore, 1,4-addition to acrylates was conducted in the presence of a rhodium catalyst. Because the functionalization of arylsilanes and arylboronates occur under different conditions, the mild method to generate arylsilanes creates many opportunities for diversification of polysubstituted arenes.

Shown in Scheme 8 is a series of selective, sequential functionalizations of the arylsilanes bearing a Bpin group (10b). For example, the Bpin group was selectively transformed into an aryl group without affecting the silyl group, and the resulting product was further oxidized to 62. The chemoselectivity in the first step arises from the requirement for a strong base (KOTMS) for the activation of the silyl group versus the weak base, K$_2$CO$_3$, needed for the Suzuki coupling. Similarly, because oxidation of the silyl group requires TBAF, the Bpin group was selectively oxidized with H$_2$O$_2$ under basic conditions while the silyl group remained intact. The resulting product underwent iodination smoothly to give 64.

On the other hand, the conditions for the halogenation of silylarenes did not affect the Bpin group. Thus, the resulting intermediate 65 and 67 can be further elaborated via many of the transformations available to the Bpin group, such as cyanation (Liskey, et al., J. Am. Chem. Soc. 132:11389-11391 (2010)) and fluorination (Fier, et al., J. Am. Chem. Soc. 135:2552-2559 (2013)).

Scheme 7. Derivatization of the silylarene products.
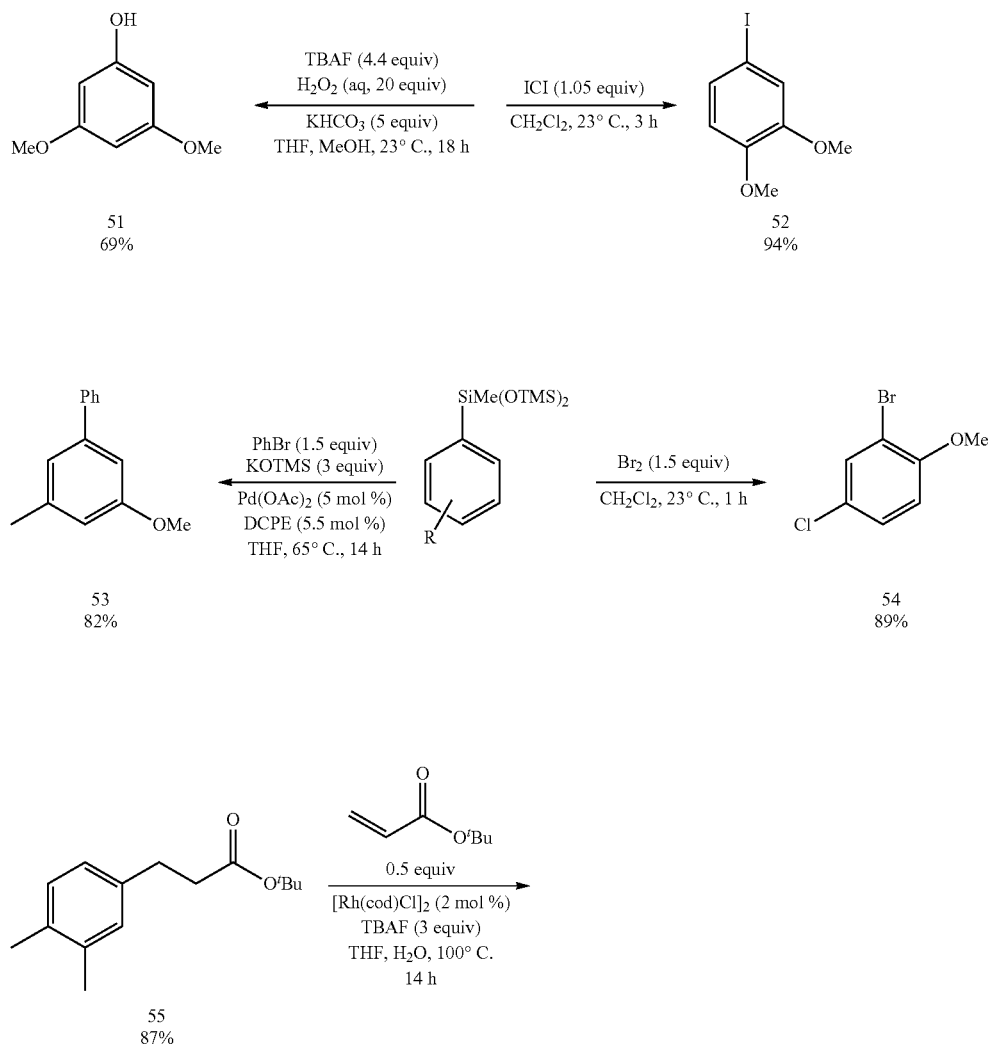
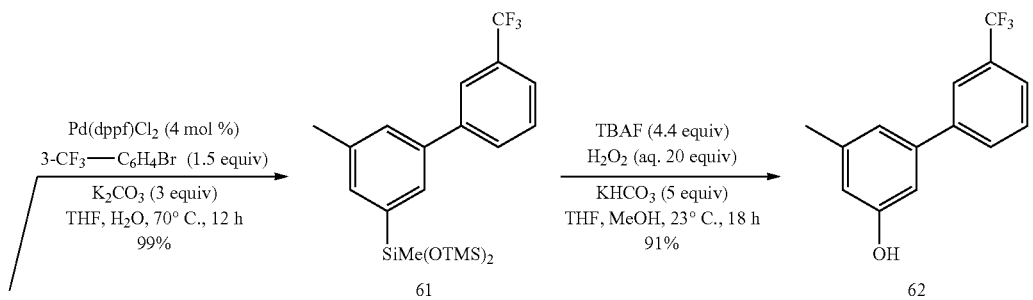
Scheme 8. Sequential functionalization of 10b.

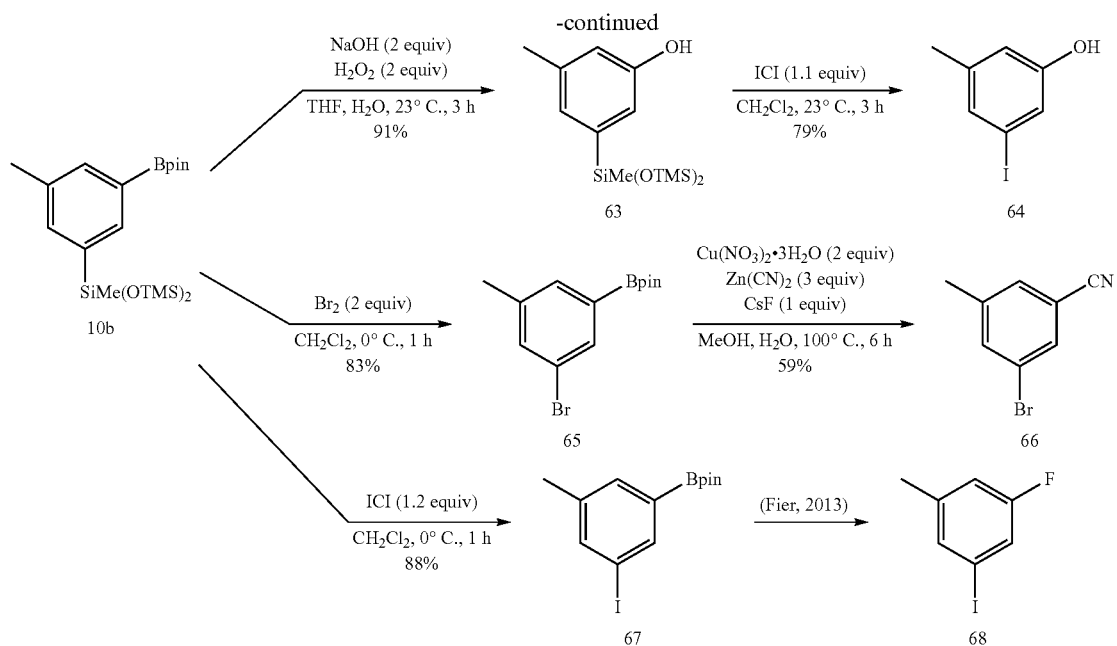

The silylarene products were subjected to further transformations, such as oxidation to form phenols, halogenations, and cross-couplings, and the corresponding functionalized arenes were obtained in good yields (Scheme 9).

Notably, the methods for functionalization of aryl-silicon bonds were suitable for several complex silylarenes, which should allow potential late-stage func-tionalization of complex molecules.

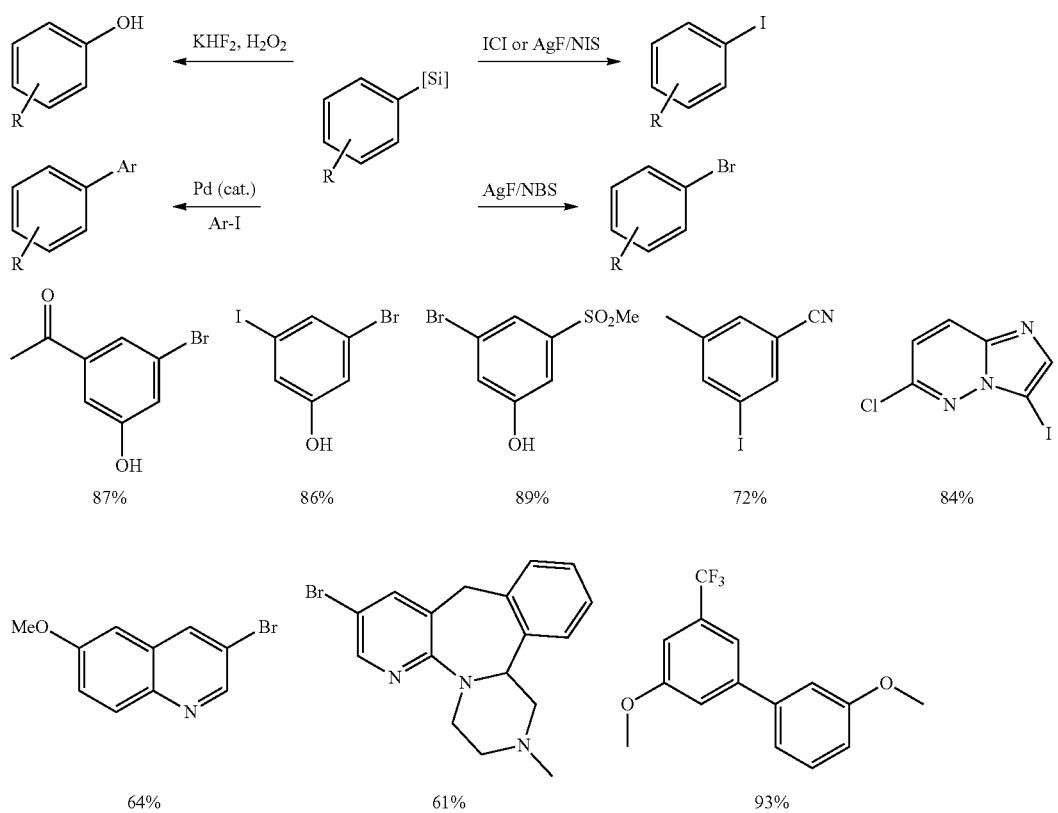

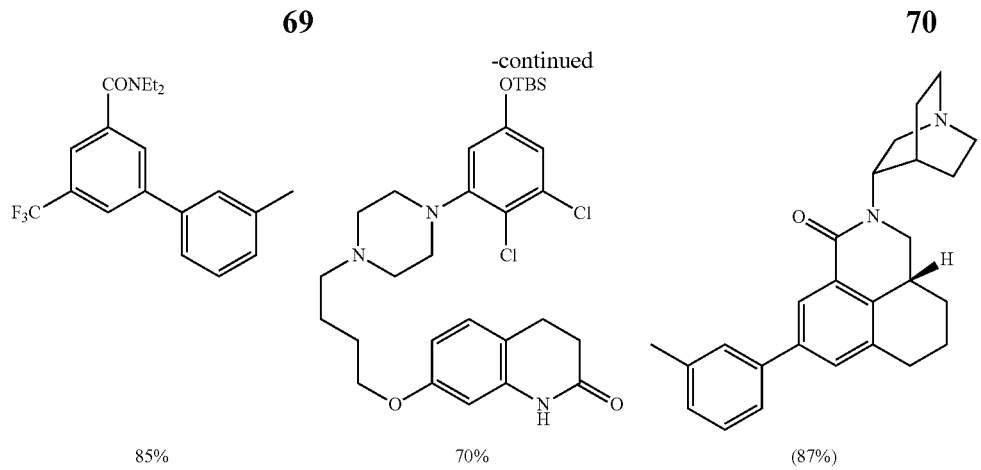

85%  70%  (87%)

Exemplary Preparations

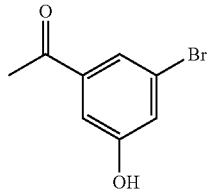

To C (79.3 mg, 0.189 mmol) in DMF (0.6 mL) was added KHF$_2$ (44.3 mg, 0.567 mmol, 3.0 equiv) and H$_2$O$_2$ (56 μL of 30% w/w in H$_2$O, 0.49 mmol, 2.6 equiv), and the mixture was stirred at room temperature for 16 h and then partitioned between H$_2$O and ethyl acetate (4 mL each). The organic layer was separated, and the aqueous layer was extracted with ethyl acetate (4 mL). The combined organic layer was washed with H$_2$O (3 mL) and brine (2 mL), dried over MgSO$_4$, and concentrated. The residue was purified by flash column chromatography (0→50% ethyl acetate in hexanes) to afford the product as a colorless solid (35.3 mg, 87% yield). $^1$H NMR (500 MHz, CDCl$_3$) δ 7.62 (s, 1H), 7.46-7.42 (m, 1H), 7.25 (d, J=0.9 Hz, 1H), 6.55 (bs, 1H), 2.59 (s, 3H). $^{13}$C NMR (126 MHz, CDCl$_3$) δ 197.94 (s), 157.18 (s), 139.47 (s), 124.30 (s), 123.89 (s), 123.30 (s), 113.94 (s), 26.96 (s). HRMS (ESI-) calcd for [C$_8$H$_6$BrO$_2$$^-$] (M-H$^+$): 212.9557, found: 212.9557.

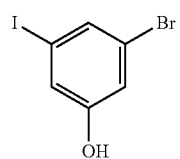

The oxidation of K (89.9 mg, 0.179 mmol) was conducted following the procedure for the oxidation of C. The residue was purified by flash column chromatography (0→30% ethyl acetate in hexanes) to afford the product as a colorless solid (46.2 mg, 86% yield). $^1$H NMR (500 MHz, CDCl$_3$) δ 7.43 (d, J=1.3 Hz, 1H), 7.17-7.12 (m, 1H), 6.99-6.95 (m, 1H), 5.09 (bs, 1H). $^{13}$C NMR (126 MHz, CDCl$_3$) δ 156.54 (s), 132.48 (s), 123.72 (s), 123.31 (s), 118.71 (s), 94.36 (s). The NMR spectra agree with the literature data.[8]

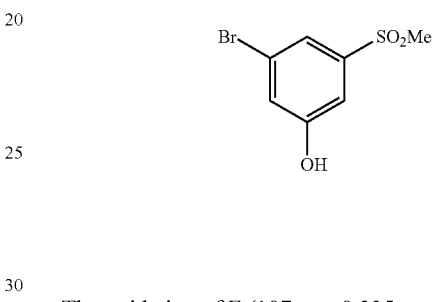

The oxidation of F (107 mg, 0.235 mmol) was conducted following the procedure for the oxidation of C. The residue was purified by flash column chromatography (0→60% ethyl acetate in hexanes) to afford the product as a colorless solid (52.6 mg, 89% yield). $^1$H NMR (500 MHz, CDCl$_3$) δ 7.57 (s, 1H), 7.39 (s, 1H), 7.29 (s, 1H), 3.11 (s, 3H). $^{13}$C NMR (126 MHz, CDCl$_3$) δ 157.94 (s), 142.11 (s), 124.86 (s), 124.11 (s), 122.03 (s), 113.13 (s), 44.57 (s). HRMS (ESI-) calcd for [C$_7$H$_6$BrO$_3$S] (M-H$^+$): 248.9227, found: 248.9227.

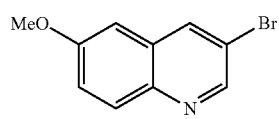

To G (92.5 mg, 0.244 mmol) in MeCN (2 mL) was added AgF (61.8 mg, 0.488 mmol, 2 equiv) and N-bromosuccinimide (47.8 mg, 0.268 mmol, 1.1 equiv), and the mixture was stirred at room temperature for 3 h. The mixture was then filtered, diluted with ethyl acetate (3 mL), and washed with saturated NaHCO$_3$ (4 mL). The aqueous layer was extracted with ethyl acetate (4 mL), the combined organic layer washed with brine, dried with MgSO$_4$, filtered, and the solvents were evaporated. The residue was purified by preparative TLC (2:8 ethyl acetate:hexanes) to afford the product as a colorless solid (37.4 mg, 64% yield). $^1$H NMR (500 MHz, CDCl$_3$) δ 8.72 (d, J=2.1 Hz, 1H), 8.16 (d, J=1.8 Hz, 1H), 7.94 (d, J=9.2 Hz, 1H), 7.34 (dd, J=9.2, 2.7 Hz, 1H), 6.93 (d, J=2.6 Hz, 1H), 3.90 (s, 3H). $^{13}$C NMR (126 MHz, CDCl$_3$) δ 158.59 (s), 148.81 (s), 142.57 (s), 136.02 (s), 130.96 (s), 130.43 (s), 122.76 (s), 117.83 (s), 104.30 (s), 55.71 (s). HRMS (ESI+) calcd for [C$_{10}$H$_9$BrNO$^+$] (M+H$^+$): 237.9862, found: 237.9861.

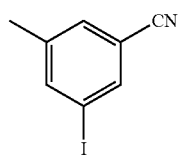

To A (71.6 mg, 0.212 mmol) in CH$_2$Cl$_2$ (1 mL) was added a solution of ICl (37.9 mg, 0.233 mmol) in CH$_2$Cl2 (1 mL) dropwise at 0° C., and the mixture was stirred at room temperature for 2 h. The volatile materials were evaporated, and the residue was purified by preparative TLC (1:9 ethyl acetate:hexanes) to afford the product as a yellow solid (37.0 mg, 72% yield). $^1$H NMR (600 MHz, CDCl$_3$) δ 7.77 (s, 2H), 7.42 (s, 1H), 2.35 (s, 3H). $^{13}$C NMR (151 MHz. CDCl$_3$) δ 142.74 (s), 141.26 (s), 137.63 (s), 131.91 (s), 117.39 (s), 113.99 (s), 93.92 (s), 20.90 (s). The NMR spectra agree with the literature data.[9]

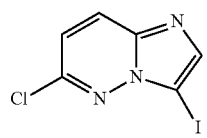 [SMILES: Clc1ccc2ncc(I)n2n1]

To E (64.0 mg, 0.171 mmol) in MeCN (2 mL) was added AgF (43 mg, 0.34 mmol) and N-iodosuccinimide (38 mg, 0.17 mmol), and the mixture was stirred at room temperature for 2 h. The mixture was then partitioned between ethyl acetate (4 mL) and aqueous K2CO3 solution (4 mL). The organic phase was separated, and the aqueous phase was extracted with ethyl acetate (4 mL). The combined organic layer was washed with water (4 mL), brine (4 mL), and dried over MgSO4, and filtered. The volatile materials were evaporated, and the residue was purified by flash column chromatography to afford the product as a light yellow solid (40.3 mg, 84% yield). $^1$H NMR (500 MHz, CDCl$_3$) δ 7.86 (d, J=9.4 Hz, 1H), 7.83 (s, 1H), 7.09 (d, J=9.4 Hz, 1H). $^{13}$C NMR (126 MHz, CDCl$_3$) δ 148.05 (s), 141.13 (s), 140.08 (s), 126.98 (s), 119.51 (s), 69.20 (s). HRMS (ESI+) calcd for [C$_6$H$_4$ClIN$_3$$^+$] (M+H$^+$): 279.9133, found: 279.9133.

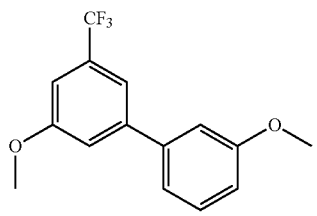 [SMILES: COc1cccc(-c2cc(OC)cc(C(F)(F)F)c2)c1]

To a solution of Pd(OAc)$_2$ (1.9 mg, 8.5 μmol) and 1,2-bis(dicyclohexylphosphino)ethane (3.8 mg, 9.0 μmol) in toluene (600 mg) was added D (87.0 mg, 0.219 mmol), 3-iodoanisole (39.5 mg, 0.169 mmol), and KOSiMe$_3$ (65 mg, 0.51 mmol). The mixture was stirred at room temperature for 20 min and heated at 80° C. for 16 h. The mixture was then filtered over a pad of celite, and the volatile materials were evaporated. The residue was purified by preparative TLC (1:9 ethyl acetate:hexanes) to afford the product as a colorless liquid (44.2 mg, 93% yield). $^1$H NMR (600 MHz, CDCl$_3$) δ 7.43 (s, 1H), 7.39 (t, J=7.9 Hz, 1H), 7.28 (s, 1H), 7.18 (d, J=7.7 Hz, 1H), 7.15-7.09 (m, 2H), 6.95 (dd, J=8.2, 2.2 Hz, 1H), 3.91 (s, 3H), 3.88 (s, 3H). $^{13}$C NMR (151 MHz, CDCl$_3$) δ 160.25 (s), 160.22 (s), 143.61 (s), 141.41 (s), 132.34 (q, J=32.2 Hz), 130.13 (s), 124.15 (q, J=272.6 Hz), 119.80 (s), 116.57 (s), 116.56 (q, J=4.3 Hz), 113.58 (s), 113.19 (s), 109.55 (q, J=3.7 Hz), 55.75 (s), 55.50 (s). HRMS (EI+) calcd for [C$_{15}$H$_{13}$F$_3$O$_2$]: 282.0868, found: 282.0870.

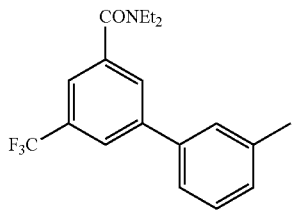

To a solution of Pd(OAc)$_2$ (1.6 mg, 7.1 μmol) and 1,2-bis(dicyclohexylphosphino)ethane (3.2 mg, 7.6 μmol) in toluene (500 mg) was added B (87.0 mg, 0.187 mmol), 3-iodotoluene (31.4 mg, 0.144 mmol), and KOSiMe$_3$ (55 mg, 0.43 mmol). The mixture was stirred at room temperature for 20 min and heated at 80° C. for 16 h. The mixture was then filtered over a pad of celite, and the volatile materials were evaporated. The residue was purified by flash column chromatography (0→30% ethyl acetate in hexanes) to afford the product as a viscous colorless liquid (41.1 mg, 85% yield). $^1$H NMR (600 MHz, CDCl$_3$) δ 7.85 (s, 1H), 7.76 (s, 1H), 7.60 (s, 1H), 7.43-7.38 (m, 2H), 7.36 (t, J=7.5 Hz, 1H), 7.23 (d, J=7.3 Hz, 1H), 3.59 (d, J=5.8 Hz, 2H), 3.28 (d, J=5.8 Hz, 2H), 2.43 (s, 3H), 1.29 (s, 3H), 1.15 (s, 3H). $^{13}$C NMR (151 MHz, CDCl$_3$) δ 169.83 (s), 142.81 (s), 139.06 (s), 138.95 (s), 138.63 (s), 131.53 (q, J=32.5 Hz), 129.29 (s), 129.13 (s), 128.39 (s), 128.05 (s), 124.66 (q, J=3.7 Hz), 124.40 (s), 123.92 (q, J=272.7 Hz), 121.90 (q, J=3.7 Hz), 43.55 (s), 39.65 (s), 21.58 (s), 14.36 (s), 12.99 (s). $^{19}$F NMR (376 MHz. CDCl$_3$) δ −61.87 (s). HRMS (EI+) calcd for [C$_{19}$H$_{20}$F$_3$NO]: 335.1497, found: 335.1493.

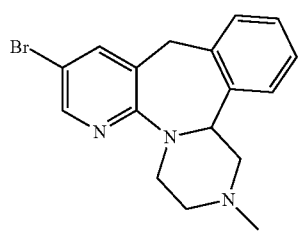 [SMILES: CN1CCN2c3ncc(Br)cc3Cc3ccccc3C2C1]

To a solution of H (45.7 mg, 0.0941) in MeCN (1 mL) under nitrogen was added AgF (23.9 mg, 0.188 mmol) and N-bromosuccinimide (17.8 mg, 0.100 mmol), and the mixture was stirred at room temperature for 2 h. The mixture was then diluted with ethyl acetate (4 mL), filtered, and washed with saturated NaHCO$_3$ (4 mL). The aqueous layer was extracted with ethyl acetate (4 mL), the combined organic layer washed with brine, dried with MgSO$_4$, filtered, and the solvents were evaporated. The residue was purified by preparative TLC (7:3 ethyl acetate:hexanes on a TLC plate pre-treated with Et$_3$N) to afford the product as a colorless solid (19.6 mg, 61% yield). $^1$H NMR (600 MHz, CDCl$_3$) δ 8.17 (d, J=1.9 Hz, 1H), 7.43 (d, J=1.8 Hz, 1H), 7.19-7.10 (m, 4H), 4.47 (d, J=13.3 Hz, 1H), 4.33 (d, J=9.6 Hz, 1H), 3.65 (d, J=12.7 Hz, 1H), 3.43 (t. J=11.8 Hz, 1H), 3.38 (d, J=13.3 Hz, 1H), 2.94 (d, J=11.0 Hz, 1H), 2.84 (d, J=11.1 Hz, 1H), 2.49 (t, J=10.5 Hz, 1H), 2.37 (s, 3H), 2.32 (td, J=11.1, 2.7 Hz, 1H). $^{13}$C NMR (151 MHz, CDCl$_3$) δ 158.22 (s), 146.92 (s), 137.23 (s), 137.01 (s), 136.91 (s), 133.06 (s), 129.86 (s), 128.21 (s), 127.79 (s), 127.42 (s), 112.22 (s), 64.86 (s), 64.29 (s), 55.54 (s), 49.20 (s), 45.95 (s), 38.24 (s). HRMS (ESI+) calcd for [C$_{17}$H$_{19}$BrN$_3^+$] (M+H$^+$): 344.0757, found: 344.0755.

The conditions for the silylation of simple arenes can be applied to the functionalization of complex pharmaceutical compounds, and these reactions further demonstrated the functional group compatibility of the iridium-catalyzed silylation as well as the relatively reactivity of different types of arenes (Scheme 10). For example, silylation of clopidogrel, duloxetine, and ketotifen all occurred selectively at the 2-position of the thiophene moiety over on the benzene or naphthalene ring. In addition, the secondary alkyl amine moiety in duloxetine was in-situ protected and did not interfere with the C—H silylation. In contrast, the C—H borylation is not compatible with secondary alkyl amines. Silylation of the pyridine ring in mirtazapine also took precedence over silylation of the benzene ring, although 14% of disilylation products were also obtained. Furthermore, the imidazoline moiety in clonidine, the secondary amide in aripiprazole, and the imides in thalidomide were all tolerated, and single isomers of products were obtained because of the steric effects of the substituents. The secondary amine moiety in bupropion was not silylated during the reaction, presumably because of the steric hindrance of the tert-butyl group.

Scheme 10. C-H silylation of complex pharmaceutical compounds.$^a$

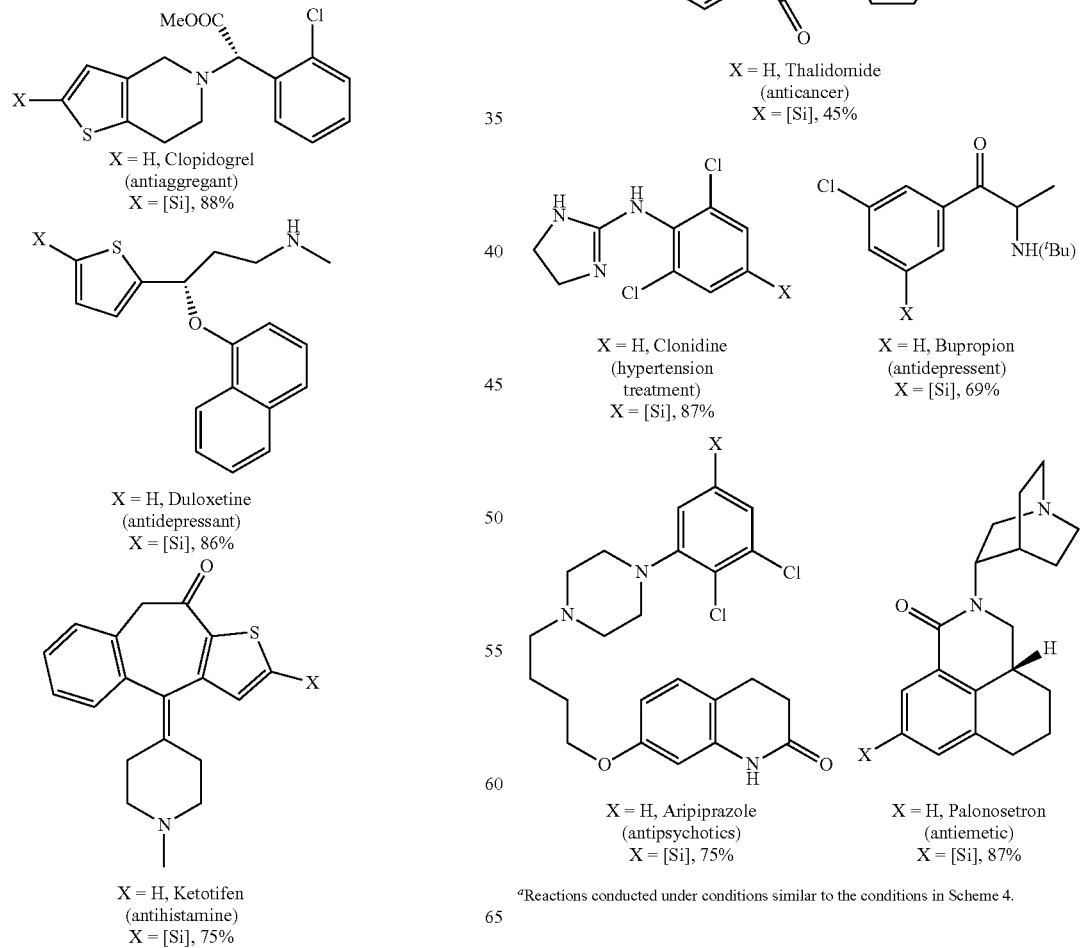

$^a$Reactions conducted under conditions similar to the conditions in Scheme 4.

Exemplary Preparations

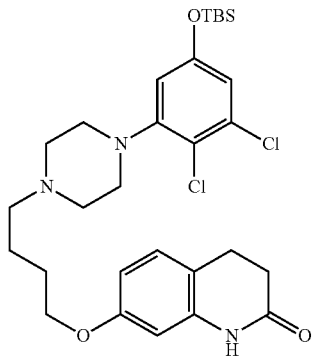 [SMILES: CC(C)(C)[Si](C)(C)Oc1cc(Cl)c(Cl)c(N2CCN(CCCCOc3ccc4c(c3)NC(=O)CC4)CC2)c1]

To a solution of I (66.9 mg, 0.100 mmol) in DMF (0.5 mL) was added KHF$_2$ (23.4 mg, 0.300 mmol) and H$_2$O$_2$ (30 µL, 30% aqueous solution, 0.26 mmol), and the mixture was stirred at room temperature for 16 h. The mixture was diluted with H$_2$O (10 mL) and extracted with a mixture of MeOH and ethyl acetate (1:20, 20 mL×3). The organic layer was dried by Na$_2$SO$_4$ and concentrated. The residue was dissolved in anhydrous DMF (2 mL), and to the solution was added imidazole (27.2 mg, 0.300 mmol) and tert-butyldimethylchlorosilane (45.2 mg, 0.300 mmol), and the mixture was stirred at room temperature for 16 h. The mixture was partitioned between diethyl ether (4 mL) and H$_2$O (4 mL), and the organic layer was separated. The aqueous layer was extracted with diethyl ether (3 mL×3), the combined organic layer washed with H$_2$O (4 mL), brine (4 mL), dried by MgSO$_4$, and concentrated. The residue was purified by flash column chromatography (0→70% ethyl acetate in hexanes on silica pre-treated with Et$_3$N) to afford the product as a colorless solid (40.7 mg, 70% yield). $^1$H NMR (500 MHz. CDCl$_3$) δ 8.75 (s, 1H), 7.03 (d, J=8.2 Hz, 1H), 6.66 (s, 1H), 6.51 (d, J=8.1 Hz, 1H), 6.44 (s, 1H), 6.37 (s, 1H), 3.95 (t, J=6.0 Hz, 2H), 3.03 (s, 4H), 2.89 (t, J=7.3 Hz, 2H), 2.79-2.51 (m, 6H), 2.50-2.40 (m, 2H), 1.86-1.76 (m, 2H), 1.76-1.64 (m, 2H), 0.96 (s, 9H), 0.19 (s, 6H). $^{13}$C NMR (126 MHz. CDCl$_3$) δ 172.28 (s), 158.77 (s), 154.81 (s), 151.68 (s), 138.29 (s), 133.91 (s), 128.71 (s), 119.95 (s), 116.29 (s), 115.77 (s), 111.25 (s), 108.77 (s), 102.35 (s), 67.97 (s), 58.27 (s), 53.36 (s), 51.41 (s), 31.20 (s), 27.36 (s), 25.73 (s), 24.68 (s), 23.57 (s), 18.33 (s), −4.33 (s). HRMS (ESI+) calcd for [C$_{29}$H$_{42}$Cl$_2$N$_3$O$_3$Si$^+$] (M+H$^+$): 578.2367, found: 578.2359.

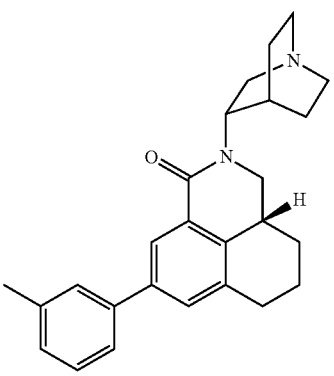 [SMILES: Cc1cccc(-c2cc3c4c(c2)C(=O)N(C2CN5CCC2CC5)C[C@@H]4CCC3)c1]

To a solution of Pd(OAc) (1.8 mg, 8.0 µmol) and 1,2-bis(dicyclohexylphosphino)ethane (3.6 mg, 8.5 µmol) in toluene (600 mg) was added J 90.1 mg (0.174 mmol), 3-iodotoluene (34.4 mg, 0.158 mmol), and KOSiMe$_3$ (60.7 mg, 0.474 mmol). The mixture was stirred at room temperature for 20 min and then at 80° C. for 16 h. The mixture was diluted with ethyl acetate (3 mL) and filtered over a pad of celite. The solvents were evaporated, and the residue was dissolved in Et$_2$O (2 mL) and treated with HCl (2 N ethereal solution, 2 mL), and the precipitate was separated and purified by HPLC (C18 column, 19 mm×250 mm, 10 µm pore, 30 ml/min flow rate, 0→50% MeCN in H$_2$O over 15 min). The HPLC fractions were combined, and the solvents were reduced to 10 mL. The solution was treated with K$_2$CO$_3$ (aqueous solution, 10 mL) and extracted with ethyl acetate (10 mL×3). The combined organic layer was washed with brine, dried over MgSO$_4$, and filtered, and the solvents were evaporated to afford the product as a colorless solid (42.6 mg, 70% yield). $^1$H NMR (500 MHz. CDCl$_3$) δ 8.14 (s, 1H), 7.45 (d, J=10.4 Hz, 2H), 7.41 (d, J=7.8 Hz, 1H), 7.31 (t, J=7.6 Hz, 1H), 7.15 (d, J=7.4 Hz, 1H), 4.90-4.77 (m, 1H), 3.70 (dd, J=11.8, 4.7 Hz, 1H), 3.45-3.37 (m, 1H), 3.29 (t, J=12.5 Hz, 1H), 3.15-3.00 (m, 2H), 2.99-2.78 (m, 6H), 2.40 (s, 3H), 2.10 (t, J=12.7 Hz, 2H), 2.01 (d, J=2.4 Hz, 1H), 1.91-1.72 (m, 3H), 1.68 (ddd, J=17.2, 11.7, 5.8 Hz, 1H), 1.55 (t. J=12.0 Hz, 1H), 1.40 (dd, J=23.9, 11.4 Hz, 1H). $^{13}$C NMR (126 MHz, CDCl$_3$) δ 165.92 (s), 140.41 (s), 139.89 (s), 138.49 (s), 135.99 (s), 135.33 (s), 130.77 (s), 129.51 (s), 128.78 (s), 128.26 (s), 127.94 (s), 124.98 (s), 124.15 (s), 52.11 (s), 50.43 (s), 48.41 (s), 47.55 (s), 46.87 (s), 35.05 (s), 28.41 (s), 28.35 (s), 26.50 (s), 26.36 (s), 22.14 (s), 22.07 (s), 21.62 (s). MS (ESI+) calcd for [C$_{26}$H$_{31}$N$_2$O$^+$] (M+H$^+$): 387.2, found: 387.2.

With the catalyst developed for the intermolecular silylation of arenes under mild conditions with regioselectivities complementing or surpassing those of borylation, the present invention provides a method that serves as a practical alternative to the C—H borylation in forging arenes with substitution patterns difficult to access otherwise. Additionally, the same or a similar catalyst can potentially be extended to other silylation reactions. As an example, the intramolecular cyclization of 70 (eq 5) catalyzed by an exemplary catalyst of the invention proceeded at much lower temperature (80 vs 135° C.) than the reaction catalyzed by Rh(PPh$_3$)$_3$Cl reported by Takai and coworkers (Ureshino, et al., J. Am. Chem. Soc. 132:14324-14326 (2010)). Furthermore, because the ligands in the catalysts of use in the invention are chiral, the catalysts are of use in the enantioselective silylation of aromatic and aliphatic C—H bonds, leading to chiral diol products can be made possible. One-pot hydrosilylation of benzophenone (72) followed by dehydrogenative silylation with catalyst generated from [Rh(coe)OH]$_2$ and L2 afforded product 73 in 84% isolated yield with a moderate e.r. (74:26) (eq 6). In comparison, at the same temperature, the cyclization reaction catalyzed by complex generated from [Ir(cod)OMe]$_2$ and Me$_4$Phen led to only 9% conversion of the hydridosilylether intermediate. After slight adjustment of the rhodium precursor and the ligand, a synthetically useful e.r. of 95:5 was achieved with catalyst generated from [Rh(cod)Cl]$_2$ and L3 (eq 7).

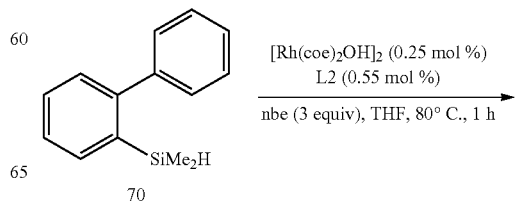

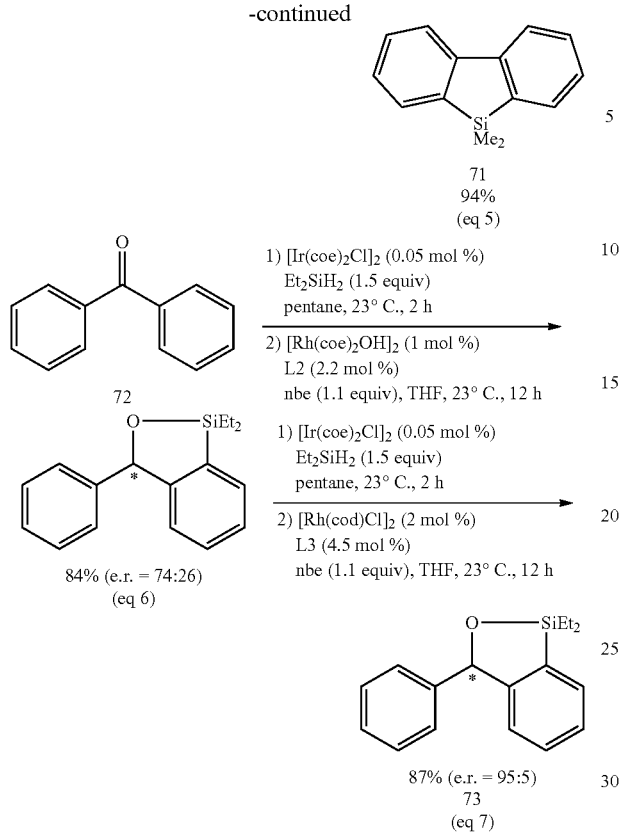

71
94%
(eq 5)

72

1) [Ir(coe)₂Cl]₂ (0.05 mol %)
   Et₂SiH₂ (1.5 equiv)
   pentane, 23° C., 2 h
2) [Rh(coe)₂OH]₂ (1 mol %)
   L2 (2.2 mol %)
   nbe (1.1 equiv), THF, 23° C., 12 h

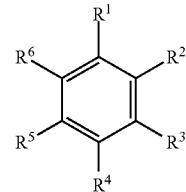

84% (e.r. = 74:26)
(eq 6)

1) [Ir(coe)₂Cl]₂ (0.05 mol %)
   Et₂SiH₂ (1.5 equiv)
   pentane, 23° C., 2 h
2) [Rh(cod)Cl]₂ (2 mol %)
   L3 (4.5 mol %)
   nbe (1.1 equiv), THF, 23° C., 12 h 87% (e.r. = 95:5)
73
(eq 7)

The invention has been illustrated by reference to several exemplary embodiments. Published resources cited herein are incorporated by reference herein for their respective teachings of standard laboratory methods found therein. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls.

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, intermediates, elements, or other compositions, or concentrations stated or otherwise presented herein in a list, table, or other grouping (such as metabolic pathway enzymes shown in a FIGURE), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein. Accordingly, it is intended that the invention be limited only by the spirit and scope of appended claims, and of later claims, and of either such claims as they may be amended during prosecution.

What is claimed is:

1. A reaction mixture for silylating an arene substrate, said reaction mixture comprising:
   (i) a substituted arene or heteroarene substrate comprising a silylatable moiety;
   (ii) a liganded metal capable of catalyzing said silylating;
   (iii) optionally, a hydrogen acceptor; and
   (iv) a silicon source of Formula I:

$$R^t-\underset{R^u}{\overset{R^s}{\underset{|}{\overset{|}{Si}}}}H \quad (I)$$

in which $R^s$, $R^t$ and $R^u$ are independently from substituted or unsubstituted alkyl, substituted or unsubstituted heteroalkyl and $XR^x$, in which X is a heteroatom and $R^x$ is H or substituted or unsubstituted alkyl, substituted or unsubstituted aryl or substituted silyl, and one, two or three of, $R^s$, $R^t$ and $R^u$ is $XR^x$.

2. The reaction mixture according to claim 1, wherein said arene substrate has the formula:

$$\begin{array}{c}R^1\\R^6\diagup\diagdown R^2\\|\quad\quad|\\R^5\diagdown\diagup R^3\\R^4\end{array}$$

wherein
$R^1$, $R^2$, $R^3$, $R^4$, $R^5$, and $R^6$ are independently H, substituted or unsubstituted alkyl, substituted or unsubstituted heteroalkyl, substituted or unsubstituted aryl, substituted or unsubstituted heteroaryl, halogen, $BR^7R^8$, CN, $CF_3$, acyl, $-SO_2NR^7R^8$, $-NR^7R^8$, $-OR^7$, $-S(O)_2R^7$, $-C(O)R^7$, $-COOR^7$, $-CONR^7R^8$, $-S(O)_2OR^7$, $-OC(O)R^7$, $-C(O)NR^7R^8$, $-NR^7C(O)R^8$, $-NR^7SO_2R^8$ and $-NO_2$, wherein two or more of $R^1$, $R^2$, $R^3$, $R^4$, $R^5$, $R^6$, $R^7$ and $R^8$, together with the atoms to which they are bonded, are optionally joined to form a ring system which is substituted or unsubstituted cycloalkyl, substituted or unsubstituted heterocycloalkyl, substituted or unsubstituted aryl and substituted or unsubstituted heteroaryl
wherein
$R^7$ and $R^8$ are independently H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^7$ and $R^8$, together with the atoms to which they are bonded, are optionally joined to form a 5- to 7-membered ring which is substituted or unsubstituted cycloalkyl, substituted or unsubstituted heterocycloalkyl, substituted or unsubstituted aryl and substituted or unsubstituted heteroaryl.

3. The reaction mixture according to claim 1, wherein said substrate is 1,3-substituted.

4. The reaction mixture according to claim 1, wherein in said liganded metal, ligand is a phosphorus-containing ligand.

5. The reaction mixture according to claim 1, wherein in said liganded metal, ligand is a phosphorus-containing ligand, which is a biaryl ligand.

6. The reaction mixture according to claim 1, wherein in said liganded metal, ligand is a phosphorus-containing ligand, which is a biaryl ligand having the formula:

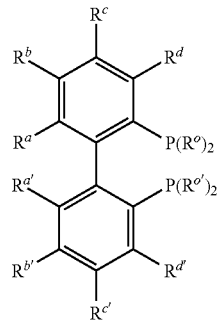

wherein
$R^a$, $R^b$, $R^c$, $R^d$, $R^o$, $R^{a'}$, $R^{b'}$, $R^{c'}$, $R^{d'}$, and $R^{o'}$, are each independently H, substituted or unsubstituted alkyl, substituted or unsubstituted heteroalkyl, halogen, CN, $CF_3$, acyl, $—SO_2NR^eR^f$, $—OR^e$, $—S(O)_2R^e$, $—C(O)R^e$, $—COOR^e$, $—CONR^eR^f$, $—S(O)_2OR^e$, $—OC(O)R^e$, $—C(O)NR^eR^f$, $—NR^eC(O)R^f$, $—NR^eSO_2R^f$ and $—NO_2$, wherein two or more of $R^a$, $R^b$, $R^c$, $R^d$, $R^e$, $R^f$, $R^{a'}$, $R^{b'}$, $R^{c'}$, and $R^{d'}$, together with the atoms to which they are bonded, are optionally joined to form a ring system which is substituted or unsubstituted cycloalkyl, substituted or unsubstituted heterocycloalkyl, substituted or unsubstituted aryl and substituted or unsubstituted heteroaryl;

$R^e$ and $R^f$ include independently H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^e$ and $R^f$, together with the atoms to which they are bonded, are optionally joined to form a 5- to 7-membered ring.

7. The reaction mixture according to claim 6, wherein each $R^o$ and $R^{o'}$ is independently substituted or unsubstituted alkyl, substituted or unsubstituted heteroalkyl moiety, an amine, a substituted or unsubstituted aryl or a substituted or unsbustituted heteroaryl moiety.

8. The reaction mixture according to claim 1, wherein said liganded metal atom is Ir or Rh.

9. The reaction mixture according to claim 1, wherein said liganded metal atom is formed in situ by complexing the metal atom with the ligand, wherein said metal atom is provided by a source of a metal atom.

10. The reaction mixture according to claim 9, wherein said metal atom source is [M(alkene)$_2$X], wherein M is the metal atom, X is halide or alkoxy moieties.

11. The reaction mixture according to claim 1, wherein said catalyst is bound to a solid support.

12. The reaction mixture according to claim 1, wherein said reaction mixture further comprises the silylated analogue of said arene substrate.

13. The reaction mixture according to claim 12, wherein the silylated analogue is further functionalized with $BR^7R^8$.

14. The reaction mixture according to claim 1, wherein said silicon source is a silane having at least one heteroatom and is in a molar ratio with said arene substrate of less than 10:1.

15. The reaction mixture according to claim 1, wherein said silicon source is a hydrosilane having at least one heteroatom and is in a molar ratio with said substrate of less than 10:1.

16. The reaction mixture according to claim 1, wherein said silicon source is a silane having at least one heteroatom and is in a molar ratio with said substrate of less than 10:1.

17. The reaction mixture according to claim 1, wherein said silicon source is a hydrosilane having at least one heteroatom and is in a molar ratio with said substrate of less than 10:1, and said metal atom is Ir or Rh.

18. The reaction mixture according to claim 1, wherein said silicon source is a silane having at least one heteroatom and is in a molar ratio with said substrate of less than 10:1, and said substrate is not substituted with a directing group.

19. The reaction mixture according to claim 1, further comprising an organic solvent.

20. The reaction mixture of claim 1, wherein in said liganded metal ligand is a substituted or unsubstituted phenanthroline, a substituted or unsubstituted bipyridine and a combination thereof.

21. A method for forming a silyl arene compound, said method comprising:
(a) forming a reaction mixture according to claim 1; and
(b) incubating said reaction mixture under conditions appropriate to form said silylarene compound.

22. The method according to claim 21, wherein said silyl arene compound is functionalized with the silyl moiety at the sterically least hindered site of the arene substrate.

23. The method according to claim 21, further comprising isolating the silyl arene compound.

24. The method according to claim 21, wherein said silyl arene is further functionalized with $BR^7R^8$.

25. The method according to claim 21, wherein said silyl arene is submitted to a reaction in which said silyl moiety is subsituted by another moiety.

26. The method according to claim 23, wherein the silyl moiety, $BR^7R^8$ and a combination thereof is substituted by another moiety.

27. The method according to claim 21, wherein said reaction mixture is incubated at a temperature from about 30° C. to about 100° C.

28. The method according to claim 21, wherein said substrate undergoes intramolecular silylation.

29. The reaction mixture according to claim 1, wherein the silicon source of Formula I is $(TMSO)_2MeSiH$.

30. A reaction mixture for silylating an arene substrate, said reaction mixture comprising:
(i) a substituted arene or heteroarene substrate comprising a silylatable moiety;
(ii) a liganded metal capable of catalyzing said silylating;

(iii) optionally, a hydrogen acceptor; and
(iv) a silicon source of Formula I:

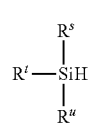 (I)

in which $R^s$, $R^t$ and $R^u$ are independently substituted or unsubstituted alkyl, substituted or unsubstituted heteroalkyl and $XR^x$, and one, two or three of Rs, Rt and Ru is $XR^x$, in which X is a heteroatom and $R^x$ is H or substituted or unsubstituted alkyl, substituted or unsubstituted aryl or substituted silyl in a ratio less than 10:1 to the substrate, wherein, when the silylatable moiety is a five-membered heteroarene ring containing an intra-annular heteroatom which is N, S and O, the silicon source includes at least one group bound to Si which is other than an alkyl group or a hydrogen.

* * * * *